US012357621B2

(12) United States Patent
Aronchik et al.

(10) Patent No.: US 12,357,621 B2
(45) Date of Patent: Jul. 15, 2025

(54) BET INHIBITORS AS A TREATMENT FOR MYELOFIBROSIS

(71) Applicant: Impact Biomedicines, Inc., Summit, NJ (US)

(72) Inventors: Ida Aronchik, Burlingame, CA (US); Roxxana Valeria Beltran Valencia, South San Francisco, CA (US); Maria Soraya Carrancio Anton, San Diego, CA (US); Henry H. Chang, San Francisco, CA (US); Shodeinde Coker, Princeton, NJ (US); Sharmila Das, North Brunswick, NJ (US); Ellen Hope Filvaroff, San Francisco, CA (US); Carla Guarinos Marhuenda, Alicante (ES); Bishoy Hanna, Woodbridge, NJ (US); Yu Liu, Brookline, MA (US); Zariana Nikolova, Basel Land (CH); Oriana Esposito, Ticino (CH)

( * ) Notice: Subject to any disclaimer, the term of this patent is extended or adjusted under 35 U.S.C. 154(b) by 0 days.

(21) Appl. No.: 17/680,569

(22) Filed: Feb. 25, 2022

(65) Prior Publication Data

US 2022/0265617 A1  Aug. 25, 2022

Related U.S. Application Data

(60) Provisional application No. 63/297,098, filed on Jan. 6, 2022, provisional application No. 63/232,866, filed on Aug. 13, 2021.

(30) Foreign Application Priority Data

Feb. 25, 2021  (EP) ..................................... 21382163

(51) Int. Cl.
| | |
|---|---|
| *A61K 31/437* | (2006.01) |
| *A61K 31/506* | (2006.01) |
| *A61K 31/519* | (2006.01) |
| *A61K 45/06* | (2006.01) |
| *A61P 35/00* | (2006.01) |

(52) U.S. Cl.
CPC .......... *A61K 31/437* (2013.01); *A61K 31/506* (2013.01); *A61K 31/519* (2013.01); *A61K 45/06* (2013.01); *A61P 35/00* (2018.01)

(58) Field of Classification Search
CPC .. A61K 31/437; A61K 31/506; A61K 31/519; A61K 45/06; A61K 2300/00; A61P 35/00
USPC ....................................................... 514/265
See application file for complete search history.

(56) References Cited

U.S. PATENT DOCUMENTS

| | | | |
|---|---|---|---|
| 7,528,143 B2 | 5/2009 | Noronha et al. | |
| 7,598,257 B2 | 10/2009 | Rodgers et al. | |
| 7,825,246 B2 | 11/2010 | Noronha et al. | |
| 8,138,199 B2 | 3/2012 | Noronha et al. | |
| 8,415,362 B2 | 4/2013 | Rodgers et al. | |
| 8,722,693 B2 | 5/2014 | Rodgers et al. | |
| 8,822,481 B1 | 9/2014 | Rodgers et al. | |
| 8,829,013 B1 | 9/2014 | Rodgers et al. | |
| 9,079,912 B2 | 7/2015 | Rodgers et al. | |
| 9,458,156 B2 | 10/2016 | Norris et al. | |
| 9,814,722 B2 | 11/2017 | Rodgers et al. | |
| 10,016,429 B2 | 7/2018 | Rodgers et al. | |
| 10,391,094 B2 | 8/2019 | Jayan et al. | |

FOREIGN PATENT DOCUMENTS

| | | | | |
|---|---|---|---|---|
| WO | WO-2015100282 A1 * | 7/2015 | ........... | A61K 31/437 |
| WO | WO 2020051572 A1 | 3/2020 | | |
| WO | WO 2020068755 A1 | 4/2020 | | |
| WO | WO 2020167845 A1 | 8/2020 | | |

OTHER PUBLICATIONS

NCT 02419417, "Study of BMS-986158 in Subjects With Select Advanced Cancers (BET)", History of Changes for Study, Version 43, available on Feb. 13, 2018 (Year: 2018).*
Talpaz et al. Leukemia 2021, 35:1-17, published online: Jul. 9, 2020, Fedratinib, a newly approved treatment for patients with myeloproliferative neoplasm-associated myelofibrosis (Year: 2020).*
INREBIC® prescribing information , https://www.accessdata.fda.gov/drugsatfda_docs/label/2019/212327s000lbl.pdf (Year: 2019).*
Hilton et al. Ann. Oncol. 29, 134. doi: 10.1093/annonc/mdy279.399, "Initial results from a phase I/IIa trial evaluating BMS-986158, an inhibitor of the bromodomain and extra-terminal (BET) proteins, in patients (pts) with advanced cancer" (Year: 2018).*
Mullally et al. ,Blood Adv (2020) 4 (8): 1792-1800, "Fedratinib in myelofibrosis" (Year: 2020).*
Jiang et al. , Cancer Cell, vol. 33, Issue 1, Jan. 8, 2018, pp. 3-5, "BET'ing on Dual JAK/BET Inhibition as a Therapeutic Strategy for Myeloproliferative Neoplasms" (Year: 2018).*
Pearson et al. European Journal of Cancer 146 (2021) 115-124; (Year: 2021).*
Sun et al., Front. Pharmacol. 11:621093. Published: Jan. 26, 2021, "Safety and Efficacy of Bromodomain and Extra-Terminal Inhibitors for the Treatment of Hematological Malignancies and Solid Tumors: A Systematic Study of Clinical Trials" (Year: 2021).*
Bewersdorf et al. Cancer Management and Research 2019:11 10777-10790, "Beyond Ruxolitinib: Fedratinib and Other Emergent Treatment Options for Myelofibrosis". (Year: 2019).*

(Continued)

*Primary Examiner* — Jared Barsky
*Assistant Examiner* — Liyuan Mou
(74) *Attorney, Agent, or Firm* — Sterne, Kessler, Goldstein & Fox P.L.L.C.

(57) ABSTRACT

The present disclosure provides methods, pharmaceutical compositions, and kits for treating cancer in patients in need thereof. The methods comprise administering to a patient in need a BET (bromodomain and extra-terminal protein) inhibitor, or a pharmaceutically acceptable salt thereof, alone or in combination with one or more JAK inhibitors. Also provided are medicaments for use in treating cancer.

13 Claims, 36 Drawing Sheets

(56) References Cited

OTHER PUBLICATIONS

NCT04817007, V1, Mar. 24, 2021, "A Study to Assess the Safety and Tolerability of BMS-986158 Alone and in Combination With Either Ruxolitinib or Fedratinib in Participants With Blood Cancer (Myelofibrosis)". (Year: 2021).*

Hilton et al. Cancers, Aug. 23, 2022;14(17):4079. doi: 10.3390/cancers14174079. "BMS-986158, a Small Molecule Inhibitor of the Bromodomain and Extraterminal Domain Proteins, in Patients with Selected Advanced Solid Tumors: Results from a Phase 1/2a Trial". (Year: 2022).*

Ayala et al. Blood (2022) 140 (Supplement 1): 9665-9667, https://doi.org/10.1182/blood-2022-159476, "BMS-986158, a Potent BET Inhibitor, As Monotherapy and in Combination with Ruxolitinib or Fedratinib in Intermediate- or High-Risk Myelofibrosis: First Results from a Phase 1/2 Study". (Year: 2022).*

Lavie et al. Blood 142 (2023) 623-625, https://doi.org/10.1182/blood-2023-179160, "BMS-986158, a potent BET inhibitor, in combination with ruxolitinib or fedratinib in patients with intermediate or high-risk myelofibrosis: updated results from a phase 1/2 study", 65th ASH Annual Meeting and Exposition.*

Ayala et al. HemaSphere 2023;7(S3) S213, BMS-986158, a Potent Bet Inhibitor, as Monotherapy and in Combination With Ruxolitinib or Fedratinib in Intermediate- or High-Risk Myelofibrosis (MF): Results From a Phase 1/2 STUDY (Year: 2023).*

Jiang, Q., et al., "BET'ing on Dual JAK/BET Inhibition as a Therapeutic Strategy for Myeloproliferative Neoplasms," *Cancer Cell*, 33(1):3-5, *Cell Press*, United States (Jan. 2018).

Kleppe, M., et al., "Dual Targeting of Oncogenic Activation and Inflammatory Signaling Increases Therapeutic Efficacy in Myeloproliferative Neoplasms," *Cancer Cell*, 33(1):29-43, Cell Press, United States (Dec. 2017).

Talpaz, M., et al., "Fedratinib, a newly approved treatment for patients with myeloproliferative neoplasm-associated myelofibrosis," *Leukemia*, 35(1):1-17, Nature Publishing Group, (Jul. 2020).

Saenz, D., "Superior Activity of BET Protein Bromodomain Antagonist-Based Combination with JAK Kinase, PIM Kinase or Heat Shock Protein 90 Inhibitor Against Post-MPN-MF SAML Cells," *Blood*, 126(23):1269, American Society of Hematology, United States (Dec. 2015).

Saenz, D., et al., "BET protein bromodomain inhibitor-based combinations are highly active against post-myeloproliferative neoplasm secondary AML cells," *Leukemia*, 31(3):678-687, Nature Publishing Group, United Kingdom (Sep. 2016).

* cited by examiner

BET INHIBITORS AS A TREATMENT FOR MYELOFIBROSIS

CROSS-REFERENCE TO RELATED APPLICATIONS

This application claims the priority benefit of European Application No. 21382163.0, filed Feb. 25, 2021, U.S. Provisional Application No. 63/232,866, filed Aug. 13, 2021, and U.S. Provisional Application No. 63/297,098, filed Jan. 6, 2022, which are each incorporated by reference herein in their entireties.

FIELD

The present disclosure relates to methods of treating myeloproliferative neoplasms. In particular, the present disclosure provides methods for treating various myeloproliferative neoplasms by administering a BET inhibitor alone or in combination with one or more Janus associated kinase (JAK) inhibitors.

BACKGROUND

Myeloproliferative neoplasms (MPNs) are a closely related group of rare, but potentially life-threatening, clonal hematopoietic disorders caused by the overproliferation of bone marrow stem cells. MPNs represent a group of chronic conditions including polycythemia vera (PV), essential thrombocythemia (ET), and primary myelofibrosis (PMF). The main molecular lesion in these diseases is the JAK2 V617F mutation that occurs in over 90% of PV and over 50% of ET and PMF.

Myelofibrosis (MF) is a MPN that is characterized by the expansion of mature myeloid elements and progressive bone marrow (BM) fibrosis. Patients with MF have a poor prognosis with a median time from diagnosis to death of 2.3 years with most patients dying from transformation to acute leukemia, BM failure, congestive heart failure, and other disease outcomes.

Treatment options are limited and often associated with significant morbidity and mortality. Constitutive activation of the Janus Associated Kinase (JAK)/Signal Transducer and Activator of Transcription (STAT) pathway is a hallmark of pathogenesis of MF, which is driven by mutations in JAK2, calreticulin (CALR), or the myeloproliferative leukemia virus (MPL) genes in about 90% of MF cases. This results in downstream increases in gene transcription and expression of genes important for cell cycle regulation, apoptosis, and proteasomal degradation. However, JAK inhibition alone is insufficient for long-term remission and offers modest, if any, disease-modifying effects.

Fedratinib is an oral kinase inhibitor with activity against wild type and mutationally activated JAK2 and FMS-like tyrosine kinase 3 (FLT3). Fedratinib is a JAK2-selective inhibitor with higher inhibitory activity for JAK2 over family members JAK1, JAK3, and TYK2. Abnormal activation of JAK2 is associated with MPNs, including MF and PV. In cell models expressing mutationally active JAK2V617F or FLT3ITD, fedratinib reduced phosphorylation of STAT3 and STAT5 proteins, inhibited cell proliferation, and induced apoptotic cell death. In mouse models of JAK2V617F-driven myeloproliferative disease, fedratinib blocked phosphorylation of STAT3/5, and improved survival, WBC counts, hematocrit, splenomegaly, and fibrosis.

Recently, BET proteins have emerged as a group of epigenetic transcriptional co-regulators. They belong to a family of chromatin readers—BRD2, BRD3, BRD4 and BRDT-recognizing acetylated lysines in histones and other proteins. Each protein possesses two highly conserved bromodomains. Their main function is to recruit members of the pTEF-b complex to promoters to support transcriptional elongation, and their functional importance is underscored by their links to cancer when they become dysregulated. Small molecule inhibitors of BET proteins have demonstrated activity in pre-clinical models of mixed lineage leukemia (MLL) fusion protein-driven leukemias and are under investigation in other malignancies.

The inhibition of both BET protein-mediated cellular pathways and the JAK-STAT pathway could reduce inflammation and reverse or reduce the fibrosis associated with myelofibrosis, and could provide more effective therapy for the disease than either agent alone.

BRIEF SUMMARY

In a first aspect, the present disclosure provides a method of treating a hematological malignancy in a subject in need thereof, the method comprising administering to the subject:
a compound of formula (I):

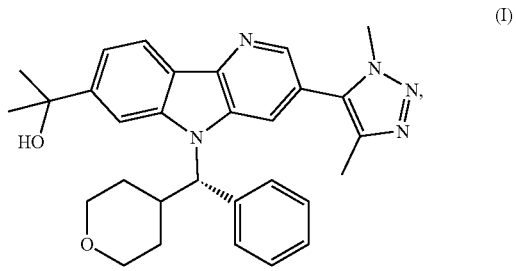 [SMILES: Cc1nnn(C)c1-c1cnc2c3ccc(C(C)(C)O)cc3n([C@H](c3ccccc3)C3CCOCC3)c2c1]

or a pharmaceutically acceptable salt thereof; and
a compound of formula (II):

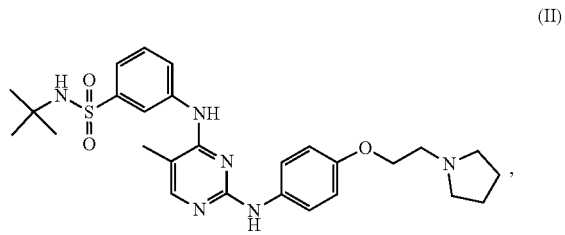 [SMILES: Cc1cnc(Nc2ccc(OCCN3CCCC3)cc2)nc1Nc1cccc(S(=O)(=O)NC(C)(C)C)c1]

or a pharmaceutically acceptable salt and/or solvate thereof.

In some aspects, the compound of formula (I), or the pharmaceutically acceptable salt thereof, and the compound of formula (II), or the pharmaceutically acceptable salt and/or solvate thereof, are administered concurrently.

In some aspects, the compound of formula (I), or the pharmaceutically acceptable salt thereof, and the compound of formula (II), or the pharmaceutically acceptable salt and/or solvate thereof, are administered sequentially.

In some aspects, the administration of the compound of formula (I), or the pharmaceutically acceptable salt thereof, and the compound of formula (II), or the pharmaceutically acceptable salt and/or solvate thereof, provides a synergistic effect.

In some aspects, the compound of formula (I), or the pharmaceutically acceptable salt thereof, and the compound of formula (II), or the pharmaceutically acceptable salt and/or solvate thereof, are each administered orally.

In some aspects, the compound of formula (I), or the pharmaceutically acceptable salt thereof, is administered at a dose of from about 0.1 mg to about 10 mg.

In some aspects, the compound of formula (I), or the pharmaceutically acceptable salt thereof, is administered at a dose of from about 0.25 mg to about 4.5 mg.

In some aspects, the compound of formula (I), or the pharmaceutically acceptable salt thereof, is administered at a dose of 0.25 mg, 0.5 mg, 0.75 mg, 1.0 mg, 1.25 mg, 1.5 mg, or 2.0 mg.

In some aspects, the compound of formula (II), or the pharmaceutically acceptable salt and/or solvate thereof, is administered in an amount of from about 50 mg to about 500 mg.

In some aspects, the compound of formula (II), or the pharmaceutically acceptable salt and/or solvate thereof, is administered in an amount of about 400 mg.

In some aspects, the compound of formula (I), or the pharmaceutically acceptable salt thereof, is administered once daily.

In some aspects, the compound of formula (II), or the pharmaceutically acceptable salt thereof, is administered once daily.

In some aspects, the compound of formula (II) or a pharmaceutically acceptable salt and/or hydrate thereof is administered.

In some aspects, the dihydrochloride monohydrate of the compound of formula (II) is administered.

In some aspects, the present disclosure provides a method of treating a hematological malignancy in a subject in need thereof, the method comprising administering to the subject:

a compound of formula (I):

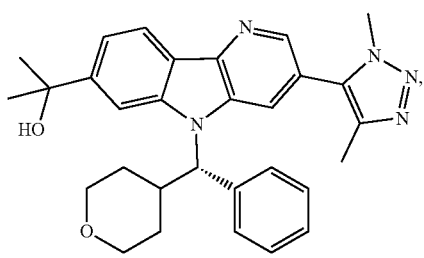

or a pharmaceutically acceptable salt thereof; and
a compound of formula (III):

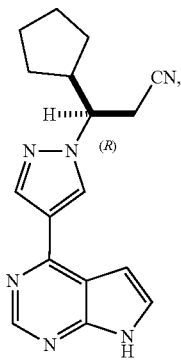

or a pharmaceutically acceptable salt thereof.

In some aspects, the compound of formula (I), or the pharmaceutically acceptable salt thereof, and the compound of formula (III), or the pharmaceutically acceptable salt thereof, are administered concurrently.

In some aspects, the compound of formula (I), or the pharmaceutically acceptable salt thereof, and the compound of formula (III), or the pharmaceutically acceptable salt thereof, are administered sequentially.

In some aspects, the administration of the compound of formula (I), or the pharmaceutically acceptable salt thereof, and the compound of formula (III), or the pharmaceutically acceptable salt thereof, provides a synergistic effect.

In some aspects, the compound of formula (I), or the pharmaceutically acceptable salt thereof, and the compound of formula (III), or the pharmaceutically acceptable salt thereof, are each administered orally.

In some aspects, the compound of formula (I), or the pharmaceutically acceptable salt thereof, is administered at a dose of from about 0.1 mg to about 10 mg.

In some aspects, the compound of formula (I), or the pharmaceutically acceptable salt thereof, is administered at a dose of from about 0.25 mg to about 4.5 mg.

In some aspects, the compound of formula (I), or the pharmaceutically acceptable salt thereof, is administered at a dose of 1.25 mg, 2.0 mg, 3.0 mg, 4.0 mg, or 4.5 mg.

In some aspects, the compound of formula (III), or the pharmaceutically acceptable salt thereof, is administered in an amount of from about 5 mg to about 50 mg.

In some aspects, the compound of formula (III), or the pharmaceutically acceptable salt thereof, is administered in an amount of about 15 mg.

In some aspects, the dose of the compound of formula (III), or the pharmaceutically acceptable salt thereof, is administered twice a day.

In some aspects, the dose of the compound of formula (I), or the pharmaceutically acceptable salt thereof, is administered twice a day.

In some aspects, the dose of the compound of formula (I), or the pharmaceutically acceptable salt thereof, is administered twice a day.

In some aspects, the phosphoric acid salt of the compound of formula (III) is administered.

In some aspects, the present disclosure provides a method of treating a hematological malignancy in a subject in need thereof, the method comprising administering to the subject a compound of formula (I):

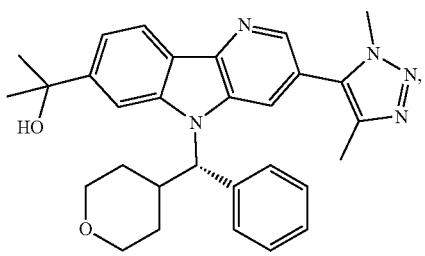

(I)

or a pharmaceutically acceptable salt thereof.

In some aspects, the compound of formula (I), or the pharmaceutically acceptable salt thereof, is administered at a dose of from about 0.1 mg to about 10 mg; preferably at a dose of from about 0.25 mg to about 4.5 mg; more preferably at a dose of 0.25 mg, 0.5 mg, 0.75 mg, 1.0 mg, 1.25 mg, 1.5 mg, or 2.0 mg.

In some aspects, the hematological malignancy is a myeloproliferative neoplasm.

In some aspects, the myeloproliferative neoplasm is myelofibrosis.

In some aspects, the myelofibrosis is relapsed/refractory myelofibrosis.

In some aspects, the subject is treatment naïve.

In some aspects, the subject has previously been treated with ruxolitinib.

In some aspects, myelofibrosis is primary myelofibrosis.

In some aspects, the primary myelofibrosis is selected from intermediate risk primary myelofibrosis and high risk primary myelofibrosis.

In some aspects, the myelofibrosis is secondary myelofibrosis.

In some aspects, the myelofibrosis is post-essential thrombocythemia myelofibrosis.

In some aspects, the myelofibrosis is post-polycythemia vera myelofibrosis.

In some aspects, the myeloproliferative neoplasm is polycythemia vera.

In some aspects, the myeloproliferative neoplasm is essential thrombocythemia.

In some aspects, the hematological malignancy is acute myeloid leukemia (AML).

In some aspects, the present disclosure provides a composition comprising a compound of formula (I):

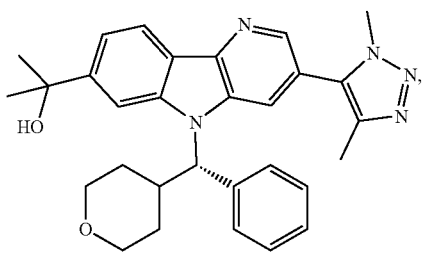

(I)

or a pharmaceutically acceptable salt thereof; and
a compound of formula (II):

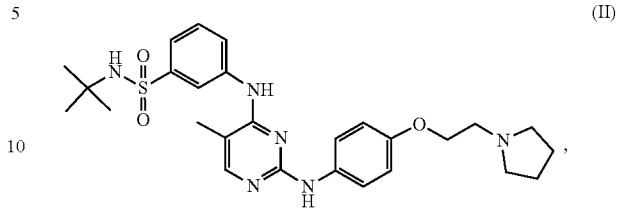

(II)

or a pharmaceutically acceptable salt and/or solvate (e.g., a hydrate) thereof.

In some aspects, the present disclosure provides a composition comprising a compound of formula (I):

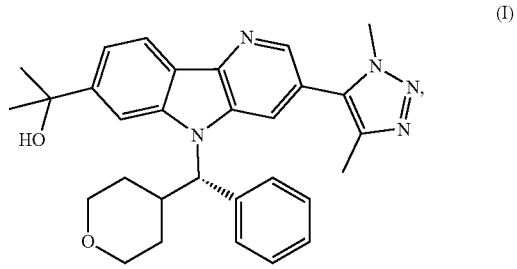 [SMILES: Cc1nnn(C)c1-c1cnc2c3ccc(C(C)(C)O)cc3n([C@H](c3ccccc3)C3CCOCC3)c2c1]

(I)

or a pharmaceutically acceptable salt thereof; and

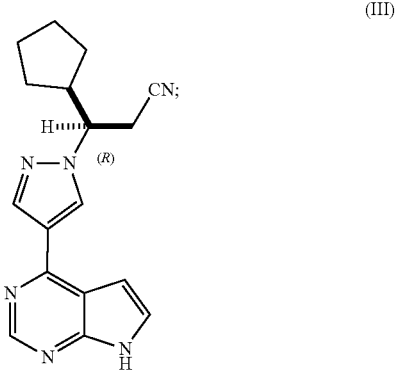

(III)

or a pharmaceutically acceptable salt thereof.

In some aspects, the compositions are used for the manufacture of a medicament for treatment of a hematological malignancy.

In some aspects, the compositions further comprise a pharmaceutically acceptable carrier.

In some aspects, the compositions are used in the treatment of a hematological malignancy.

DETAILED DESCRIPTION

Figure 1A:
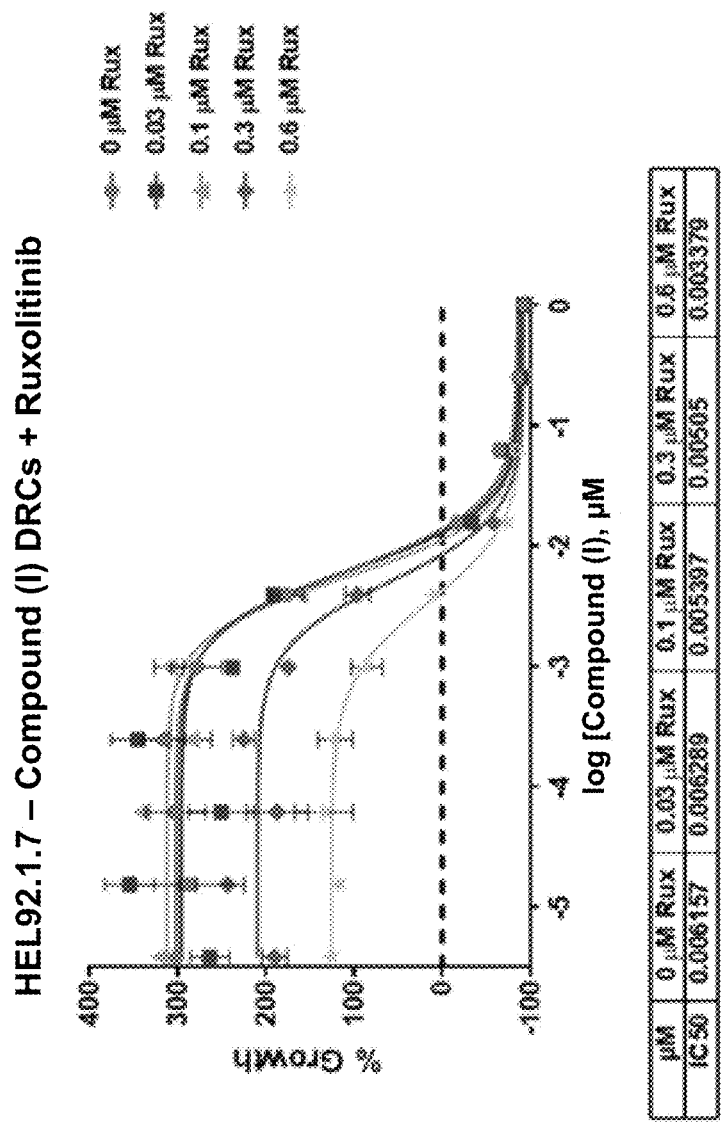
FIG. 1A shows a plot of Compound (I) viability dose-response curves with ruxolitinib (Rux) in HEL92.1.7 cells with IC50 values.

Provided are methods and composition for the use of a Bromodomain and Extra-Terminal motif (BET) protein inhibitor alone and in combination with a Janus associated kinase (JAK) inhibitor for the treatment of a disease in a subject, wherein the JAK inhibitor is selected from fedratinib (formula (II)) and ruxolitinib (formula (III)). Combinations of the present disclosure are useful for inhibiting a BET protein and/or a JAK protein and for treating diseases, disorders, or conditions, e.g., cancer specifically hematological malignancies that are responsive to inhibition of a BET protein and/or a JAK protein.

Advantageously, the combination of a BET inhibitor and a JAK inhibitor provide a synergistic effect.

In some aspects, the BET inhibitor and the JAK inhibitor are administered in therapeutically effective amounts sufficient to produce a therapeutic effect. The therapeutic effect of the administration of the combination therapy includes, but is not limited to, a delay, reduction, or prevention of re-growth of a hematological malignancy, spleen volume response, increase in hemoglobin, and transfusion independence.

Definitions

In order that the present description can be more readily understood, certain terms are first defined. Additional definitions are set forth throughout the detailed description.

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein.

As used herein, unless specifically indicated otherwise, the word "or" is used in the inclusive sense of "and/or" and not the exclusive sense of "either/or."

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

As used herein, the term "effective amount" or "therapeutically effective amount" refers to an amount of a compound, or combination of one or more compounds that, when administered (either sequentially or simultaneously) elicits the desired biological or medicinal response, e.g., either destroys the target cancer cells, slows or arrests the progression of the cancer in a patient, or otherwise lessens disease symptom severity. The therapeutically effective amount may vary depending upon the intended application (in vitro or in vivo), or the patient and disease condition being treated, e.g., the weight and age of the patient, the severity of the disease condition, the manner of administration and the like, which may readily be determined by one skilled in the art. The term also applies to a dose that will induce a particular response in target cells, e.g., reduction of cell proliferation and/or cell migration. For example, in some aspects, the "therapeutically effective amount" as used herein refers to the amount of a compound of formula (I), or a pharmaceutically acceptable salt thereof, and the amount of a JAK inhibitor that, when administered separately or in combination, have a beneficial effect. In some aspects, the combined effect is additive. In some aspects, the combined effect is synergistic. Further, it will be recognized by one skilled in the art that in the case of combination therapy, the amount of the compound of formula (I), or a pharmaceutically acceptable salt thereof, and/or the amount of the JAK inhibitor can be used in a "sub-therapeutic amount", i.e., less than the therapeutically effective amounts of each compound when used alone.

The term "about" refers to approximately, in the region of, roughly, or around. When the term "about" is used in conjunction with a number or a numerical range, it means that the number or numerical range referred to is an approximation within experimental variability (or within statistical experimental error), and thus the number or numerical range may vary from, for example, between 1% and 15% of the stated number or numerical range. In general, the term "about" is used herein to modify a numerical value above and below the stated value by a variance of 10%.

As used herein, "patient" generally means a mammal (e.g., a human) who has been diagnosed with, exhibits symptoms of, or is otherwise believed to be afflicted with a disease, disorder, or condition (such as a malignancy). In some aspects, the patient is an adult patient (e.g., an adult human).

The term "malignancy" refers to a hematological malignancy and a cancer. The hematological malignancy is a cancer of a cell of the hematological/hematopoietic system. A cancer, in general, is a cancer of a non-hematological/non-hematopoietic system including a solid cancer.

The term "combination administration," "administered in combination," and "administering a combination" refers to administering of more than one pharmaceutically active ingredients (including, but not limited to, the compound of formula (I), or a pharmaceutically acceptable salt thereof, and a Janus associated kinase inhibitor as disclosed herein) to a patient. Combination administration may refer to simultaneous administration or may refer to sequential administration of the compound of formula (I), or a pharmaceutically acceptable salt thereof, and a Janus associated kinase inhibitor as disclosed herein.

The terms "simultaneous" and "simultaneously" refer to the administration of the compound of formula (I), or a pharmaceutically acceptable salt thereof, and a Janus associated kinase inhibitor as disclosed herein, to a patient at the same time, or at two different time points that are separated by no more than 2 hours. The simultaneous administration of the compound of formula (I), or a pharmaceutically acceptable salt thereof, and a Janus associated kinase inhibitor can be in a single dosage form or in separate dosage forms.

The terms "sequential" and "sequentially" refer to the administration of the compound of formula (I), or a pharmaceutically acceptable salt thereof, and a Janus associated kinase inhibitor, as disclosed herein, to a patient at two different time points that are separated by more than 2 hours, e.g., about 3 hours, about 4 hours, about 5 hours, about 8 hours, about 12 hours, 1 day, 2 days, 3 days, 4 days, 5 days, 6 days, 7 days or even longer.

The term "intermission" refers to a period that is subsequent to the administration of one or more particular pharmaceutically active ingredients to a patient in an intermittent regimen. Intermission refers to a rest period wherein a particular pharmaceutically active ingredient is not administered for at least one day.

The term "synergistic effect" refers to a situation where the combination of two or more agents produces a greater effect than the sum of the effects of each of the individual agents. The term encompasses not only a reduction in symptoms of the disorder to be treated, but also an improved side effect profile, improved tolerability, improved patient compliance, improved efficacy, or any other improved clinical outcome.

A determination of a synergistic interaction between a BET inhibitor and a JAK inhibitor can be based on the results obtained from the assays described herein. For example, combination effects can be evaluated using the Bliss independence model. Bliss scores quantify degree of potentiation from single agents, and a Bliss score >0 suggests greater than simple additivity. In some aspects, a Bliss score greater than 10 indicates strong synergy. In other aspects, a score of 6 or greater indicates synergy. In some aspects, the Bliss score is about 6, about 7, about 8, about 9, about 10, about 11, about 12, about 13, about 14, about 15, about 16, about 17, about 18, about 19, about 20 or about 25.

As used herein, the illustrative terms "include", "such as", "for example" and the like (and variations thereof, e.g., "includes" and "including", "examples"), unless otherwise specified, are intended to be non-limiting. That is, unless explicitly stated otherwise, such terms are intended to imply "but not limited to", e.g., "including" means including but not limited to.

Unless otherwise stated, structures depicted herein are meant to include chemical entities that differ only in the presence of one or more isotopically enriched atoms. For example, chemical entities having the present structure except for the replacement of a hydrogen atom by a deuterium or tritium, or the replacement of a carbon atom by a $^{13}$C— or $^{14}$C-enriched carbon are within the scope of the disclosure.

Unless stereochemical configuration is denoted, structures depicted herein are meant to include all stereochemical forms of the structure, i.e., the R and S configurations for each asymmetric center. Therefore, unless otherwise indicated, single stereochemical isomers as well as enantiomeric, racemic and diastereomeric mixtures of the present chemical entities are within the scope of the disclosure. When a stereochemical configuration is denoted for a compound, the diastereoisomeric or enantiomeric excess of the compound is at least 99.0%, 99.5%, 99.6%, 99.7%, 99.8% or 99.9%.

As used herein, the recitation of a numerical range for a variable is intended to convey that the disclosure can be practiced with the variable equal to any of the values within that range. Thus, for a variable which is inherently discrete, the variable can be equal to any integer value within the numerical range, including the end-points of the range. Similarly, for a variable which is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values >0 and <2 if the variable is inherently continuous.

All of the references cited herein are incorporated herein by reference in their entireties.

BET Inhibitors

The present disclosure provides a combination treatment for patients with a malignancy including a hematological malignancy. The combination treatment includes, inter alia, administering to a subject in need thereof a therapeutically effective amount of at least one BET inhibitor.

Bromodomain and Extra-Terminal Domain Protein (BET) Inhibitors

In some aspects, the BET inhibitor is a compound of formula (I) (also referred to as Compound (I)):

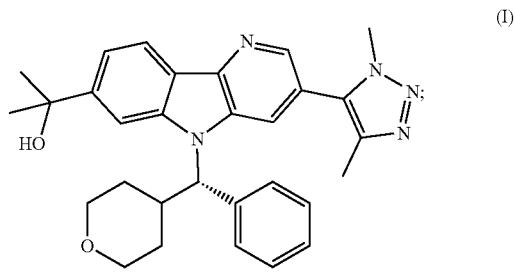 [SMILES: Cc1nnn(C)c1-c1cnc2c3ccc(C(C)(C)O)cc3n([C@H](c3ccccc3)C3CCOCC3)c2c1]

(I)

or a pharmaceutically acceptable salt thereof. The compound of formula (I) can be prepared as described in U.S. Pat. No. 9,458,156, which is incorporated by reference in its entirety. In some aspects, the BET inhibitor is CPI-0610.

Janus Associated Kinase (JAK) Inhibitors

In some aspects, the present disclosure provides a combination treatment that includes, inter alia, administering to a subject in need thereof a therapeutically effective amount of at least one Janus associated kinase (JAK) inhibitor (e.g., ruxolitinib, fedratinib, tofacitinib, oclacitinib, baricitinib, peficitinib, or upadacitinib).

In some aspects, the JAK inhibitor is a JAK1/2 inhibitor. In some aspects, the JAK1/2 inhibitor is ruxolitinib, which has the chemical structure shown below:

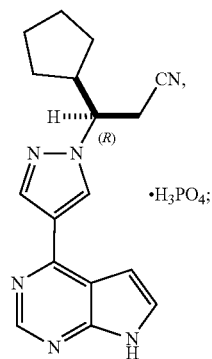

and is described in U.S. Pat. Nos. 7,598,257; 8,415,362; 8,722,693; 8,822,481; 8,829,013; 9,079,912; 9,814,722; and 10,016,429. Ruxolitinib phosphate is a kinase inhibitor with the chemical name (R)-3-(4-(7H-pyrrolo[2,3d]pyrimidin-4-yl)-1H-pyrazol-1-yl)-3-cyclopentylpropanenitrile phosphate.

In some aspects, the JAK inhibitor is a JAK2 specific inhibitor. In some aspects, the JAK2 inhibitor is fedratinib, which has the chemical structure shown below:

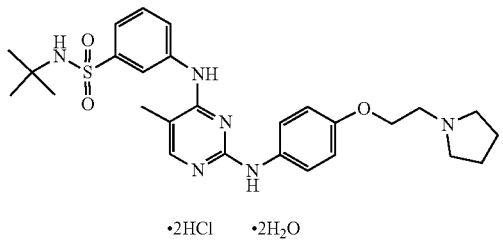 [SMILES: Cc1cnc(Nc2ccc(OCCN3CCCC3)cc2)nc1Nc1cccc(S(=O)(=O)NC(C)(C)C)c1]

·2HCl  ·2H$_2$O and has been previously described, e.g., in U.S. Pat. Nos. 7,528,143; 7,825,246; 8,138,199; and 10,391,094; and in PCT Application Publication Nos. WO 2020/167845 and WO 2020/068755, which are each hereby incorporated by reference in their entireties.

Methods of Treating Cancer

In some aspects, the present disclosure relates to a method of treating a malignancy in a patient by administering to a patient in need of said treating a combination of a BET inhibitor, or pharmaceutically acceptable salt thereof, alone or in combination with a JAK inhibitor, or a pharmaceutically acceptable salt and/or solvate (e.g., a hydrate) thereof.

In some aspects, the present disclosure relates to the use of a BET inhibitor, or pharmaceutically acceptable salt thereof, in combination with a JAK inhibitor, or a pharmaceutically acceptable salt and/or solvate (e.g., a hydrate) thereof for the treatment of a malignancy in a patient.

In some aspects, the present disclosure relates to a composition comprising a BET inhibitor for use in treating a malignancy in a patient, wherein the patient is also treated with a JAK inhibitor. In some aspects, the disclosure relates to a composition comprising a BET inhibitor for use in treating cancer in a patient, wherein the BET inhibitor is in combination with the JAK inhibitor. In some aspects, the BET inhibitor can be administered simultaneously or sequentially with the JAK inhibitor.

In some aspects, the present disclosure relates to methods of treating a malignancy comprising administering to a patient in need of such treatment, the compound of formula (I), or a pharmaceutically acceptable salt thereof, and a JAK inhibitor, or a pharmaceutically acceptable salt thereof, as a co-formulation or separate formulation, wherein the administration of the formulations is simultaneous, sequential, or in alternation.

In some aspects, the present disclosure relates to methods of treating cancer comprising administering to a patient in need of such treatment, a therapeutically effective amount of a combination of a BET inhibitor alone or in combination with a JAK inhibitor. In some aspects, the combination of the disclosure is less toxic than the BET inhibitor alone. In some aspects, the combination of the disclosure is less toxic than the JAK inhibitor alone.

In some aspects, the present disclosure relates to a method of treating cancer by administering to a patient a combination of the compound of formula (I), or pharmaceutically acceptable salt thereof, and a JAK inhibitor, or a pharmaceutically acceptable salt thereof.

In another aspect, the present disclosure relates to the use of the compound of formula (I), or a pharmaceutically acceptable salt thereof, in combination with a JAK inhibitor, or a pharmaceutically acceptable salt thereof, for the treatment of cancer.

In some aspects, the JAK inhibitor is co-administered with thiamine.

In some aspects, the present disclosure relates to a method of treating a disorder, wherein the disorder is a hematological malignancy. In some aspects, the hematological malignancy is acute myeloid leukemia (AML). In some aspects, the hematological malignancy is a myeloproliferative neoplasm. In some aspects, the myeloproliferative neoplasm is myelofibrosis. In some aspects, the myelofibrosis is primary myelofibrosis. In some aspects, the primary myelofibrosis is selected from intermediate risk primary myelofibrosis and high risk primary myelofibrosis. In some aspects, the myelofibrosis is secondary myelofibrosis. In some aspects, the myelofibrosis is post-essential thrombocythemia myelofibrosis. In some aspects, the myelofibrosis is post-polycythemia vera myelofibrosis.

In some aspects, the myeloproliferative neoplasm is polycythemia vera. In some aspects, the myeloproliferative neoplasm is polycythemia vera in adults who have had an inadequate response to or are intolerant of hydroxyurea. In some aspects, the myeloproliferative neoplasm is intermediate or high-risk myelofibrosis, including primary myelofibrosis, post-polycythemia vera myelofibrosis and post-essential thrombocythemia myelofibrosis in adults. In some aspects, the myeloproliferative neoplasm is intermediate-2 or high-risk primary or secondary (post-polycythemia vera or post-essential thrombocythemia) myelofibrosis (MF) in adult patients. In some aspects, the myeloproliferative neoplasm is essential thrombocythemia.

Other non-limiting examples of hematologic malignancies include chronic myelogenous leukemia (CML), including accelerated CML and CML blast phase (CML-BP); acute lymphoblastic leukemia (ALL); chronic lymphocytic leukemia (CLL); Hodgkin's lymphoma (HL), including classical Hodgkin lymphoma; non-Hodgkin's lymphoma (NHL), including B-cell lymphoma, T-cell lymphoma, follicular lymphoma (FL), marginal zone lymphoma (MZL), mantle cell lymphoma (MCL), diffuse large B-cell lymphoma (DLBCL), primary mediastinal large B-cell lymphoma, and Burkitt lymphoma; multiple myeloma (MM); amyloidosis; Waldenstrom's macroglobulinemia; myelodysplastic syndromes (MDS), including refractory anemia (RA), refractory anemia with ringed sideroblasts (RARS), (refractory anemia with excess blasts (RAEB), and RAEB in transformation (RAEB-T); and myeloproliferative syndromes. In some aspects, the cancer is chronic lymphocytic leukemia (CLL), Hodgkin's lymphoma, or non-Hodgkin's lymphoma including follicular lymphoma (FL), marginal zone lymphoma (MZL), mantle cell lymphoma (MCL), Diffuse large B-cell lymphoma (DLBCL) and Burkitt lymphoma.

In some aspects, the hematological malignancy is relapsed. In some aspects, the hematological relapsed malignancy is a malignancy that has returned after a period of time in which no hematological malignancy could be detected.

In some aspects, the hematological malignancy is refractory. In some aspects, the refractory hematological malignancy does not respond to treatment; it is also known as resistant hematological malignancy. In some aspects, the malignancy is resistant to ruxolitinib.

In some aspects, the malignancy is a hematological malignancy and has not previously been treated.

In some aspects, the patient has an advanced hematological malignancy for which at least one prior treatment regimen has failed.

Medicament

In some aspects, the present disclosure relates to a medicament for use in treating cancer in a patient in need of such treatment. In some aspects, the medicament comprises a BET inhibitor. In some aspects, the medicament comprises a BET inhibitor and a JAK inhibitor, and is in single dosage form or in separate dosage forms.

In some aspects, the medicaments, as described herein, can include a combination of a BET inhibitor, a JAK inhibitor, and optionally one or more additional therapeutic agents.

In some aspects, the present disclosure relates to the use of a BET inhibitor in the manufacture of a medicament for treating cancer, wherein the BET inhibitor is administered alone or in combination with a JAK inhibitor. In some aspects, wherein the BET inhibitor is administered in combination with a JAK inhibitor, the medicament is in single dosage form or in separate dosage forms.

In some aspects, the present disclosure relates to the use of a BET inhibitor for the manufacture of a medicament in treating cancer in a patient, wherein the patient is also treated with a JAK inhibitor. In some aspects, the BET inhibitor can be administered simultaneously or sequentially with the JAK inhibitor. In some aspects, the present disclosure relates to the use of a BET inhibitor for the manufacture of a medicament in treating cancer in a patient, wherein the BET inhibitor is in combination with a JAK inhibitor. In some aspects, the BET inhibitor is in the same composition as the JAK inhibitor. In some aspects, the BET inhibitor is in a separate composition as the JAK inhibitor. In some aspects, the BET inhibitor is in the same composition as the JAK inhibitor. In some aspects, the BET inhibitor is in a separate composition as the JAK inhibitor.

In some aspects, the present disclosure relates to the use of a compound of formula (I), named the compound of formula (I), or a pharmaceutically acceptable salt thereof in combination with a JAK inhibitor in the manufacture of a medicament for use in treating cancer. In some aspects, the present disclosure relates to the use of the compound of formula (I), or a pharmaceutically acceptable salt thereof in combination with a JAK inhibitor in the manufacture of a medicament for use in treating cancer.

In another aspect, the present disclosure relates to the use of the compound of formula (I), or a pharmaceutically acceptable salt thereof, in the manufacture of a medicament for treating cancer, wherein the compound of formula (I), or a pharmaceutically acceptable salt thereof, is administered alone or with a JAK inhibitor.

In another aspect, the present disclosure relates to the compound of formula (I), or a pharmaceutically acceptable salt thereof, for use as a medicament in combination with a JAK inhibitor, wherein the compound of formula (I) and the JAK inhibitor can be administered simultaneously or sequentially.

In another aspect, the present disclosure relates to the use of a compound of formula (I), or a pharmaceutically acceptable salt thereof, and a JAK inhibitor, in the manufacture of a medicament for the treatment of cancer in a subject. In some aspects, the present disclosure relates to the use of the compound of formula (I), or a pharmaceutically acceptable salt thereof, and a JAK inhibitor, in the manufacture of a medicament for the treatment of cancer in a subject, wherein the compound of formula (I) is formulated to be administrable simultaneously or sequentially to the subject. In some aspects, the present disclosure relates to the use of the compound of formula (I), or a pharmaceutically acceptable salt thereof, and a JAK inhibitor, in the manufacture of a medicament for the treatment of cancer in a subject, wherein the compound of formula (I) and the JAK inhibitor are formulated to be administrable simultaneously or sequentially to the subject.

In some aspects, the JAK inhibitor is fedratinib or ruxolitinib.

Pharmaceutical Combination Compositions

Combinations of the disclosure can be administered to a mammal in the form of a raw chemicals without any other components present, or combinations of the disclosure can also be administered to a mammal as part of a pharmaceutical composition containing the compound combined with a suitable pharmaceutically acceptable carrier (see, for example, Gennaro, Remington: The Science and Practice of Pharmacy with Facts and Comparisons: Drugfacts Plus, 20th ed. (2003); Ansel et al., Pharmaceutical Dosage Forms and Drug Delivery Systems, 7th ed., Lippencott Williams and Wilkins (2004); Kibbe et al., Handbook of Pharmaceutical Excipients, 3rd ed., Pharmaceutical Press (2000)). Such a carrier can be selected from pharmaceutically acceptable excipients and auxiliaries. The term "pharmaceutically acceptable carrier" or "pharmaceutically acceptable vehicle" encompasses any of the standard pharmaceutical carriers, solvents, surfactants, or vehicles. Standard pharmaceutical carriers and their formulations are described in Remington's Pharmaceutical Sciences, Mack Publishing Co., Easton, PA, 19th ed. 1995.

A pharmaceutical combination composition of the present disclosure can be prepared as liquid suspensions or solutions using a liquid, such as an oil, water, an alcohol, and combinations of these.

The pharmaceutical combination compositions to be used for in vivo administration can be sterile. This is readily accomplished by filtration through, e.g., sterile filtration membranes.

Pharmaceutical combination compositions within the scope of the present disclosure include all compositions where a BET inhibitor and a JAK inhibitor of the disclosure are combined with one or more pharmaceutically acceptable carriers. In one aspect, the BET inhibitor and JAK inhibitor of the disclosure are present in the composition in an amount that is effective to achieve its intended therapeutic purpose.

A pharmaceutical combination composition of the present disclosure can be administered to any patient that may experience the beneficial effects of a combination of the disclosure. Foremost among such patients are mammals, e.g., humans and companion animals, although the disclosure is not intended to be so limited. In one aspect, the patient is a human. In one aspect, the human is an adult. In another aspect, a pharmaceutical combination composition of the present disclosure can be administered to a patient having JAK inhibitor resistant or refractory cancer. In another aspect, a pharmaceutical combination composition of the present disclosure can be administered to a patient having JAK inhibitor resistant or refractory cancer.

In another aspect, the present disclosure provides kits that comprise a combination of the disclosure packaged in a manner that facilitates their use to practice methods of the present disclosure. In one aspect, the kit includes a BET inhibitor and a JAK inhibitor of the disclosure packaged in a container, such as a sealed bottle or vessel, with a label affixed to the container or included in the kit that describes use of the compounds to practice the methods of the disclosure. In one aspect, the combination composition is packaged in a unit dosage form. The kit further can include a device suitable for administering the combination composition JAK to the intended route of administration. In some aspects, the present disclosure provides a kit that comprises a BET inhibitor and a JAK inhibitor of the disclosure, or a pharmaceutically acceptable salt or solvate thereof, and instructions for administering the compounds, or pharmaceutically acceptable salts thereof, to a patient having cancer.

In some aspects, the present disclosure provides a pharmaceutical combination composition comprising a BET inhibitor and a JAK inhibitor of the disclosure, or a pharmaceutically acceptable salt thereof, and a pharmaceutically acceptable carrier.

In some aspects, the present disclosure provides a pharmaceutical combination composition comprising a BET inhibitor and a JAK inhibitor of the disclosure, or a pharmaceutically acceptable salt thereof, and a pharmaceutically acceptable carrier, wherein the combination binds to a protein encoded by the BET gene and/or a JAK gene.

In some aspects, the present disclosure provides a pharmaceutical combination composition comprising a BET inhibitor and JAK inhibitor of the disclosure, or a pharmaceutically acceptable salt thereof, and a pharmaceutically acceptable carrier, wherein the pharmaceutical composition is for use in treating cancer.

In some aspects, the present disclosure provides a pharmaceutical combination composition comprising a BET inhibitor and a JAK inhibitor of the disclosure, or a pharmaceutically acceptable salt thereof, and a pharmaceutically acceptable carrier, wherein the pharmaceutical composition is for the manufacture of a medicament for treatment of cancer.

Administration of the Combination

The compound of formula (I), or a pharmaceutically acceptable salt thereof, can be administered in combination with the JAK inhibitor, in a single dosage form or as a separate dosage forms. In some aspects, when administered as a separate dosage form, the JAK inhibitor can be administered prior to, at the same time as, or following administration of the compound of formula (I), or a pharmaceutically acceptable salt thereof. In some aspects, when administered as a separate dosage form, one or more doses of the compound of formula (I), or a pharmaceutically acceptable salt thereof, can be administered prior to the JAK inhibitor. In some aspects, the JAK inhibitor is administered prior to the administration of the compound of formula (I), or a pharmaceutically acceptable salt thereof. As used herein, the administration in "combination" of the compound of formula (I), or a pharmaceutically acceptable salt thereof, a JAK inhibitor refers not only to simultaneous or sequential administration of the agents, but also to the administration of the agents during a single treatment cycle, as understood by one skilled in the art. When the compound of formula (I), or a pharmaceutically acceptable salt thereof is administered in combination with the JAK inhibitor, a therapeutically effective amount of the combination is administered.

The BET inhibitor can be administered by any method known to one skilled in the art. For example, in some aspects, the BET inhibitor can be administered in the form of a pharmaceutical composition of the BET inhibitor and a pharmaceutically acceptable carrier, such as those described herein. In some aspects, the pharmaceutical composition is suitable for oral administration. In some aspects, the pharmaceutical composition is a tablet that is suitable for oral administration.

In some aspects, the pharmaceutical composition comprising the BET inhibitor is formulated as a capsule suitable for oral administration. In some aspects, the capsule is a hard gelatin capsule. In some aspects, the pharmaceutical composition comprises polyethylene glycol. In some aspects, the pharmaceutical composition comprises PEG 1450. In some aspects, the concentration of BET inhibitor in PEG 1450 is between about 1 mg/mL and about 10 mg/mL. In some aspects, the concentration of BET inhibitor in PEG 1450 is between about 1 mg/mL and about 6 mg/mL. In some aspects, the concentration of BET inhibitor in PEG 1450 is about 1.25 mg/mL/ In some aspects, the concentration of BET inhibitor in PEG 1450 is about 6 mg/mL.

In some other aspects, the pharmaceutical composition is a liquid dosage form suitable for oral administration. In some aspects, the pharmaceutical composition is suitable for parenteral administration. In some aspects, the pharmaceutical composition is suitable for intravenous administration. In some aspects, the pharmaceutical composition is suitable for intravenous infusion. In some aspects, the pharmaceutical composition is suitable for injection. In some aspects, the pharmaceutical composition is suitable for intravenous injection. In some aspects, the pharmaceutical composition is suitable for subcutaneous injection. In some aspects, these compositions optionally further comprise one or more additional therapeutic agents.

The JAK inhibitor can be administered by any method known to one skilled in the art. In some aspects, the JAK inhibitor is administered intravenously (i.v.). In some aspects, the JAK inhibitor is administered subcutaneously (s.c.). In some aspects, the JAK inhibitor is administered orally. For example, the JAK inhibitor can be administered in the form of a second composition, in some aspects, a pharmaceutical composition of the JAK inhibitor and a pharmaceutically acceptable carrier, such as those described herein. In some aspects, the pharmaceutical composition is suitable for oral administration. In some aspects, the pharmaceutical composition is a tablet or a capsule that is suitable for oral administration. In some other aspects, the pharmaceutical composition is a liquid dosage form suitable for oral administration. In some aspects, these compositions optionally further comprise one or more additional therapeutic agents.

In some aspects, the JAK inhibitor can be administered orally, parenterally, by inhalation spray, topically, rectally, nasally, buccally, vaginally or via an implanted reservoir. The term "parenteral" as used herein includes subcutaneous, intravenous, intraperitoneal, intramuscular, intra articular, intra synovial, intrasternal, intrathecal, intrahepatic, intralesional and intracranial injection or infusion techniques. In some aspects, the JAK inhibitor is administered orally, intravenously or subcutaneously. In some aspects, the JAK inhibitor is administered orally. In some aspects, the JAK inhibitor is administered intravenously. In some aspects, the intravenous administration can be intravenous infusion or intravenous injection. In some aspects, the JAK inhibitor is administered by an intravenous infusion. In some aspects, the JAK inhibitor is administered by an intravenous injection. In some aspects, the JAK inhibitor is administered by subcutaneous injection. In some aspects, the JAK inhibitor is administered by intravenous infusion and then subsequently administered by subcutaneous injection. These methods of administration can be designed to be short acting, fast releasing, or long acting. Furthermore, the JAK inhibitor can be administered in a local rather than systemic means, such as administration (e.g., by injection) at a tumor site.

In some aspects, each therapeutic agent in the combination disclosed herein (e.g., the compound of formula (I) and a JAK inhibitor) can be administered by the same route or by different routes. For example, a first therapeutic agent of the combination can be administered by intravenous injection while the other therapeutic agent or agents of the combination can be administered orally. Alternatively, for example, all therapeutic agents can be administered orally or all therapeutic agents can be administered by intravenous injection. Therapeutic agents may also be administered in alternation.

In some aspects, the JAK inhibitor may also be administered by nasal aerosol or inhalation. The JAK inhibitor can be prepared according to techniques well known in the art and can be prepared as solutions in saline, employing benzyl alcohol or other suitable preservatives, absorption promoters to enhance bioavailability, fluorocarbons, and/or other conventional solubilizing or dispersing agents.

The amounts or suitable doses of the methods of this disclosure depends upon a number of factors, including the nature of the severity of the condition to be treated, the particular inhibitor, the route of administration and the age, weight, general health, and response of the individual patient. In some aspects, the suitable dose level is one that achieves a therapeutic response as measured by tumor regression, or other standard measures of disease progression, progression free survival or overall survival. In some aspects, the suitable dose level is one that achieves this therapeutic response and also minimizes any side effects associated with the administration of the therapeutic agent. The suitable dose levels can be ones that prolong the therapeutic response and/or prolong life.

It will be understood that a suitable dose of the BET inhibitor, the JAK inhibitor, and optionally one or more additional therapeutic agents can be taken at any time of the day or night. In some aspects, a suitable dose of each agent is taken in the morning. In some other aspects, a suitable dose of each agent is taken in the evening. In some aspects, a suitable dose of each of the agents is taken both in the morning and the evening. It will be understood that a suitable dose of each agent can be taken with or without food. In some aspects a suitable dose of an agent is taken with a meal. In some aspects a suitable dose of an agent is taken while fasting.

In some aspects, the compound of formula (I), or a pharmaceutically acceptable salt thereof, is administered on a daily schedule. In some aspects, the compound of formula (I), or a pharmaceutically acceptable salt thereof, is administered twice per day. In some aspects, the compound of formula (I), or a pharmaceutically acceptable salt thereof, is administered three times per day. In some aspects, the compound of formula (I), or a pharmaceutically acceptable salt thereof, is administered four times a day. In some aspects, the compound of formula (I), or a pharmaceutically acceptable salt thereof, is administered five times a day.

In some aspects, the compound of formula (I), or a pharmaceutically acceptable salt thereof, is administered every other day. In some aspects, the compound of formula (I), or a pharmaceutically acceptable salt thereof is administered once every three days. In some aspects, the compound of formula (I), or a pharmaceutically acceptable salt thereof is administered on a twice-weekly schedule. In some aspects, the compound of formula (I), or a pharmaceutically acceptable salt thereof is administered on a three times a week schedule. In some aspects, the compound of formula (I), or a pharmaceutically acceptable salt thereof is administered on a weekly schedule. In some aspects, the compound of formula (I), or a pharmaceutically acceptable salt thereof is administered on a once every two weeks schedule.

In some aspects, the compound of formula (I), or a pharmaceutically acceptable salt thereof is administered at least 3 times on alternate days within a 7-day cycle. In some aspects, the compound of formula (I), or a pharmaceutically acceptable salt thereof is administered on day 1 and day 4 of a 7-day cycle. In some aspects, the compound of formula (I), or a pharmaceutically acceptable salt thereof is administered on consecutive days in a 7-day cycle followed by an intermission. In some aspects, the compound of formula (I), or a pharmaceutically acceptable salt thereof is administered for 2 consecutive days followed by an intermission of 5 consecutive days for at least one 7-day cycle. In some aspects, the compound of formula (I), or a pharmaceutically acceptable salt thereof is administered for 3 consecutive days followed by an intermission of 4 consecutive days for at least one 7-day cycle. In some aspects, the compound of formula (I), or a pharmaceutically acceptable salt thereof is administered for 4 consecutive days followed by an intermission of 3 consecutive days for at least one 7-day cycle. In some aspects, the compound of formula (I), or a pharmaceutically acceptable salt thereof is administered for 5 consecutive days followed by an intermission of 2 consecutive days for at least one 7-day cycle. In some aspects, there will be periods of rest between one or more of the 7-day treatment cycles. In some aspects, there will be a 7-day rest between one or more of the 7-day treatment cycles.

The present description contemplates administration of the BET inhibitor for one or more treatment cycles, for example, 1, 2, 3, 4, 5, 6, or more, treatment cycles. In some aspects, a treatment cycle is about 7 days to about 56 days, or more. In some aspects, a treatment cycle is 7 days, 14 days, 21 days, 28 days, 35 days, 42 days, 49 days, or 56 days. In some aspects, a treatment cycle is 21 days or 28 days. In some aspects, there will be periods of rest within or between one or more of the treatment cycles. For example, in some aspects, there will be a period of rest at the end of the treatment cycle. In some aspects, there will be a period of rest between the second and third treatment cycle but not the first and second treatment cycle. In another aspect, there might be a period of rest between the first and second treatment cycle but not the second and third treatment cycle. Dosing schedules include, for example, administering the BET inhibitor once during a treatment schedule, e.g., on day 1 of a 21 day cycle, twice during a treatment cycle, e.g., on days 1 and 15 of a 21 day cycle or on days 1 and 15 of a 28 day cycle, three times during a treatment cycle, e.g., on days 1, 8 and 15 of a 21 day cycle or on days 1, 8 and 15 of a 28 day cycle, and four times during a treatment cycle, e.g., on days 1, 4, 8, and 11 of a 21 day cycle or of on days 1, 4, 8, and 11 of a 28 day cycle. Other dosage schedules are encompassed by the present disclosure.

In some aspects, the compound of formula (I), or a pharmaceutically acceptable salt thereof is administered within a 21-day cycle. In some aspects, the compound of formula (I), or a pharmaceutically acceptable salt thereof is administered at least two times within a 21-day cycle. In some aspects, the compound of formula (I), or a pharmaceutically acceptable salt thereof is administered at least four times within a 21-day cycle. In some aspects, the compound of formula (I), or a pharmaceutically acceptable salt thereof is administered on day 1 within a 21-day cycle. In some aspects, the compound of formula (I), or a pharmaceutically acceptable salt thereof is administered on day 4 within a 21-day cycle. In some aspects, the compound of formula (I), or a pharmaceutically acceptable salt thereof is administered on day 8 within a 21-day cycle. In some aspects, the compound of formula (I), or a pharmaceutically acceptable salt thereof is administered on day 11 within a 21-day cycle. In some aspects, the compound of formula (I), or a pharmaceutically acceptable salt thereof is administered on days 1, 4, 8, and 11 within a 21-day cycle.

In some aspects, the compound of formula (I), or a pharmaceutically acceptable salt thereof is administered for a duration of 1 year or less. In some aspects, the compound of formula (I), or a pharmaceutically acceptable salt thereof is administered for a duration of 1 year or more. In some aspects, the compound of formula (I), or a pharmaceutically acceptable salt thereof is administered for a duration of 24 months or less. In some aspects, the compound of formula (I), or a pharmaceutically acceptable salt thereof is administered for a duration of 24 months or more.

In some aspects, the compound of formula (I), or a pharmaceutically acceptable salt thereof is administered once a week. In some aspects, the compound of formula (I), or a pharmaceutically acceptable salt thereof is administered once a week for two weeks. In some aspects, the compound of formula (I), or a pharmaceutically acceptable salt thereof is administered once a week for two weeks within a 21-day cycle.

In some aspects, the amount of the compound of formula (I), or a pharmaceutically acceptable salt thereof that is administered on each day of dosing is about 0.1 mg to about 20 mg. In some aspects, the amount of the compound of formula (I), or a pharmaceutically acceptable salt thereof that is administered on each day of dosing is about 0.1 mg to about 15 mg. In some aspects, the amount of the compound of formula (I), or a pharmaceutically acceptable salt thereof that is administered on each day of dosing is about 0.1 mg to about 10 mg. In some aspects, the amount of the compound of formula (I), or a pharmaceutically acceptable salt thereof that is administered on each day of dosing is about 0.1 mg to about 8 mg. In some aspects, the amount of the compound of formula (I), or a pharmaceutically acceptable salt thereof that is administered on each day of dosing is about 0.1 mg to about 5 mg. In some aspects, the amount of the compound of formula (I), or a pharmaceutically acceptable salt thereof that is administered on each day of dosing is about 0.2 mg to about 5 mg. In some aspects, the amount of the compound of formula (I), or a pharmaceutically acceptable salt thereof that is administered on each day of dosing is about 0.25 mg to about 5 mg.

In some aspects, the amount of the compound of formula (I), or a pharmaceutically acceptable salt thereof that is administered on each day of dosing is about 0.1 mg. In some aspects, the amount of the compound of formula (I), or a pharmaceutically acceptable salt thereof that is administered on each day of dosing is about 0.2 mg. In some aspects, the amount of the compound of formula (I), or a pharmaceutically acceptable salt thereof that is administered on each day of dosing is about 0.25 mg. In some aspects, the amount of the compound of formula (I), or a pharmaceutically acceptable salt thereof that is administered on each day of dosing is about 0.3 mg. In some aspects, the amount of the compound of formula (I), or a pharmaceutically acceptable salt thereof that is administered on each day of dosing is about 0.4 mg. In some aspects, the amount of the compound of formula (I), or a pharmaceutically acceptable salt thereof that is administered on each day of dosing is about 0.5 mg. In some aspects, the amount of the compound of formula (I), or a pharmaceutically acceptable salt thereof that is administered on each day of dosing is about 0.6 mg. In some aspects, the amount of the compound of formula (I), or a pharmaceutically acceptable salt thereof that is administered on each day of dosing is about 0.7 mg. In some aspects, the amount of the compound of formula (I), or a pharmaceutically acceptable salt thereof that is administered on each day of dosing is about 0.8 mg. In some aspects, the amount of the compound of formula (I), or a pharmaceutically acceptable salt thereof that is administered on each day of dosing is about 0.9 mg. In some aspects, the amount of the compound of formula (I), or a pharmaceutically acceptable salt thereof that is administered on each day of dosing is about 1 mg. In some aspects, the amount of the compound of formula (I), or a pharmaceutically acceptable salt thereof that is administered on each day of dosing is about 1.1 mg. In some aspects, the amount of the compound of formula (I), or a pharmaceutically acceptable salt thereof that is administered on each day of dosing is about 1.2 mg. In some aspects, the amount of the compound of formula (I), or a pharmaceutically acceptable salt thereof that is administered on each day of dosing is about 1.3 mg. In some aspects, the amount of the compound of formula (I), or a pharmaceutically acceptable salt thereof that is administered on each day of dosing is about 1.4 mg. In some aspects, the amount of the compound of formula (I), or a pharmaceutically acceptable salt thereof that is administered on each day of dosing is about 1.5 mg. In some aspects, the amount of the compound of formula (I), or a pharmaceutically acceptable salt thereof that is administered on each day of dosing is about 1.6 mg. In some aspects, the amount of the compound of formula (I), or a pharmaceutically acceptable salt thereof that is administered on each day of dosing is about 1.7 mg. In some aspects, the amount of the compound of formula (I), or a pharmaceutically acceptable salt thereof that is administered on each day of dosing is about 1.8 mg. In some aspects, the amount of the compound of formula (I), or a pharmaceutically acceptable salt thereof that is administered on each day of dosing is about 1.9 mg. In some aspects, the amount of the compound of formula (I), or a pharmaceutically acceptable salt thereof that is administered on each day of dosing is about 2 mg. In some aspects, the amount of the compound of formula (I), or a pharmaceutically acceptable salt thereof that is administered on each day of dosing is about 2.1 mg. In some aspects, the amount of the compound of formula (I), or a pharmaceutically acceptable salt thereof that is administered on each day of dosing is about 2.2 mg. In some aspects, the amount of the compound of formula (I), or a pharmaceutically acceptable salt thereof that is administered on each day of dosing is about 2.3 mg. In some aspects, the amount of the compound of formula (I), or a pharmaceutically acceptable salt thereof that is administered on each day of dosing is about 2.4 mg. In some aspects, the amount of the compound of formula (I), or a pharmaceutically acceptable salt thereof that is administered on each day of dosing is about 2.5 mg. In some aspects, the amount of the compound of formula (I), or a pharmaceutically acceptable salt thereof that is administered on each day of dosing is about 2.6 mg. In some aspects, the amount of the compound of formula (I), or a pharmaceutically acceptable salt thereof that is administered on each day of dosing is about 2.7 mg. In some aspects, the amount of the compound of formula (I), or a pharmaceutically acceptable salt thereof that is administered on each day of dosing is about 2.8 mg. In some aspects, the amount of the compound of formula (I), or a pharmaceutically acceptable salt thereof that is administered on each day of dosing is about 2.9 mg. In some aspects, the amount of the compound of formula (I), or a pharmaceutically acceptable salt thereof that is administered on each day of dosing is about 3 mg.

In some aspect, the method comprises administering to the subject the compound of formula (I), or a pharmaceutically acceptable salt thereof, at a daily dose of about 0.25 mg to about 6 mg, or about 3.1 mg, about 3.2 mg, about 3.3 mg, about 3.4 mg, about 3.5 mg, about 3.6 mg, about 237 mg, about 3.8 mg, about 3.9 mg, about 4.0 mg, about 4.1 mg, about 4.2 mg, about 4.3 mg, about 4.4 mg, about 4.5 mg, about 4.6 mg, about 4.7 mg, about 4.8 mg, about 4.9 mg, about 5.0 mg, about 5.1 mg, about 5.2 mg, about 5.3 mg, about 5.4 mg, about 5.5 mg, about 5.6 mg, about 5.7 mg, about 5.8 mg, about 5.9 mg, or 6 mg.

All dosing amounts refer to the amount of the compound of formula (I) administered, and do not include the weight amount of any pharmaceutically acceptable salt.

In some aspects, the compound of formula (I), or the pharmaceutically acceptable salt thereof, is administered at a dose of from about 0.25 mg to about 4.5 mg. In some aspects, the compound of formula (I), or the pharmaceutically acceptable salt thereof, is administered for 5 consecutive days on a 28-day cycle followed by a 2-day rest period. In some aspects, the compound of formula (I), or the pharmaceutically acceptable salt thereof, is administered for 14 consecutive days on a 21-day cycle followed by a 7-day rest period. In some aspects, the compound of formula (I), or the pharmaceutically acceptable salt thereof, is administered for 7 consecutive days on a 21-day cycle followed by a 14-day rest period.

In some aspects, the compound of formula (I), or a pharmaceutically acceptable salt thereof is administered as an intravenous (IV) infusion. In some aspects, the compound of formula (I), or a pharmaceutically acceptable salt thereof is administered as a 60±10 minute IV infusion. In some aspects, the compound of formula (I), or a pharmaceutically acceptable salt thereof is administered as a 300 minute or less IV infusion. In some aspects, the compound of formula (I), or a pharmaceutically acceptable salt thereof is administered as a 60 minute to 300 minute IV infusion.

In some aspects, the JAK inhibitor is administered on a daily schedule. In some aspects, the JAK inhibitor is administered every other day. In some aspects, the JAK inhibitor is administered once every three days. In some aspects, the JAK inhibitor is administered on a twice-weekly schedule. In some aspects, the JAK inhibitor is administered on a three times a week schedule. In some aspects, the JAK inhibitor is administered on a weekly schedule. In some aspects, the JAK inhibitor is administered on a once every two weeks schedule. In some aspects, the JAK inhibitor is administered on a once every three weeks schedule. In some aspects, the JAK inhibitor is administered on a once every four weeks schedule. In some aspects, the JAK inhibitor is administered on a once every eight weeks schedule. In some aspects, the JAK inhibitor is administered on a once every twelve weeks schedule.

In some aspects, the JAK inhibitor is administered at least 3 times on alternate days within a 7-day cycle. In some aspects, the JAK inhibitor is administered on day 1 of a treatment cycle. In some aspects, the JAK inhibitor is administered on day 1 and day 4 of a 7-day cycle. In some aspects, the JAK inhibitor is administered on consecutive days in a 7-day cycle followed by an intermission. In some aspects, the JAK inhibitor is administered for 2 consecutive days followed by an intermission of 5 consecutive days for at least one 7-day cycle. In some aspects, the JAK inhibitor is administered for 3 consecutive days followed by an intermission of 4 consecutive days for at least one 7-day cycle. In some aspects, the JAK inhibitor is administered for 4 consecutive days followed by an intermission of 3 consecutive days for at least one 7-day cycle. In some aspects, the JAK inhibitor is administered for 5 consecutive days followed by an intermission of 2 consecutive days for at least one 7-day cycle.

The present description of the administration of the JAK inhibitor for one or more treatment cycles, for example, 1, 2, 3, 4, 5, 6, or more, treatment cycles. In some aspects, a treatment cycle is about 7 days to about 84 days, or more. In some aspects, a treatment cycle is 7 days, 14 days, 21 days, 28 days, 35 days, 42 days, 49 days, 56 days, or 84 days. In some aspects, a treatment cycle is 21 days or 28 days. In some aspects, there will be periods of rest within or between one or more of the treatment cycles. For example, in some aspects, there will be a period of rest at the end of the treatment cycle. In some aspects, there will be a period of rest between the second and third treatment cycle but not the first and second treatment cycle. In another aspect, there might be a period of rest between the first and second treatment cycle but not the second and third treatment cycle. Dosing schedules include, for example, administering the JAK inhibitor once during a treatment schedule, e.g., on day 1 of a 21 day cycle, twice during a treatment cycle, e.g., on days 1 and 15 of a 21 day cycle or on days 1 and 15 of a 28 day cycle, three times during a treatment cycle, e.g., on days 1, 8 and 15 of a 21 day cycle or on days 1, 8 and 15 of a 28 day cycle, and four times during a treatment cycle, e.g., on days 1, 4, 8, and 11 of a 21 day cycle or of on days 1, 4, 8, and 11 of a 28 day cycle. Other dosage schedules are encompassed by the present disclosure.

In some aspects, the JAK inhibitor is administered within a 21-day cycle. In some aspects, the JAK inhibitor is administered on day 1 of a 21-day cycle.

In some aspects, the compound of formula (I), or a pharmaceutically acceptable salt thereof is administered on the same day as the JAK inhibitor. In some aspects, the compound of formula (I), or a pharmaceutically acceptable salt thereof is administered before the JAK inhibitor when both are administered on the same day. In some aspects, the JAK inhibitor is administered before the compound of formula (I), or a pharmaceutically acceptable salt thereof when both are administered on the same day.

In some aspects, the dose of the compound of formula (I), or a pharmaceutically acceptable salt thereof is delayed from 1 to 3 days within a 21-day cycle. In some aspects, the dose of the JAK inhibitor is delayed from 1 to 3 days within a 21-day cycle. In some aspects, the dose of both the compound of formula (I), or a pharmaceutically acceptable salt thereof and the JAK inhibitor are delayed from 1 to 3 days within a 21-day cycle.

In some aspects, the JAK inhibitor is administered by subcutaneous injection. In some aspects, the JAK inhibitor is administered by intravenous infusion followed by one or more subsequent subcutaneous injections. In some aspects, the intravenous infusion and one or more subsequent subcutaneous injections are administered according to the dosing schedules and methods disclosed herein.

In some aspects, the amount of the JAK inhibitor that is administered on each day of dosing is about 5 mg to about 200 mg. In some aspects, the amount of the JAK inhibitor that is administered on each day of dosing is about 5 mg to about 190 mg. In some aspects, the amount of the JAK inhibitor that is administered on each day of dosing is about 5 mg to about 180 mg. In some aspects, the amount of the JAK inhibitor that is administered on each day of dosing is about 5 mg to about 170 mg. In some aspects, the amount of the JAK inhibitor that is administered on each day of dosing is about 5 mg to about 160 mg. In some aspects, the amount of the JAK inhibitor that is administered on each day of dosing is about 5 mg to about 150 mg. In some aspects, the amount of the JAK inhibitor that is administered on each day of dosing is about 5 mg to about 140 mg. In some aspects, the amount of the JAK inhibitor that is administered on each day of dosing is about 5 mg to about 130 mg. In some aspects, the amount of the JAK inhibitor that is administered on each day of dosing is about 5 mg to about 120 mg. In some aspects, the amount of the JAK inhibitor that is administered on each day of dosing is about 5 mg to about 110 mg. In some aspects, the amount of the JAK inhibitor that is administered on each day of dosing is about 5 mg to about 100 mg. In some aspects, the amount of the JAK inhibitor that is administered on each day of dosing is about 5 mg to about 90 mg. In some aspects, the amount of the JAK inhibitor that is administered on each day of dosing is about 5 mg to about 80 mg. In some aspects, the amount of the JAK inhibitor that is administered on each day of dosing is about 5 mg to about 70 mg. In some aspects, the amount of the JAK inhibitor that is administered on each day of dosing is about 5 mg to about 60 mg. In some aspects, the amount of the JAK inhibitor that is administered on each day of dosing is about 5 mg to about 50 mg. In some aspects, the amount of the JAK inhibitor that is administered on each day of dosing is about 5 mg to about 40 mg. In some aspects, the amount of the JAK inhibitor that is administered on each day of dosing is about 5 mg to about 30 mg.

In some aspects, the amount of the JAK inhibitor that is administered on each day of dosing is about 50 mg to about 500 mg. In some aspects, the amount of the JAK inhibitor that is administered on each day of dosing is about 55 mg to about 500 mg. In some aspects, the amount of the JAK inhibitor that is administered on each day of dosing is about 60 mg to about 500 mg. In some aspects, the amount of the JAK inhibitor that is administered on each day of dosing is about 70 mg to about 500 mg. In some aspects, the amount of the JAK inhibitor that is administered on each day of dosing is about 80 mg to about 500 mg. In some aspects, the amount of the JAK inhibitor that is administered on each day of dosing is about 90 mg to about 500 mg. In some aspects, the amount of the JAK inhibitor that is administered on each day of dosing is about 100 mg to about 500 mg. In some aspects, the amount of the JAK inhibitor that is administered on each day of dosing is about 120 mg to about 500 mg. In some aspects, the amount of the JAK inhibitor that is administered on each day of dosing is about 130 mg to about 500 mg. In some aspects, the amount of the JAK inhibitor that is administered on each day of dosing is about 140 mg to about 500 mg. In some aspects, the amount of the JAK inhibitor that is administered on each day of dosing is about 150 mg to about 500 mg. In some aspects, the amount of the JAK inhibitor that is administered on each day of dosing is about 160 mg to about 500 mg. In some aspects, the amount of the JAK inhibitor that is administered on each day of dosing is about 170 mg to about 500 mg. In some aspects, the amount of the JAK inhibitor that is administered on each day of dosing is about 180 mg to about 500 mg. In some aspects, the amount of the JAK inhibitor that is administered on each day of dosing is about 190 mg to about 500 mg. In some aspects, the amount of the JAK inhibitor that is administered on each day of dosing is about 200 mg to about 500 mg. In some aspects, the amount of the JAK inhibitor that is administered on each day of dosing is about 210 mg to about 500 mg. In some aspects, the amount of the JAK inhibitor that is administered on each day of dosing is about 220 mg to about 500 mg. In some aspects, the amount of the JAK inhibitor that is administered on each day of dosing is about 230 mg to about 500 mg. In some aspects, the amount of the JAK inhibitor that is administered on each day of dosing is about 240 mg to about 500 mg. In some aspects, the amount of the JAK inhibitor that is administered on each day of dosing is about 250 mg to about 500 mg. In some aspects, the amount of the JAK inhibitor that is administered on each day of dosing is about 260 mg to about 500 mg. In some aspects, the amount of the JAK inhibitor that is administered on each day of dosing is about 270 mg to about 500 mg. In some aspects, the amount of the JAK inhibitor that is administered on each day of dosing is about 280 mg to about 500 mg. In some aspects, the amount of the JAK inhibitor that is administered on each day of dosing is about 290 mg to about 500 mg. In some aspects, the amount of the JAK inhibitor that is administered on each day of dosing is about 300 mg to about 500 mg.

In some aspects, the amount of the JAK inhibitor that is administered on each day of dosing is about 50 mg to about 400 mg. In some aspects, the amount of the JAK inhibitor that is administered on each day of dosing is about 55 mg to about 400 mg. In some aspects, the amount of the JAK inhibitor that is administered on each day of dosing is about 60 mg to about 400 mg. In some aspects, the amount of the JAK inhibitor that is administered on each day of dosing is about 70 mg to about 400 mg. In some aspects, the amount of the JAK inhibitor that is administered on each day of dosing is about 80 mg to about 400 mg. In some aspects, the amount of the JAK inhibitor that is administered on each day of dosing is about 90 mg to about 400 mg. In some aspects, the amount of the JAK inhibitor that is administered on each day of dosing is about 100 mg to about 400 mg. In some aspects, the amount of the JAK inhibitor that is administered on each day of dosing is about 120 mg to about 400 mg. In some aspects, the amount of the JAK inhibitor that is administered on each day of dosing is about 130 mg to about 400 mg. In some aspects, the amount of the JAK inhibitor that is administered on each day of dosing is about 140 mg to about 400 mg. In some aspects, the amount of the JAK inhibitor that is administered on each day of dosing is about 150 mg to about 400 mg. In some aspects, the amount of the JAK inhibitor that is administered on each day of dosing is about 160 mg to about 400 mg. In some aspects, the amount of the JAK inhibitor that is administered on each day of dosing is about 170 mg to about 400 mg. In some aspects, the amount of the JAK inhibitor that is administered on each day of dosing is about 180 mg to about 400 mg. In some aspects, the amount of the JAK inhibitor that is administered on each day of dosing is about 190 mg to about 400 mg. In some aspects, the amount of the JAK inhibitor that is administered on each day of dosing is about 200 mg to about 400 mg. In some aspects, the amount of the JAK inhibitor that is administered on each day of dosing is about 210 mg to about 400 mg. In some aspects, the amount of the JAK inhibitor that is administered on each day of dosing is about 220 mg to about 400 mg. In some aspects, the amount of the JAK inhibitor that is administered on each day of dosing is about 230 mg to about 400 mg. In some aspects, the amount of the JAK inhibitor that is administered on each day of dosing is about 240 mg to about 400 mg. In some aspects, the amount of the JAK inhibitor that is administered on each day of dosing is about 250 mg to about 400 mg. In some aspects, the amount of the JAK inhibitor that is administered on each day of dosing is about 260 mg to about 400 mg. In some aspects, the amount of the JAK inhibitor that is administered on each day of dosing is about 270 mg to about 500 mg. In some aspects, the amount of the JAK inhibitor that is administered on each day of dosing is about 280 mg to about 400 mg. In some aspects, the amount of the JAK inhibitor that is administered on each day of dosing is about 290 mg to about 400 mg. In some aspects, the amount of the JAK inhibitor that is administered on each day of dosing is about 300 mg to about 400 mg.

In some aspects, the JAK inhibitor is fedratinib, or a pharmaceutically acceptable salt thereof. In some aspects, the JAK inhibitor is ruxolitinib, or a pharmaceutically acceptable salt thereof. In some aspects, the JAK inhibitor is tofacitinib, or a pharmaceutically acceptable salt thereof. In some aspects, the JAK inhibitor is oclacitinib, or a pharmaceutically acceptable salt thereof. In some aspects, the JAK inhibitor is baricitinib, or a pharmaceutically acceptable salt thereof. In some aspects, the JAK inhibitor is peficitinib, or a pharmaceutically acceptable salt thereof. In some aspects, the JAK inhibitor is upadacitinib, or a pharmaceutically acceptable salt thereof.

In some aspect, the method comprises administering to the subject the compound of formula (I), or a pharmaceutically acceptable salt thereof, and fedratinib, or a pharmaceutically acceptable salt thereof, or ruxolitinib, or a pharmaceutically acceptable salt thereof, wherein the compound of formula (I) is administered at a daily dose of about 0.25 mg to about 6 mg, or about 0.3 mg, about 0.4 mg, about 0.5 mg, about 0.6 mg, about 0.7 mg, about 0.8 mg, about 0.9 mg, about 1.0 mg, about 1.1 mg, about 1.2 mg, about 1.3 mg, about 1.4 mg, about 1.5 mg, about 1.6 mg, about 1.7 mg, about 1.8 mg, about 1.9 mg, about 2.0 mg, about 2.1 mg, about 2.2 mg, about 2.3 mg, about 2.4 mg, about 2.5 mg, about 2.6 mg, about 2.7 mg, about 2.8 mg, about 2.9 mg, about 3.0 mg, about 3.1 mg, about 3.2 mg, about 3.3 mg, about 3.4 mg, about 3.5 mg, about 3.6 mg, about 237 mg, about 3.8 mg, about 3.9 mg, about 4.0 mg, about 4.1 mg, about 4.2 mg, about 4.3 mg, about 4.4 mg, about 4.5 mg, about 4.6 mg, about 4.7 mg, about 4.8 mg, about 4.9 mg, about 5.0 mg, about 5.1 mg, about 5.2 mg, about 5.3 mg, about 5.4 mg, about 5.5 mg, about 5.6 mg, about 5.7 mg, about 5.8 mg, about 5.9 mg, or 6 mg.

In some aspect, the method comprises administering to the subject the compound of formula (I), or a pharmaceutically acceptable salt thereof, and fedratinib, or a pharmaceutically acceptable salt thereof, wherein the fedratinib is administered at a daily dose from about 25 mg to about 600 mg, or about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg.

In some aspects, fedratinib, or a pharmaceutically acceptable salt thereof, is administered at a daily dose of 50 mg, 100 mg, 200 mg, 300, or 400 mg together with the compound of formula (I), or a pharmaceutically acceptable salt thereof.

In some aspect, the method comprises administering to the subject the compound of formula (I), or a pharmaceutically acceptable salt thereof, and ruxolitinib, or a pharmaceutically acceptable salt thereof, wherein the ruxolitinib is administered at a daily dose from about 5 mg to about 100 mg, or about 6 mg, about 8 mg, about 10 mg, about 12 mg, about 14 mg, about 15 mg, about 16 mg, about 18 mg, about 20 mg, about 22 mg, about 24 mg, about 26 mg, about 28 mg, about 30 mg, about 32 mg, about 34 mg, about 36 mg, about 38 mg, about 40 mg, about 42 mg, about 44 mg, about 46 mg, about 48 mg, about 50 mg, about 52 mg, about 54 mg, about 56 mg, about 58 mg, about 60 mg, about 62 mg, about 64 mg, about 66 mg, about 68 mg, about 70 mg, about 72 mg, about 74 mg, about 76 mg, about 78 mg, about 80 mg, about 82 mg, about 84 mg, about 86 mg, about 88 mg, about 90 mg, about 92 mg, about 94 mg, about 96 mg, about 98 mg or about 100 mg.

In some aspects, ruxolitinib, or a pharmaceutically acceptable salt thereof, is administered at a daily dose of 10 mg, 15 mg, 20 mg, 25 mg, 30 mg, 35 mg, 40 mg, 45 mg, 50 mg, 55 mg or 60 mg together with the compound of formula (I), or a pharmaceutically acceptable salt thereof.

In some aspects, the method comprises administering to the subject the compound of formula (I), or a pharmaceutically acceptable salt thereof, at a dose of 0.25 mg; and fedratinib, or a pharmaceutically acceptable salt and/or solvate (e.g., a hydrate) thereof, at a dose of 200 mg, 300 mg, or 400 mg.

In some aspects, the method comprises administering to the subject the compound of formula (I), or a pharmaceutically acceptable salt thereof, at a dose of 0.25 mg; and fedratinib, or a pharmaceutically acceptable salt and/or solvate (e.g., a hydrate) thereof, at a starting dose of 400 mg.

In some aspects, the method comprises administering to the subject the compound of formula (I), or a pharmaceutically acceptable salt thereof, at a dose of 0.25 mg; and fedratinib, or a pharmaceutically acceptable salt and/or solvate (e.g., a hydrate) thereof, at a dose of 400 mg.

In some aspects, the method comprises administering to the subject the compound of formula (I), or a pharmaceutically acceptable salt thereof, at a dose of 0.5 mg; and fedratinib, or a pharmaceutically acceptable salt and/or solvate (e.g., a hydrate) thereof, at a dose of 200 mg, 300 mg, or 400 mg.

In some aspects, the method comprises administering to the subject the compound of formula (I), or a pharmaceutically acceptable salt thereof, at a dose of 0.5 mg; and fedratinib, or a pharmaceutically acceptable salt and/or solvate (e.g., a hydrate) thereof, at a dose of 400 mg.

In some aspects, the method comprises administering to the subject the compound of formula (I), or a pharmaceutically acceptable salt thereof, at a dose of 0.75 mg; and fedratinib, or a pharmaceutically acceptable salt and/or solvate (e.g., a hydrate) thereof, at a dose of 200 mg, 300 mg, or 400 mg.

In some aspects, the method comprises administering to the subject the compound of formula (I), or a pharmaceutically acceptable salt thereof, at a dose of 0.75 mg; and fedratinib, or a pharmaceutically acceptable salt and/or solvate (e.g., a hydrate) thereof, at a dose of 400 mg.

In some aspects, the method comprises administering to the subject the compound of formula (I), or a pharmaceutically acceptable salt thereof, at a dose of 1.0 mg; and fedratinib, or a pharmaceutically acceptable salt and/or solvate (e.g., a hydrate) thereof, at a dose of 200 mg, 300 mg, or 400 mg.

In some aspects, the method comprises administering to the subject the compound of formula (I), or a pharmaceutically acceptable salt thereof, at a dose of 1.0 mg; and fedratinib, or a pharmaceutically acceptable salt and/or solvate (e.g., a hydrate) thereof, at a dose of 400 mg.

In some aspects, the method comprises administering to the subject the compound of formula (I), or a pharmaceutically acceptable salt thereof, at a dose of 1.25 mg; and fedratinib, or a pharmaceutically acceptable salt and/or solvate (e.g., a hydrate) thereof, at a dose of 200 mg, 300 mg, or 400 mg.

In some aspects, the method comprises administering to the subject the compound of formula (I), or a pharmaceutically acceptable salt thereof, at a dose of 1.25 mg; and fedratinib, or a pharmaceutically acceptable salt and/or solvate (e.g., a hydrate) thereof, at a dose of 400 mg.

In some aspects, the method comprises administering to the subject the compound of formula (I), or a pharmaceutically acceptable salt thereof, at a dose of 1.5 mg; and fedratinib, or a pharmaceutically acceptable salt and/or solvate (e.g., a hydrate) thereof, at a dose of 200 mg, 300 mg, or 400 mg.

In some aspects, the method comprises administering to the subject the compound of formula (I), or a pharmaceutically acceptable salt thereof, at a dose of 1.5 mg; and fedratinib, or a pharmaceutically acceptable salt and/or solvate (e.g., a hydrate) thereof, at a dose of 400 mg.

In some aspects, the method comprises administering to the subject the compound of formula (I), or a pharmaceutically acceptable salt thereof, at a dose of 2.0 mg; and fedratinib, or a pharmaceutically acceptable salt and/or solvate (e.g., a hydrate) thereof, at a dose of 200 mg, 300 mg, or 400 mg.

In some aspects, the method comprises administering to the subject the compound of formula (I), or a pharmaceutically acceptable salt thereof, at a dose of 2.0 mg; and fedratinib, or a pharmaceutically acceptable salt and/or solvate (e.g., a hydrate) thereof, at a dose of 400 mg.

In some aspects, the subject treated with the compound of formula (I), or a pharmaceutically acceptable salt thereof, at a dose of 0.25 mg; and fedratinib, or a pharmaceutically acceptable salt and/or solvate (e.g., a hydrate) thereof, at a dose of 200 mg, 300 mg, or 400 mg has a relapsing disease, a refractory disease or is intolerant to ruxolitinib.

In some aspects, the subject treated with the compound of formula (I), or a pharmaceutically acceptable salt thereof, at a dose of 0.25 mg; and fedratinib, or a pharmaceutically acceptable salt and/or solvate (e.g., a hydrate) thereof, at a dose of 400 mg has a relapsing disease, a refractory disease or is intolerant to ruxolitinib.

In some aspects, the subject treated with the compound of formula (I), or a pharmaceutically acceptable salt thereof, at a dose of 0.5 mg; and fedratinib, or a pharmaceutically acceptable salt and/or solvate (e.g., a hydrate) thereof, at a dose of 200 mg, 300 mg, or 400 mg has a relapsing disease, a refractory disease or is intolerant to ruxolitinib.

In some aspects, the subject treated with the compound of formula (I), or a pharmaceutically acceptable salt thereof, at a dose of 0.5 mg; and fedratinib, or a pharmaceutically acceptable salt and/or solvate (e.g., a hydrate) thereof, at a dose of 400 mg has a relapsing disease, a refractory disease or is intolerant to ruxolitinib.

In some aspects, the subject treated with the compound of formula (I), or a pharmaceutically acceptable salt thereof, at a dose of 0.75 mg; and fedratinib, or a pharmaceutically acceptable salt and/or solvate (e.g., a hydrate) thereof, at a dose of 200 mg, 300 mg, or 400 mg has a relapsing disease, a refractory disease or is intolerant to ruxolitinib.

In some aspects, the subject treated with the compound of formula (I), or a pharmaceutically acceptable salt thereof, at a dose of 0.75 mg; and fedratinib, or a pharmaceutically acceptable salt and/or solvate (e.g., a hydrate) thereof, at a dose of 400 mg has a relapsing disease, a refractory disease or is intolerant to ruxolitinib.

In some aspects, the subject treated with the compound of formula (I), or a pharmaceutically acceptable salt thereof, at a dose of 1.0 mg; and fedratinib, or a pharmaceutically acceptable salt and/or solvate (e.g., a hydrate) thereof, at a dose of 200 mg, 300 mg, or 400 mg has a relapsing disease, a refractory disease or is intolerant to ruxolitinib.

In some aspects, the subject treated with the compound of formula (I), or a pharmaceutically acceptable salt thereof, at a dose of 1.0 mg; and fedratinib, or a pharmaceutically acceptable salt and/or solvate (e.g., a hydrate) thereof, at a dose of 400 mg has a relapsing disease, a refractory disease or is intolerant to ruxolitinib.

In some aspects, the subject treated with the compound of formula (I), or a pharmaceutically acceptable salt thereof, at a dose of 1.25 mg; and fedratinib, or a pharmaceutically acceptable salt and/or solvate (e.g., a hydrate) thereof, at a dose of 200 mg, 300 mg, or 400 mg has a relapsing disease, a refractory disease or is intolerant to ruxolitinib.

In some aspects, the subject treated with the compound of formula (I), or a pharmaceutically acceptable salt thereof, at a dose of 1.25 mg; and fedratinib, or a pharmaceutically acceptable salt and/or solvate (e.g., a hydrate) thereof, at a dose of 400 mg has a relapsing disease, a refractory disease or is intolerant to ruxolitinib.

In some aspects, the subject treated with the compound of formula (I), or a pharmaceutically acceptable salt thereof, at a dose of 1.5 mg; and fedratinib, or a pharmaceutically acceptable salt and/or solvate (e.g., a hydrate) thereof, at a dose of 200 mg, 300 mg, or 400 mg has a relapsing disease, a refractory disease or is intolerant to ruxolitinib.

In some aspects, the subject treated with the compound of formula (I), or a pharmaceutically acceptable salt thereof, at a dose of 1.5 mg; and fedratinib, or a pharmaceutically acceptable salt and/or solvate (e.g., a hydrate) thereof, at a dose of 400 mg has a relapsing disease, a refractory disease or is intolerant to ruxolitinib.

In some aspects, the subject treated with the compound of formula (I), or a pharmaceutically acceptable salt thereof, at a dose of 2.0 mg; and fedratinib, or a pharmaceutically acceptable salt and/or solvate (e.g., a hydrate) thereof, at a dose of 200 mg, 300 mg, or 400 mg has a relapsing disease, a refractory disease or is intolerant to ruxolitinib.

In some aspects, the subject treated with the compound of formula (I), or a pharmaceutically acceptable salt thereof, at a dose of 2.0 mg; and fedratinib, or a pharmaceutically acceptable salt and/or solvate (e.g., a hydrate) thereof, at a dose of 400 mg has a relapsing disease, a refractory disease or is intolerant to ruxolitinib.

In some aspects, the method comprises administering to the subject the compound of formula (I), or a pharmaceutically acceptable salt thereof, at a dose of 0.75 mg; and ruxolitinib, or a pharmaceutically acceptable salt and/or solvate (e.g., a hydrate) thereof, at a dose of 5 mg, 10 mg, 15 mg, or 20 mg. In some aspects, the ruxolitinib, or the pharmaceutically acceptable salt and/or solvate (e.g., a hydrate) thereof, is administered twice a day.

In some aspects, the method comprises administering to the subject the compound of formula (I), or a pharmaceutically acceptable salt thereof, at a dose of 0.75 mg; and ruxolitinib, or a pharmaceutically acceptable salt and/or solvate (e.g., a hydrate) thereof, at a starting dose of 15 mg. In some aspects, the ruxolitinib, or the pharmaceutically acceptable salt and/or solvate (e.g., a hydrate) thereof, is administered twice a day.

In some aspects, the method comprises administering to the subject the compound of formula (I), or a pharmaceutically acceptable salt thereof, at a dose of 0.75 mg; and ruxolitinib, or a pharmaceutically acceptable salt and/or solvate (e.g., a hydrate) thereof, at a dose of 15 mg. In some aspects, the ruxolitinib, or the pharmaceutically acceptable salt and/or solvate (e.g., a hydrate) thereof, is administered twice a day.

In some aspects, the method comprises administering to the subject the compound of formula (I), or a pharmaceutically acceptable salt thereof, at a dose of 1.0 mg; and ruxolitinib, or a pharmaceutically acceptable salt and/or solvate (e.g., a hydrate) thereof, at a dose of 5 mg, 10 mg, 15 mg, or 20 mg. In some aspects, the ruxolitinib, or the pharmaceutically acceptable salt and/or solvate (e.g., a hydrate) thereof, is administered twice a day.

In some aspects, the method comprises administering to the subject the compound of formula (I), or a pharmaceutically acceptable salt thereof, at a dose of 1.0 mg; and ruxolitinib, or a pharmaceutically acceptable salt and/or solvate (e.g., a hydrate) thereof, at a starting dose of 15 mg. In some aspects, the ruxolitinib, or the pharmaceutically acceptable salt and/or solvate (e.g., a hydrate) thereof, is administered twice a day.

In some aspects, the method comprises administering to the subject the compound of formula (I), or a pharmaceutically acceptable salt thereof, at a dose of 1.0 mg; and ruxolitinib, or a pharmaceutically acceptable salt and/or solvate (e.g., a hydrate) thereof, at a dose of 15 mg. In some aspects, the ruxolitinib, or the pharmaceutically acceptable salt and/or solvate (e.g., a hydrate) thereof, is administered twice a day.

In some aspects, the method comprises administering to the subject the compound of formula (I), or a pharmaceutically acceptable salt thereof, at a dose of 1.25 mg; and ruxolitinib, or a pharmaceutically acceptable salt and/or solvate (e.g., a hydrate) thereof, at a dose of 5 mg, 10 mg, 15 mg, or 20 mg. In some aspects, the ruxolitinib, or the pharmaceutically acceptable salt and/or solvate (e.g., a hydrate) thereof, is administered twice a day.

In some aspects, the method comprises administering to the subject the compound of formula (I), or a pharmaceutically acceptable salt thereof, at a dose of 1.25 mg; and ruxolitinib, or a pharmaceutically acceptable salt and/or solvate (e.g., a hydrate) thereof, at a starting dose of 15 mg. In some aspects, the ruxolitinib, or the pharmaceutically acceptable salt and/or solvate (e.g., a hydrate) thereof, is administered twice a day.

In some aspects, the method comprises administering to the subject the compound of formula (I), or a pharmaceutically acceptable salt thereof, at a dose of 1.25 mg; and ruxolitinib, or a pharmaceutically acceptable salt and/or solvate (e.g., a hydrate) thereof, at a dose of 15 mg. In some aspects, the ruxolitinib, or the pharmaceutically acceptable salt and/or solvate (e.g., a hydrate) thereof, is administered twice a day.

In some aspects, the method comprises administering to the subject the compound of formula (I), or a pharmaceutically acceptable salt thereof, at a dose of 1.5 mg; and ruxolitinib, or a pharmaceutically acceptable salt and/or solvate (e.g., a hydrate) thereof, at a dose of 5 mg, 10 mg, 15 mg, or 20 mg. In some aspects, the ruxolitinib, or the pharmaceutically acceptable salt and/or solvate (e.g., a hydrate) thereof, is administered twice a day.

In some aspects, the method comprises administering to the subject the compound of formula (I), or a pharmaceutically acceptable salt thereof, at a dose of 1.5 mg; and ruxolitinib, or a pharmaceutically acceptable salt and/or solvate (e.g., a hydrate) thereof, at a starting dose of 15 mg. In some aspects, the ruxolitinib, or the pharmaceutically acceptable salt and/or solvate (e.g., a hydrate) thereof, is administered twice a day.

In some aspects, the method comprises administering to the subject the compound of formula (I), or a pharmaceutically acceptable salt thereof, at a dose of 1.5 mg; and ruxolitinib, or a pharmaceutically acceptable salt and/or solvate (e.g., a hydrate) thereof, at a dose of 15 mg. In some aspects, the ruxolitinib, or the pharmaceutically acceptable salt and/or solvate (e.g., a hydrate) thereof, is administered twice a day.

In some aspects, the method comprises administering to the subject the compound of formula (I), or a pharmaceutically acceptable salt thereof, at a dose of 2.0 mg; and ruxolitinib, or a pharmaceutically acceptable salt and/or solvate (e.g., a hydrate) thereof, at a dose of 5 mg, 10 mg, 15 mg, or 20 mg. In some aspects, the ruxolitinib, or the pharmaceutically acceptable salt and/or solvate (e.g., a hydrate) thereof, is administered twice a day.

In some aspects, the method comprises administering to the subject the compound of formula (I), or a pharmaceutically acceptable salt thereof, at a dose of 2.0 mg; and ruxolitinib, or a pharmaceutically acceptable salt and/or solvate (e.g., a hydrate) thereof, at a starting dose of 15 mg. In some aspects, the ruxolitinib, or the pharmaceutically acceptable salt and/or solvate (e.g., a hydrate) thereof, is administered twice a day.

In some aspects, the method comprises administering to the subject the compound of formula (I), or a pharmaceutically acceptable salt thereof, at a dose of 2.0 mg; and ruxolitinib, or a pharmaceutically acceptable salt and/or solvate (e.g., a hydrate) thereof, at a dose of 15 mg. In some aspects, the ruxolitinib, or the pharmaceutically acceptable salt and/or solvate (e.g., a hydrate) thereof, is administered twice a day.

In some aspects, the method comprises administering to the subject the compound of formula (I), or a pharmaceutically acceptable salt thereof, at a dose of 3.0 mg; and ruxolitinib, or a pharmaceutically acceptable salt and/or solvate (e.g., a hydrate) thereof, at a dose of 5 mg, 10 mg, 15 mg, or 20 mg. In some aspects, the ruxolitinib, or the pharmaceutically acceptable salt and/or solvate (e.g., a hydrate) thereof, is administered twice a day.

In some aspects, the method comprises administering to the subject the compound of formula (I), or a pharmaceutically acceptable salt thereof, at a dose of 3.0 mg; and ruxolitinib, or a pharmaceutically acceptable salt and/or solvate (e.g., a hydrate) thereof, at a starting dose of 15 mg. In some aspects, the ruxolitinib, or the pharmaceutically acceptable salt and/or solvate (e.g., a hydrate) thereof, is administered twice a day.

In some aspects, the method comprises administering to the subject the compound of formula (I), or a pharmaceutically acceptable salt thereof, at a dose of 3.0 mg; and ruxolitinib, or a pharmaceutically acceptable salt and/or solvate (e.g., a hydrate) thereof, at a dose of 15 mg. In some aspects, the ruxolitinib, or the pharmaceutically acceptable salt and/or solvate (e.g., a hydrate) thereof, is administered twice a day.

In some aspects, the method comprises administering to the subject the compound of formula (I), or a pharmaceutically acceptable salt thereof, at a dose of 4.0 mg; and ruxolitinib, or a pharmaceutically acceptable salt and/or solvate (e.g., a hydrate) thereof, at a dose of 5 mg, 10 mg, 15 mg, or 20 mg. In some aspects, the ruxolitinib, or the pharmaceutically acceptable salt and/or solvate (e.g., a hydrate) thereof, is administered twice a day.

In some aspects, the method comprises administering to the subject the compound of formula (I), or a pharmaceutically acceptable salt thereof, at a dose of 4.0 mg; and ruxolitinib, or a pharmaceutically acceptable salt and/or solvate (e.g., a hydrate) thereof, at a starting dose of 15 mg. In some aspects, the ruxolitinib, or the pharmaceutically acceptable salt and/or solvate (e.g., a hydrate) thereof, is administered twice a day.

In some aspects, the method comprises administering to the subject the compound of formula (I), or a pharmaceutically acceptable salt thereof, at a dose of 4.0 mg; and ruxolitinib, or a pharmaceutically acceptable salt and/or solvate (e.g., a hydrate) thereof, at a dose of 15 mg. In some aspects, the ruxolitinib, or the pharmaceutically acceptable salt and/or solvate (e.g., a hydrate) thereof, is administered twice a day.

In some aspects, the method comprises administering to the subject the compound of formula (I), or a pharmaceutically acceptable salt thereof, at a dose of 4.5 mg; and ruxolitinib, or a pharmaceutically acceptable salt and/or solvate (e.g., a hydrate) thereof, at a dose of 5 mg, 10 mg, 15 mg, or 20 mg. In some aspects, the ruxolitinib, or the pharmaceutically acceptable salt and/or solvate (e.g., a hydrate) thereof, is administered twice a day.

In some aspects, the method comprises administering to the subject the compound of formula (I), or a pharmaceutically acceptable salt thereof, at a dose of 4.5 mg; and ruxolitinib, or a pharmaceutically acceptable salt and/or solvate (e.g., a hydrate) thereof, at a starting dose of 15 mg. In some aspects, the ruxolitinib, or the pharmaceutically acceptable salt and/or solvate (e.g., a hydrate) thereof, is administered twice a day.

In some aspects, the method comprises administering to the subject the compound of formula (I), or a pharmaceutically acceptable salt thereof, at a dose of 4.5 mg; and ruxolitinib, or a pharmaceutically acceptable salt and/or solvate (e.g., a hydrate) thereof, at a dose of 15 mg. In some aspects, the ruxolitinib, or the pharmaceutically acceptable salt and/or solvate (e.g., a hydrate) thereof, is administered twice a day.

In some aspects, the method comprises administering to the subject the compound of formula (I), or a pharmaceutically acceptable salt thereof, at a dose of 2.0 mg; and ruxolitinib, or a pharmaceutically acceptable salt and/or solvate (e.g., a hydrate) thereof, at a dose of 30 mg. In some aspects, the ruxolitinib, or the pharmaceutically acceptable salt and/or solvate (e.g., a hydrate) thereof, is administered twice a day.

In some aspects, the subject treated with the compound of formula (I), or a pharmaceutically acceptable salt thereof, at a dose of 0.75 mg; and ruxolitinib, or a pharmaceutically acceptable salt and/or solvate (e.g., a hydrate) thereof, at a dose of 5 mg, 10 mg, 15 mg, or 20 mg is ruxolitinib-naïve and naïve with regard to other JAK inhibitors. In some aspects, the ruxolitinib, or the pharmaceutically acceptable salt and/or solvate (e.g., a hydrate) thereof, is administered twice a day.

In some aspects, the subject treated with the compound of formula (I), or a pharmaceutically acceptable salt thereof, at a dose of 0.75 mg; and ruxolitinib, or a pharmaceutically acceptable salt and/or solvate (e.g., a hydrate) thereof, at a starting dose of 15 mg is ruxolitinib-naïve and naïve with regard to other JAK inhibitors. In some aspects, the ruxolitinib, or the pharmaceutically acceptable salt and/or solvate (e.g., a hydrate) thereof, is administered twice a day.

In some aspects, the subject treated with the compound of formula (I), or a pharmaceutically acceptable salt thereof, at a dose of 0.75 mg; and ruxolitinib, or a pharmaceutically acceptable salt and/or solvate (e.g., a hydrate) thereof, at a dose of 15 mg is ruxolitinib-naïve and naïve with regard to other JAK inhibitors. In some aspects, the ruxolitinib, or the pharmaceutically acceptable salt and/or solvate (e.g., a hydrate) thereof, is administered twice a day.

In some aspects, the subject treated with the compound of formula (I), or a pharmaceutically acceptable salt thereof, at a dose of 1.0 mg; and ruxolitinib, or a pharmaceutically acceptable salt and/or solvate (e.g., a hydrate) thereof, at a dose of 5 mg, 10 mg, 15 mg, or 20 mg is ruxolitinib-naïve and naïve with regard to other JAK inhibitors. In some aspects, the ruxolitinib, or the pharmaceutically acceptable salt and/or solvate (e.g., a hydrate) thereof, is administered twice a day.

In some aspects, the subject treated with the compound of formula (I), or a pharmaceutically acceptable salt thereof, at a dose of 1.0 mg; and ruxolitinib, or a pharmaceutically acceptable salt and/or solvate (e.g., a hydrate) thereof, at a starting dose of 15 mg is ruxolitinib-naïve and naïve with regard to other JAK inhibitors. In some aspects, the ruxolitinib, or the pharmaceutically acceptable salt and/or solvate (e.g., a hydrate) thereof, is administered twice a day.

In some aspects, the subject treated with the compound of formula (I), or a pharmaceutically acceptable salt thereof, at a dose of 1.0 mg; and ruxolitinib, or a pharmaceutically acceptable salt and/or solvate (e.g., a hydrate) thereof, at a dose of 15 mg is ruxolitinib-naïve and naïve with regard to other JAK inhibitors. In some aspects, the ruxolitinib, or the pharmaceutically acceptable salt and/or solvate (e.g., a hydrate) thereof, is administered twice a day.

In some aspects, the subject treated with the compound of formula (I), or a pharmaceutically acceptable salt thereof, at a dose of 1.25 mg; and ruxolitinib, or a pharmaceutically acceptable salt and/or solvate (e.g., a hydrate) thereof, at a dose of 5 mg, 10 mg, 15 mg, or 20 mg is ruxolitinib-naïve and naïve with regard to other JAK inhibitors. In some aspects, the ruxolitinib, or the pharmaceutically acceptable salt and/or solvate (e.g., a hydrate) thereof, is administered twice a day.

In some aspects, the subject treated with the compound of formula (I), or a pharmaceutically acceptable salt thereof, at a dose of 1.25 mg; and ruxolitinib, or a pharmaceutically acceptable salt and/or solvate (e.g., a hydrate) thereof, at a starting dose of 15 mg is ruxolitinib-naïve and naïve with regard to other JAK inhibitors. In some aspects, the ruxolitinib, or the pharmaceutically acceptable salt and/or solvate (e.g., a hydrate) thereof, is administered twice a day.

In some aspects, the subject treated with the compound of formula (I), or a pharmaceutically acceptable salt thereof, at a dose of 1.25 mg; and ruxolitinib, or a pharmaceutically acceptable salt and/or solvate (e.g., a hydrate) thereof, at a dose of 15 mg is ruxolitinib-naïve and naïve with regard to other JAK inhibitors. In some aspects, the ruxolitinib, or the pharmaceutically acceptable salt and/or solvate (e.g., a hydrate) thereof, is administered twice a day.

In some aspects, the subject treated with the compound of formula (I), or a pharmaceutically acceptable salt thereof, at a dose of 1.5 mg; and ruxolitinib, or a pharmaceutically acceptable salt and/or solvate (e.g., a hydrate) thereof, at a dose of 5 mg, 10 mg, 15 mg, or 20 mg is ruxolitinib-naïve and naïve with regard to other JAK inhibitors. In some aspects, the ruxolitinib, or the pharmaceutically acceptable salt and/or solvate (e.g., a hydrate) thereof, is administered twice a day.

In some aspects, the subject treated with the compound of formula (I), or a pharmaceutically acceptable salt thereof, at a dose of 1.5 mg; and ruxolitinib, or a pharmaceutically acceptable salt and/or solvate (e.g., a hydrate) thereof, at a starting dose of 15 mg is ruxolitinib-naïve and naïve with regard to other JAK inhibitors. In some aspects, the ruxolitinib, or the pharmaceutically acceptable salt and/or solvate (e.g., a hydrate) thereof, is administered twice a day.

In some aspects, the subject treated with the compound of formula (I), or a pharmaceutically acceptable salt thereof, at a dose of 1.5 mg; and ruxolitinib, or a pharmaceutically acceptable salt and/or solvate (e.g., a hydrate) thereof, at a dose of 15 mg is ruxolitinib-naïve and naïve with regard to other JAK inhibitors. In some aspects, the ruxolitinib, or the pharmaceutically acceptable salt and/or solvate (e.g., a hydrate) thereof, is administered twice a day.

In some aspects, the subject treated with the compound of formula (I), or a pharmaceutically acceptable salt thereof, at a dose of 2.0 mg; and ruxolitinib, or a pharmaceutically acceptable salt and/or solvate (e.g., a hydrate) thereof, at a dose of 5 mg, 10 mg, 15 mg, or 20 mg is ruxolitinib-naïve and naïve with regard to other JAK inhibitors. In some aspects, the ruxolitinib, or the pharmaceutically acceptable salt and/or solvate (e.g., a hydrate) thereof, is administered twice a day.

In some aspects, the subject treated with the compound of formula (I), or a pharmaceutically acceptable salt thereof, at a dose of 2.0 mg; and ruxolitinib, or a pharmaceutically acceptable salt and/or solvate (e.g., a hydrate) thereof, at a starting dose of 15 mg is ruxolitinib-naïve and naïve with regard to other JAK inhibitors. In some aspects, the ruxolitinib, or the pharmaceutically acceptable salt and/or solvate (e.g., a hydrate) thereof, is administered twice a day.

In some aspects, the subject treated with the compound of formula (I), or a pharmaceutically acceptable salt thereof, at a dose of 2.0 mg; and ruxolitinib, or a pharmaceutically acceptable salt and/or solvate (e.g., a hydrate) thereof, at a dose of 15 mg is ruxolitinib-naïve and naïve with regard to other JAK inhibitors. In some aspects, the ruxolitinib, or the pharmaceutically acceptable salt and/or solvate (e.g., a hydrate) thereof, is administered twice a day.

In some aspects, the subject treated with the compound of formula (I), or a pharmaceutically acceptable salt thereof, at a dose of 3.0 mg; and ruxolitinib, or a pharmaceutically acceptable salt and/or solvate (e.g., a hydrate) thereof, at a dose of 5 mg, 10 mg, 15 mg, or 20 mg is ruxolitinib-naïve and naïve with regard to other JAK inhibitors. In some aspects, the ruxolitinib, or the pharmaceutically acceptable salt and/or solvate (e.g., a hydrate) thereof, is administered twice a day.

In some aspects, the subject treated with the compound of formula (I), or a pharmaceutically acceptable salt thereof, at a dose of 3.0 mg; and ruxolitinib, or a pharmaceutically acceptable salt and/or solvate (e.g., a hydrate) thereof, at a starting dose of 15 mg is ruxolitinib-naïve and naïve with regard to other JAK inhibitors. In some aspects, the ruxolitinib, or the pharmaceutically acceptable salt and/or solvate (e.g., a hydrate) thereof, is administered twice a day.

In some aspects, the subject treated with the compound of formula (I), or a pharmaceutically acceptable salt thereof, at a dose of 3.0 mg; and ruxolitinib, or a pharmaceutically acceptable salt and/or solvate (e.g., a hydrate) thereof, at a dose of 15 mg is ruxolitinib-naïve and naïve with regard to other JAK inhibitors. In some aspects, the ruxolitinib, or the pharmaceutically acceptable salt and/or solvate (e.g., a hydrate) thereof, is administered twice a day.

In some aspects, the subject treated with the compound of formula (I), or a pharmaceutically acceptable salt thereof, at a dose of 4.0 mg; and ruxolitinib, or a pharmaceutically acceptable salt and/or solvate (e.g., a hydrate) thereof, at a dose of 5 mg, 10 mg, 15 mg, or 20 mg is ruxolitinib-naïve and naïve with regard to other JAK inhibitors. In some aspects, the ruxolitinib, or the pharmaceutically acceptable salt and/or solvate (e.g., a hydrate) thereof, is administered twice a day.

In some aspects, the subject treated with the compound of formula (I), or a pharmaceutically acceptable salt thereof, at a dose of 4.0 mg; and ruxolitinib, or a pharmaceutically acceptable salt and/or solvate (e.g., a hydrate) thereof, at a starting dose of 15 mg is ruxolitinib-naïve and naïve with regard to other JAK inhibitors. In some aspects, the ruxolitinib, or the pharmaceutically acceptable salt and/or solvate (e.g., a hydrate) thereof, is administered twice a day.

In some aspects, the subject treated with the compound of formula (I), or a pharmaceutically acceptable salt thereof, at a dose of 4.0 mg; and ruxolitinib, or a pharmaceutically acceptable salt and/or solvate (e.g., a hydrate) thereof, at a dose of 15 mg is ruxolitinib-naïve and naïve with regard to other JAK inhibitors. In some aspects, the ruxolitinib, or the pharmaceutically acceptable salt and/or solvate (e.g., a hydrate) thereof, is administered twice a day.

In some aspects, the subject treated with the compound of formula (I), or a pharmaceutically acceptable salt thereof, at a dose of 4.5 mg; and ruxolitinib, or a pharmaceutically acceptable salt and/or solvate (e.g., a hydrate) thereof, at a dose of 5 mg, 10 mg, 15 mg, or 20 mg is ruxolitinib-naïve and naïve with regard to other JAK inhibitors. In some aspects, the ruxolitinib, or the pharmaceutically acceptable salt and/or solvate (e.g., a hydrate) thereof, is administered twice a day.

In some aspects, the subject treated with the compound of formula (I), or a pharmaceutically acceptable salt thereof, at a dose of 4.5 mg; and ruxolitinib, or a pharmaceutically acceptable salt and/or solvate (e.g., a hydrate) thereof, at a starting dose of 15 mg is ruxolitinib-naïve and naïve with regard to other JAK inhibitors. In some aspects, the ruxolitinib, or the pharmaceutically acceptable salt and/or solvate (e.g., a hydrate) thereof, is administered twice a day.

In some aspects, the subject treated with the compound of formula (I), or a pharmaceutically acceptable salt thereof, at a dose of 4.5 mg; and ruxolitinib, or a pharmaceutically acceptable salt and/or solvate (e.g., a hydrate) thereof, at a dose of 15 mg is ruxolitinib-naïve and naïve with regard to other JAK inhibitors. In some aspects, the ruxolitinib, or the pharmaceutically acceptable salt and/or solvate (e.g., a hydrate) thereof, is administered twice a day.

In some aspects, the subject treated with the compound of formula (I), or a pharmaceutically acceptable salt thereof, at a dose of 2.0 mg; and ruxolitinib, or a pharmaceutically acceptable salt and/or solvate (e.g., a hydrate) thereof, at a dose of 30 mg is ruxolitinib-naïve and naïve with regard to other JAK inhibitors. In some aspects, the ruxolitinib, or the pharmaceutically acceptable salt and/or solvate (e.g., a hydrate) thereof, is administered twice a day.

Pharmaceutical Compositions

The BET inhibitors and the JAK inhibitors used in the methods and kits described herein can be formulated into pharmaceutical compositions suitable for administration. The pharmaceutical compositions may comprise pharmaceutically acceptable excipients. A pharmaceutically acceptable excipient, as used herein, includes, but are not limited to, any and all solvents, dispersion media, or other liquid vehicles, dispersion or suspension aids, diluents, granulating and/or dispersing agents, surface active agents, isotonic agents, thickening or emulsifying agents, preservatives, binders, lubricants or oil, coloring, sweetening or flavoring agents, stabilizers, antioxidants, antimicrobial or antifungal agents, osmolality adjusting agents, pH adjusting agents, buffers, chelants, cyoprotectants, and/or bulking agents, as suited to the particular dosage form desired. Various excipients for formulating pharmaceutical compositions and techniques for preparing the composition are known in the art (see Remington: The Science and Practice of Pharmacy, 21st Ed., A. R. Gennaro (Lippincott, Williams & Wilkins, Baltimore, MD), 2006; incorporated by reference in its entirety)

Any of the therapeutic agents described herein can be in the form of a pharmaceutically acceptable salt. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington: The Science and Practice of Pharmacy, $22^{nd}$ Edition, Allen, L. V. Jr., Ed.; Pharmaceutical Press, London, UK (2012), the disclosure of which is hereby incorporated by reference.

The pharmaceutical compositions may comprise pharmaceutically acceptable carriers. As used herein, "pharmaceutically acceptable carrier" refers to a material that is compatible with a recipient subject (a human) and is suitable for delivering an active agent to the target site without terminating the activity of the agent. The toxicity or adverse effects, if any, associated with the carrier preferably are commensurate with a reasonable risk/benefit ratio for the intended use of the active agent.

Pharmaceutically acceptable carriers that can be used in these compositions include ion exchangers, alumina, aluminum stearate, lecithin, serum proteins, such as human serum albumin, buffer substances such as phosphates or carbonates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose based substances, polyethylene glycol, sodium carboxymethylcellulose, polyacrylates, waxes, polyethylene polyoxypropylene block polymers, polyethylene glycol and wool fat.

The pharmaceutical compositions for use in the methods of the present disclosure can be manufactured by methods well known in the art such as conventional granulating, mixing, dissolving, encapsulating, lyophilizing, or emulsifying processes, among others. Compositions can be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may contain stabilizers, pH modifiers, surfactants, solubilizing agents, bioavailability modifiers and combinations of these. These pharmaceutical compositions are formulated for pharmaceutical administration to a human being. Such compositions can be administered orally, parenterally, by inhalation spray, topically, rectally, nasally, buccally, vaginally or via an implanted reservoir. The term "parenteral" as used herein includes subcutaneous, intravenous, intraperitoneal, intramuscular, intra articular, intra synovial, intrasternal, intrathecal, intrahepatic, intralesional and intracranial injection or infusion techniques. In some aspects, the compositions are administered orally, intravenously or subcutaneously. In some aspects, the compositions are administered orally. In some aspects, the compositions are administered intravenously. In some aspects, the intravenous administration can be intravenous infusion or intravenous injection. In some aspects, the compositions are administered by an intravenous infusion. In some aspects, the compositions are administered by an intravenous injection. In some aspects, the compositions are administered by subcutaneous injection. In some aspects, the compositions are administered by intravenous infusion and then subsequently administered by subcutaneous injection. These formulations can be designed to be short acting, fast releasing, or long acting. Furthermore, the compositions can be administered in a local rather than systemic means, such as administration (e.g., by injection) at a tumor site.

Pharmaceutical formulations can be prepared as liquid suspensions or solutions using a liquid, such as an oil, water, an alcohol, and combinations of these. Solubilizing agents such as cyclodextrins can be included. Pharmaceutically suitable surfactants, suspending agents, or emulsifying agents, can be added for oral or parenteral administration. Suspensions may include oils, such as peanut oil, sesame oil, cottonseed oil, corn oil and olive oil. Suspension preparations may also contain esters of fatty acids such as ethyl oleate, isopropyl myristate, fatty acid glycerides and acetylated fatty acid glycerides. Suspension formulations may include alcohols, such as ethanol, isopropyl alcohol, hexadecyl alcohol, glycerol and propylene glycol; ethers, such as poly(ethyleneglycol); petroleum hydrocarbons such as mineral oil and petrolatum; and water.

Sterile injectable forms of these pharmaceutical compositions can be aqueous or oleaginous suspensions. These suspensions can be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3 butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono or di glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long chain alcohol diluent or dispersant, such as carboxymethyl cellulose or similar dispersing agents which are commonly used in the formulation of pharmaceutically acceptable dosage forms including emulsions and suspensions. Other commonly used surfactants, such as sorbitan alkyl esters, such as Tweens or Spans, and other emulsifying agents or bioavailability enhancers which are commonly used in the manufacture of pharmaceutically acceptable solid, liquid, or other dosage forms may also be used for the purposes of formulation. Compounds can be formulated for parenteral administration by injection such as by bolus injection or continuous infusion. A unit dosage form for injection can be in ampoules or in multi dose containers.

These pharmaceutical compositions can be orally administered in any orally acceptable dosage form including capsules, tablets, aqueous suspensions or solutions. When aqueous suspensions are required for oral use, the active ingredient is combined with emulsifying and suspending agents. If desired, certain sweetening, flavoring or coloring agents may also be added. For oral administration in a capsule form, useful diluents include lactose and dried cornstarch. In the case of tablets for oral use, carriers that are commonly used include lactose and corn starch. Lubricating agents, such as magnesium stearate, are also typically added. Coatings can be used for a variety of purposes, e.g., to mask taste, to affect the site of dissolution or absorption, or to prolong drug action. Coatings can be applied to a tablet or to granulated particles for use in a capsule.

Alternatively, these pharmaceutical compositions can be administered in the form of suppositories for rectal administration. These can be prepared by mixing the agent with a suitable non irritating excipient which is solid at room temperature but liquid at rectal temperature and therefore will melt in the rectum to release the drug. Such materials include cocoa butter, beeswax and polyethylene glycols.

These pharmaceutical compositions may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically transdermal patches may also be used. For topical applications, the pharmaceutical compositions can be formulated in a suitable ointment containing the active component suspended or dissolved in one or more carriers. Carriers for topical administration of the compounds of the present disclosure include mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active component(s) suspended or dissolved in one or more pharmaceutically acceptable carriers. Suitable carriers include mineral oil, sorbitan monostearate, polysorbate 60, cetyl esters wax, cetearyl alcohol, 2 octyldodecanol, benzyl alcohol and water.

For ophthalmic use, the pharmaceutical compositions can be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions can be formulated in an ointment such as petrolatum.

The pharmaceutical compositions may also be administered by nasal aerosol or inhalation. Such compositions are prepared according to techniques well known in the art of pharmaceutical formulation and can be prepared as solutions in saline, employing benzyl alcohol or other suitable preservatives, absorption promoters to enhance bioavailability, fluorocarbons, and/or other conventional solubilizing or dispersing agents.

In some aspects, a compound of formula (I), the compound of formula (I), is formulated as a solution for intravenous infusion. In some aspects, the compound of formula (I) is formulated in a solution with a buffering agent or a pH modifying agent, and a cyclodextrin, such as a beta-cyclodextrin. In some aspects, the solution includes phosphoric acid and Captisol (betadex sulfobutyl ether sodium) in water. In some aspects, the solution for intravenous infusion contains 10 mg/mL of the compound of formula (I).

In some aspects, the compound of formula (I) is formulated as a drug product, wherein the drug product contains the compound of formula (I) in a solution of phosphoric acid and Captisol (betadex sulfobutyl ether sodium) in water. In some aspects, the drug product is packaged with a volume of 10 mL of the compound of formula (I) sterile solution.

In some aspects, the JAK inhibitor is formulated as a solution for injection.

In some aspects, the present disclosure relates to a pharmaceutical composition for use in treating or preventing cancer in a subject in need thereof comprising the compound of formula (I), or a pharmaceutically acceptable salt thereof, and a JAK inhibitor. In some aspects, the present disclosure relates to a pharmaceutical composition for use in treating or preventing cancer in a subject in need thereof comprising the compound of formula (I), or a pharmaceutically acceptable salt thereof, and a JAK inhibitor. In some aspects, the pharmaceutical composition is formulated for simultaneous or sequential administration of said the compound of formula (I), or a pharmaceutically acceptable salt thereof. In some aspects, the pharmaceutical composition is formulated for simultaneous or sequential administration of said the compound of formula (I), or a pharmaceutically acceptable salt thereof, said JAK inhibitor.

Kits

In some aspects, the BET inhibitor or the JAK inhibitor described herein can be manufactured for inclusion in a kit. A "kit" is any article of manufacture (e.g., a package or container) comprising at least one reagent or chemotherapeutic agent. A kit for use in the methods herein may comprise a BET inhibitor, such as the compound of formula (I), or a pharmaceutically acceptable salt thereof. In some aspects, the kit may further include a JAK inhibitor. In some aspects, the kit may include the compound of formula (I), or a pharmaceutically acceptable salt thereof, a JAK inhibitor. In some aspects, the kit may include one or more BET inhibitors or pharmaceutically acceptable salts thereof. In some aspects, the kit may include one or more JAK inhibitors.

In some aspects, the present disclosure relates to a kit comprising a medicament for use in treating cancer in a patient in need of such treatment. The kit comprises a medicament comprising a BET inhibitor, and instructions for administering the BET inhibitor and a JAK inhibitor; or the kit comprises a medicament comprising a JAK inhibitor, and instructions for administering the JAK inhibitor and a BET inhibitor. The kit may contain a medicament comprising a BET inhibitor and a JAK inhibitor, and instructions for administering the BET inhibitor and the JAK inhibitor.

EXAMPLES

Example 1-Antiproliferative Effects of Compound (I) and JAK Inhibitors in Myelofibrosis Cell Lines HEL92.1.7 and SET-2 are post-MPN secondary acute myeloid leukemia (sAML) cell lines that harbor the JAK2 V617F mutation and serve as cell line models of the malignant clones driving disease in MPNs.

HEL92.1.792.1.7 (post-MPN sAML), a homozygous mutant (V617F), SET-2 (post-MPN sAML), a heterozygous mutant (V617F), were cultured in Roswell Park Memorial Institute (RPMI) 1640 medium (ATCC) supplemented with 10% or 20% fetal b ovine serum (FBS) (Corning) for HEL92.1.792.17 or SET-2 respectively, 2 mM L-glutamine (L-glu) (Gibco), and non-essential amino acid 1× (NEAA) cell culture supplement (Gibco). WI-38 primary lung fibroblastWI-38 were cultured in Eagle's Minimum Essential Medium (EMEM) (ATCC) with 10% FBS, 2 mM L-glu, and 1× NEAA. Cells were treated with the Compound (I) as a single agent and in combination with ruxolitinib (Rux) or fedratinib (Fed) to investigate the antiproliferative activity and cytotoxicity.

CellTiter-Glo® (CTG), a luminescent dye that measures adenosine-5'-triphosphate (ATP), was used to quantify the cell proliferation in the 3 cell types in duplicate. Compound (I) was pre-spotted into 384-well plates (diluted in final dimethyl sulfoxide [DMSO] concentration of 0.1% for assay volume of 50 µL). A 10-point dose-response starting at 1 M with a 4-fold dilution that included one DMSO point and nine drug points was tested for each cell line. The JAK inhibitors (JAKi) Rux and Fed were also pre-spotted at concentrations of 0, 0.03, 0.1, 0.3, and 0.6 µM and HEL92.1.7 constant for each 10-point the Compound (I) dose-response curve (DRC) to produce five compounds of formula (I) DRCs for each JAKi in each cell line.

A cell suspension volume of 50 µL at their respective seeding densities was added to 384-well plates containing Compound (I) plus JAKi. The effect of Compound (I) single agent or JAKi combination on the proliferation/viability of cells was assessed after 3 days of incubation. Twenty-five microliters of CTG per well was then dispensed to the cell suspension, and ATP released by viable cells was measured after a 30-minute incubation as relative luminescence units (RLU) using an EnVision plate reader (PerkinElmer, Covina, CA). Cytotoxicity was indicated by a lower ATP level in the media after 3-day drug treatment compared to the Day 0 ATP level. Day 0 CTG was read for HEL92.1. and SET-2 suspension cell lines while the Day 0 CTG read for WI-38 could not be read because it is an adherent cell line.

Percent growth (% Growth) was calculated with the equation [% Growth=(Day 5 RLU—Day 0 RLU)/(Day 0 RLU)] while percent DMSO (% DMSO) was calculated with the equation [% DMSO=(Treatment RLU/DMSO RLU)×100]. All data was analyzed by GraphPad Prism 7 with the XY analyses nonlinear regression curve fit using the parameters for "log(inhibitor) vs. response—Variable slope (four parameters)." Cytotoxicity was called if any part of the DRC CTG signal went below the Day 0 CTG read and cytostatic effects were indicated by the DRC CTG signal staying above the Day 0 line.

Combination analysis was performed with software Combenefit version 2.021. Combination matrix plots describing additivity effects were generated with the Highest Single-Agent (HSA) model, combination matrix plots describing synergy effects were generated with the Bliss model, and the HSA and Bliss scores for each combination matrix plot were tabulated. An arbitrary cut off-of 10 for HSA and Bliss scores was used to reflect significant additivity and synergy, respectively.

Finally, the relative 50% inhibitory concentrations (IC50) values of the Compound (I) dose-response curves (DRCs) plus Rux or Fed were plotted to illustrate any potency shifts that may support the calculated additivity/synergy scores. Additivity and synergy scores reported did not take into account antagonism numbers.

Figure 1B:
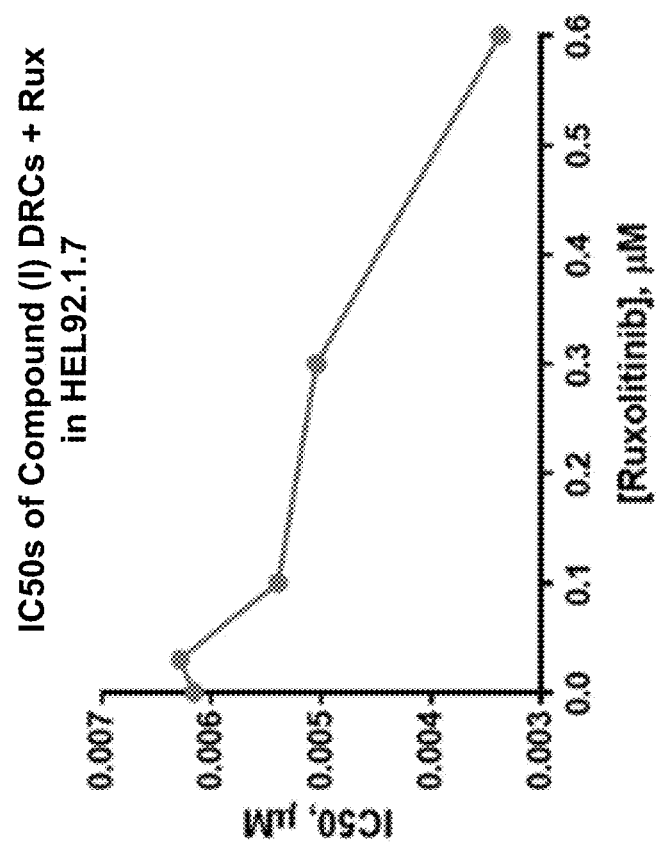
FIG. 1B shows a plot of viability IC50 values of Compound (I) dose-response curves in HEL92.1.7 cells at each concentration of ruxolitinib.

Compound (I) showed a single agent IC50 of 6.2 nM in HEL92.1.7 with cytotoxic effects; addition of fixed concentrations of Rux led to a potency shift (FIGS. 1A, 1).

Figure 2A:
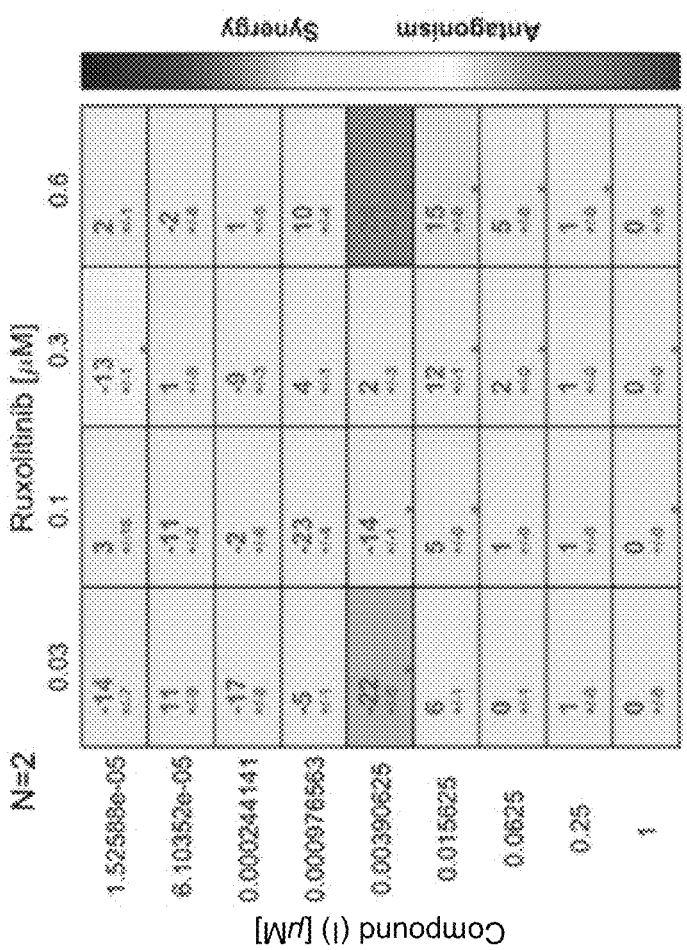
FIG. 2A shows a combination matrix plot for Compound (I) viability dose-response curves with ruxolitinib (Rux) in HEL92.1.7 cells describing additivity effects with a HSA model along with an HSA additivity score. Positive numbers show relative synergy while negative numbers show relative antagonism.
Figure 2B:
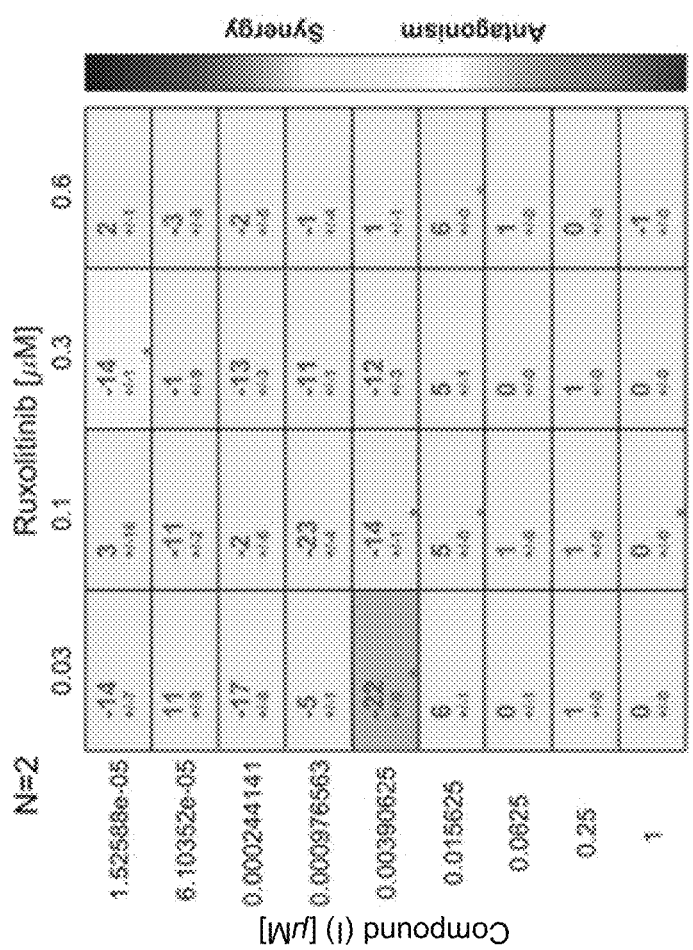
FIG. 2B shows a combination matrix plot describing antiproliferative synergy effects with a Bliss model along with a Bliss synergy score for Compound (I) dose-response curves with ruxolitinib in HEL92.1.7 cells. Positive numbers show relative synergy while negative numbers show relative antagonism.

Compound (I) dose-response curves with Rux in HEL92.1.7 showed additivity with a HSA additivity score of 15.8 (FIG. 2A) and a Bliss synergy score of 7.6 (FIG. 2B) with optimal dosing at 4 nM the compound of formula (I)+600 nM Rux.

Figure 3A:
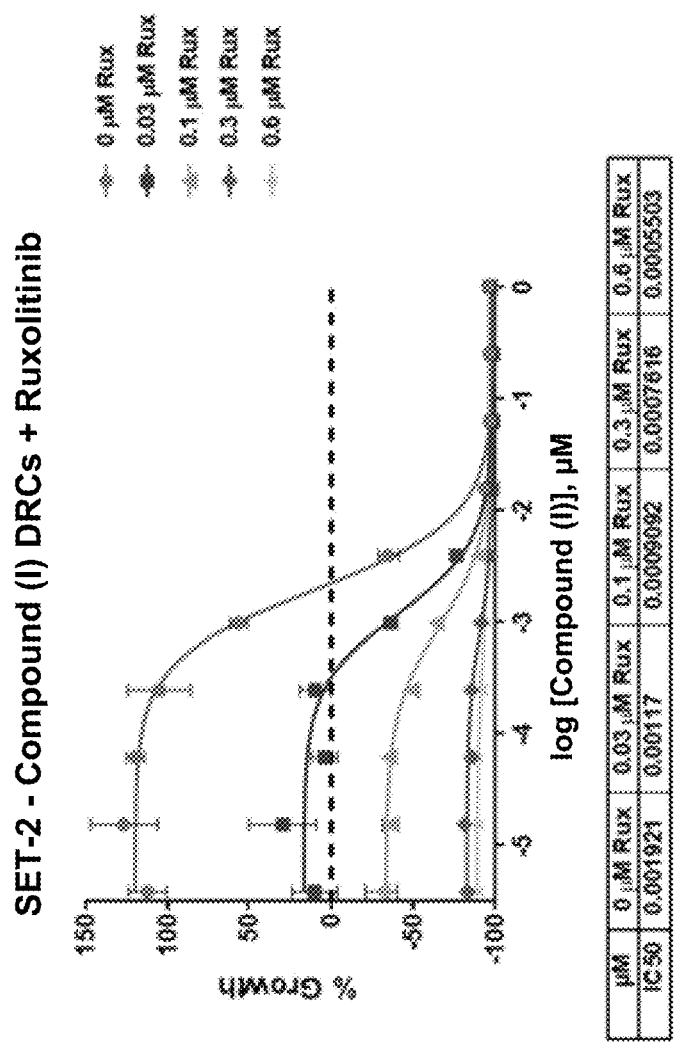
FIG. 3A shows a plot of Compound (I) viability dose-response curves with ruxolitinib (Rux) in SET-2 cells with IC50 values.
Figure 3B:
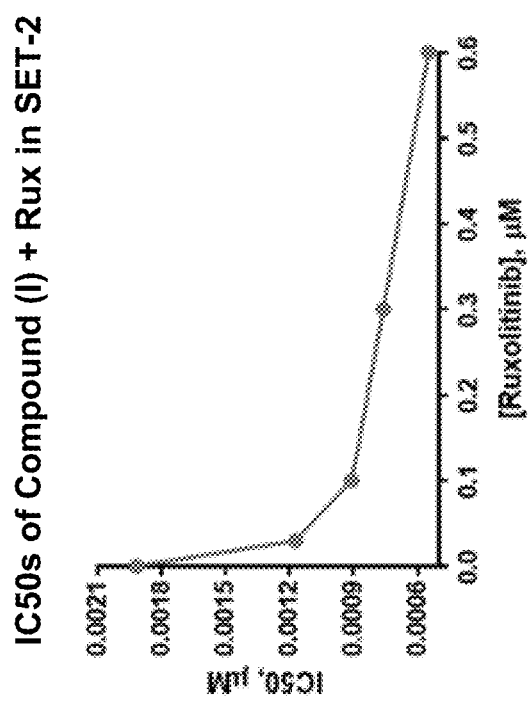
FIG. 3B shows a plot of viability IC50 values of Compound (I) dose-response curves in SET-2 cells at each concentration of ruxolitinib (Rux).

Compound (I) showed a single agent IC50 of 1.9 nM in SET-2 with cytotoxic effects; addition of fixed concentrations of Rux led to a potency shift (FIGS. 3A, 3B).

Figure 4A:
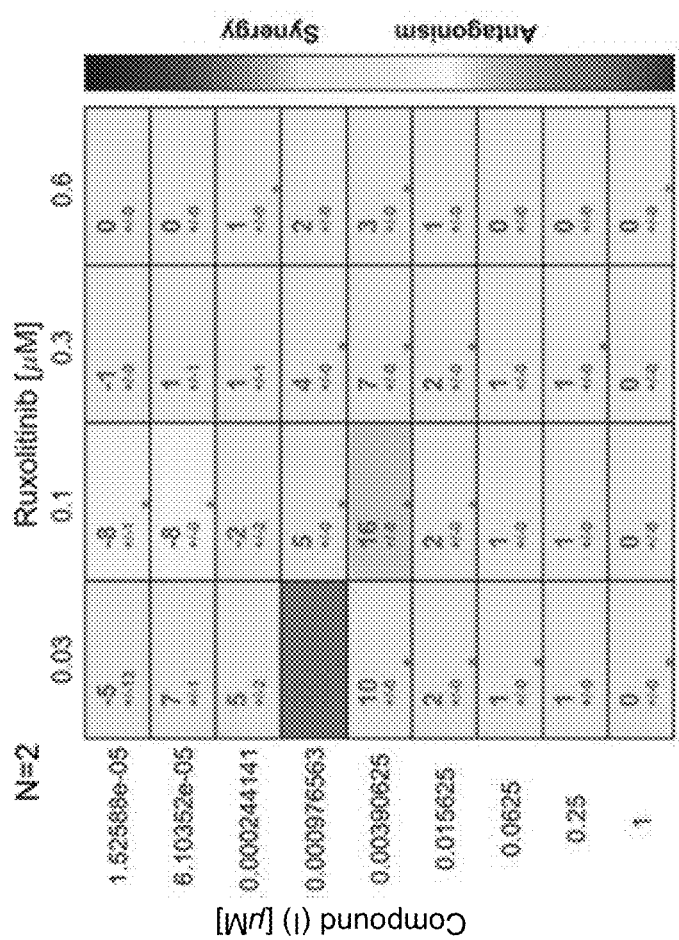
FIG. 4A shows a combination matrix plot for Compound (I) viability dose-response curves with ruxolitinib in SET-2 cells describing additivity effects with a HSA model along with an HSA additivity score. Positive numbers show relative synergy while negative numbers show relative antagonism.
Figure 4B:
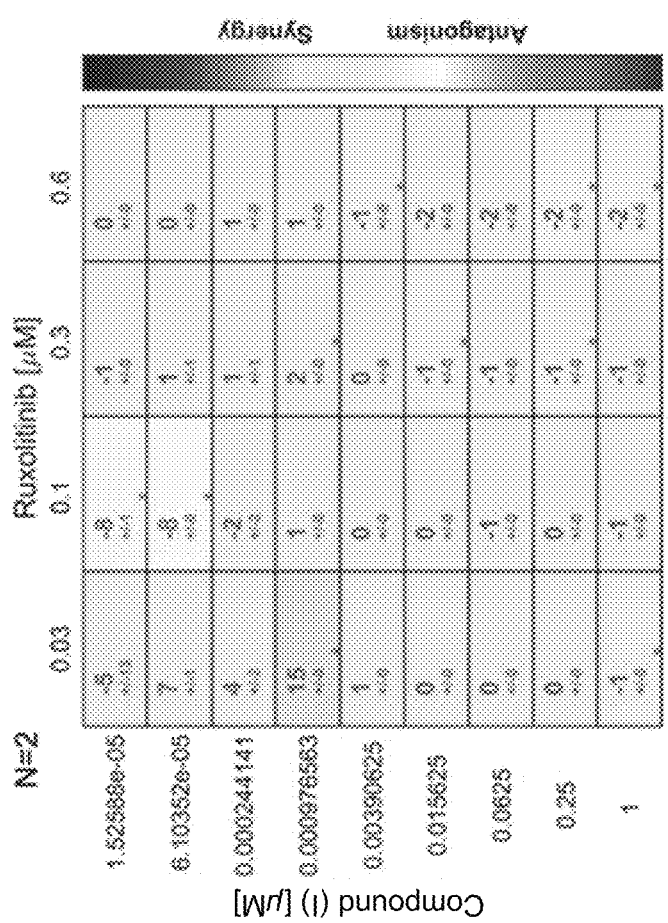
FIG. 4B shows a combination matrix plot describing antiproliferative synergy effects with a Bliss model along with a Bliss synergy score for Compound (I) dose-response curves with ruxolitinib in SET-2 cells. Positive numbers show relative synergy while negative numbers show relative antagonism.

Compound (I) dose-response curves with Rux in SET-2 showed additivity with a HSA additivity score of 20.5 (FIG. 4A) and a Bliss synergy score of 5.8 (FIG. 4B) with optimal dosing at 1 nM of Compound (I)+30 nM Rux.

Figure 5A:
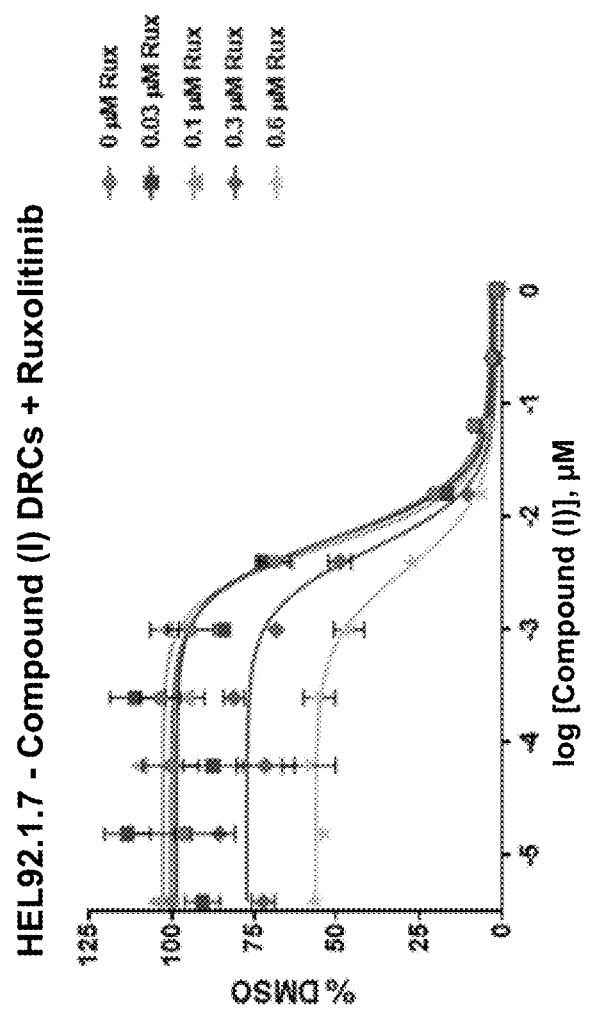
FIG. 5A shows a plot of Compound (I) viability dose-response curves with ruxolitinib (Rux) in HEL92.1.7 cells.
Figure 5B:
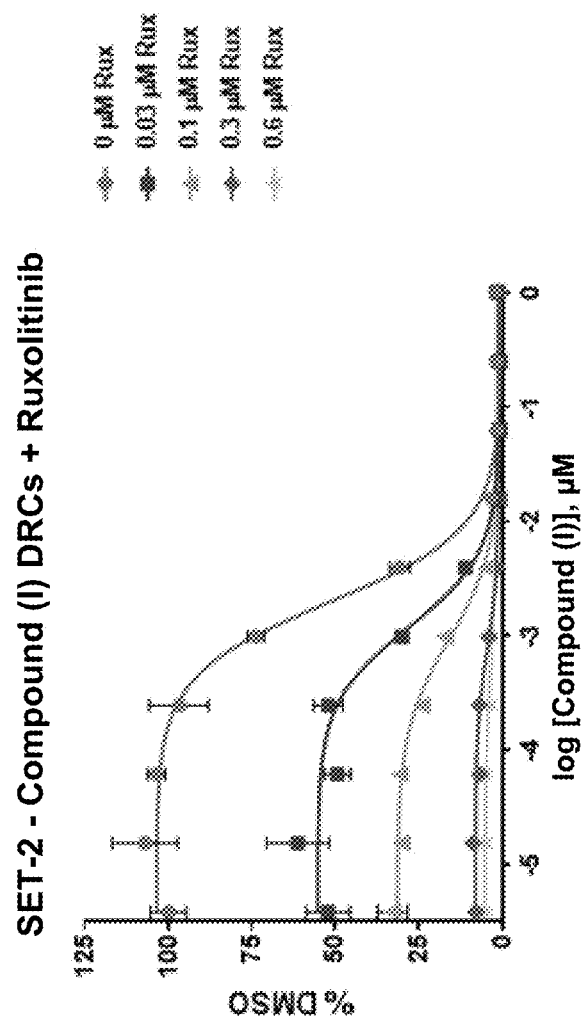
FIG. 5B shows a plot of Compound (I) viability dose-response curves with ruxolitinib (Rux) in SET-2 cells.
Figure 5C:
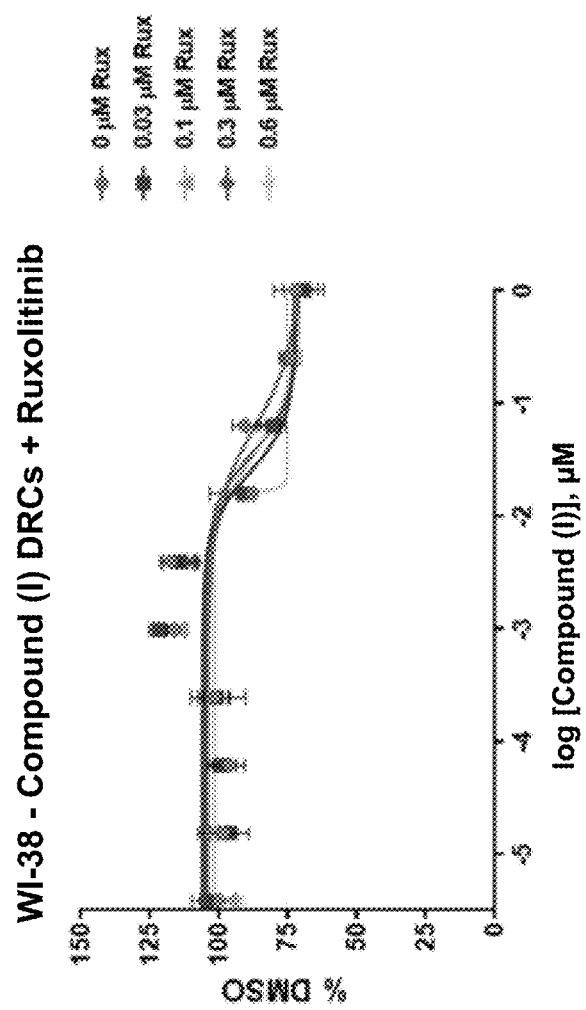
FIG. 5C shows a plot of the Compound (I) viability dose-response curves with ruxolitinib (Rux) in WI-38 cells.

A comparison of the Compound (I) dose-response curves with Rux in the JAK2 mutant post-MPN sAML lines (HEL92.1.792.1.7 and SET-2) with the JAK2 wildtype, adherent WI-38 fibroblast cell line suggested a possible therapeutic window for Compound (I) −/+Rux (FIGS. 5A, 5B, and 5C).

Figure 6A:
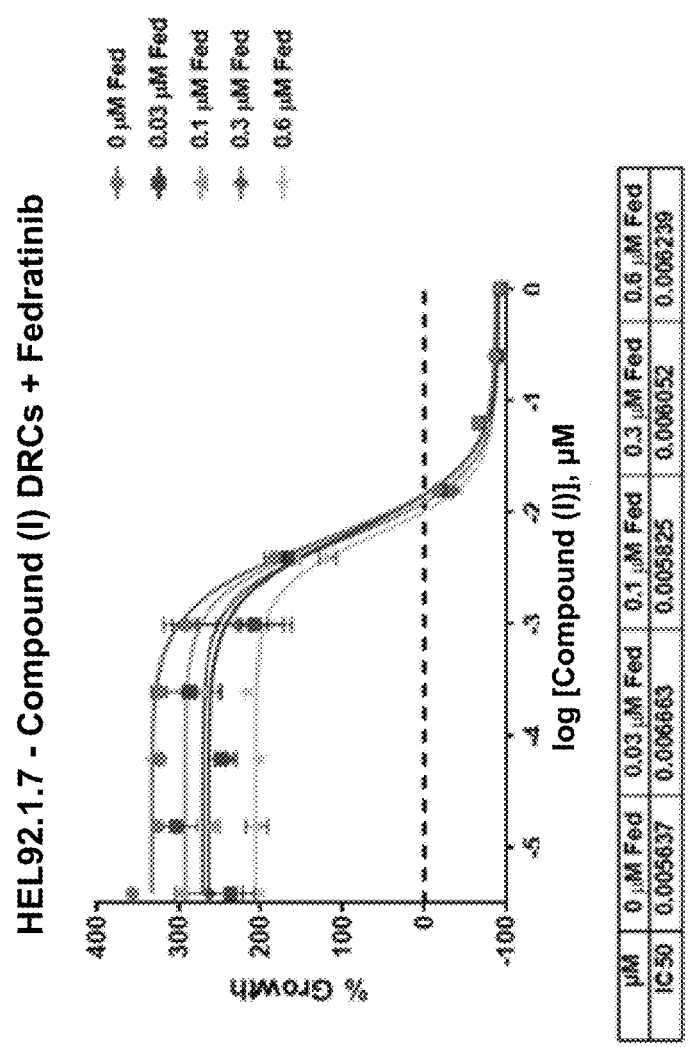
FIG. 6A shows a plot of Compound (I) viability dose-response curves with fedratinib (Fed) in HEL92.1.7 cells with IC50 values.
Figure 6B:
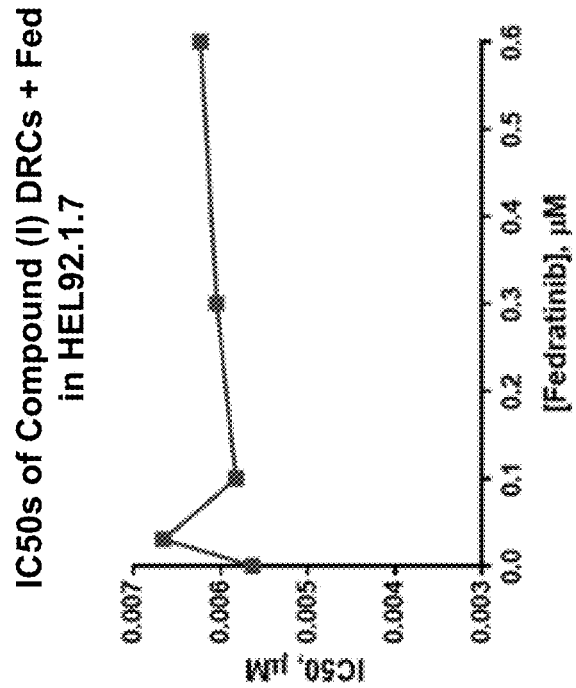
FIG. 6B shows a plot of IC50 values of Compound (I) viability dose-response curves in HEL92.1.7 cells at each concentration of fedratinib.

In a second set of experiments, Compound (I) showed a single agent IC50 of 5.6 nM in HEL92.1.792.1.7 with cytotoxic effects and addition of fixed concentrations of fedratinib (Fed) did not lead to a potency shift (FIGS. 6A, 6B).

Figure 7A:
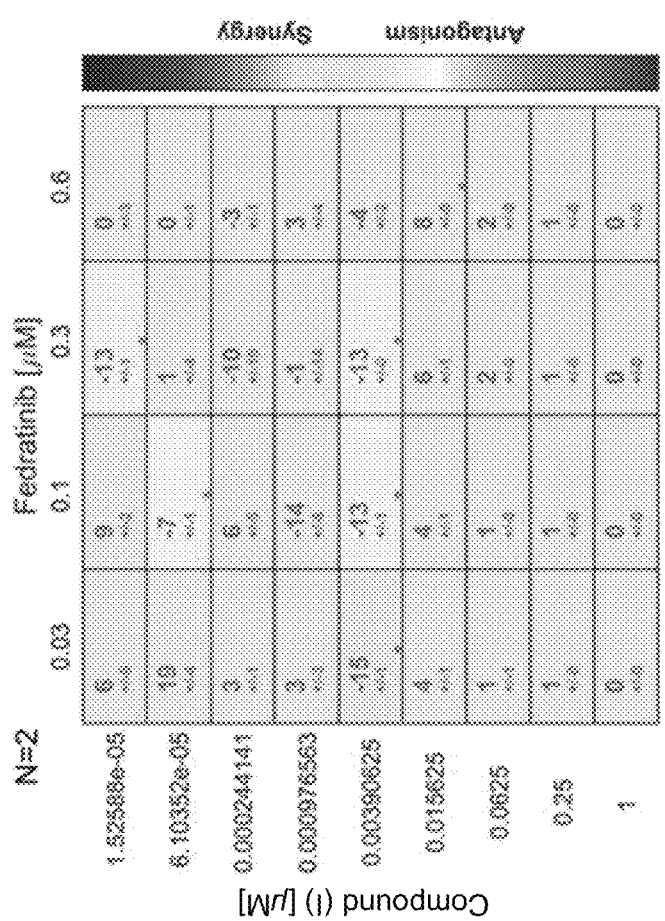
FIG. 7A shows a combination matrix plot for Compound (I) viability dose-response curves with fedratinib in HEL92.1.7 cells describing additivity effects with a HSA model along with an HSA additivity score. Positive numbers show relative synergy while negative numbers show relative antagonism.
Figure 7B:
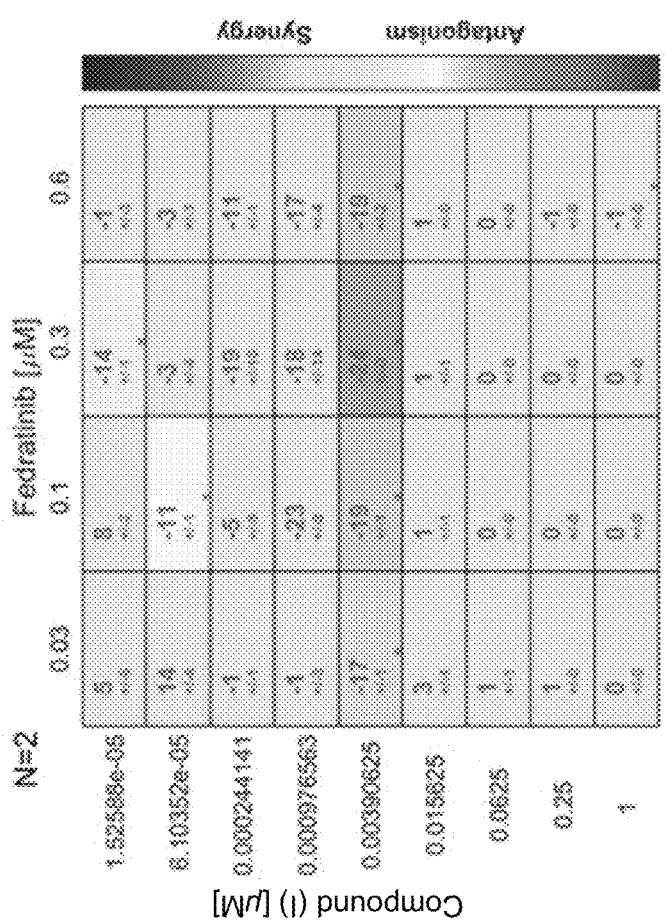
FIG. 7B shows a combination matrix plot describing antiproliferative synergy effects with a Bliss model along with a Bliss synergy score for Compound (I) dose-response curves with fedratinib in HEL92.1.7 cells. Positive numbers show relative synergy while negative numbers show relative antagonism.

The Compound (I) dose-response curves with Fed in HEL92.1.7 showed additivity with a HSA additivity with a HSA additivity score of 13.9 (FIG. 7A) and a Bliss synergy score of 5.4 (FIG. 7B) with optimal dosing at 16 nM Compound (I)+600 nM.

Figure 8A:
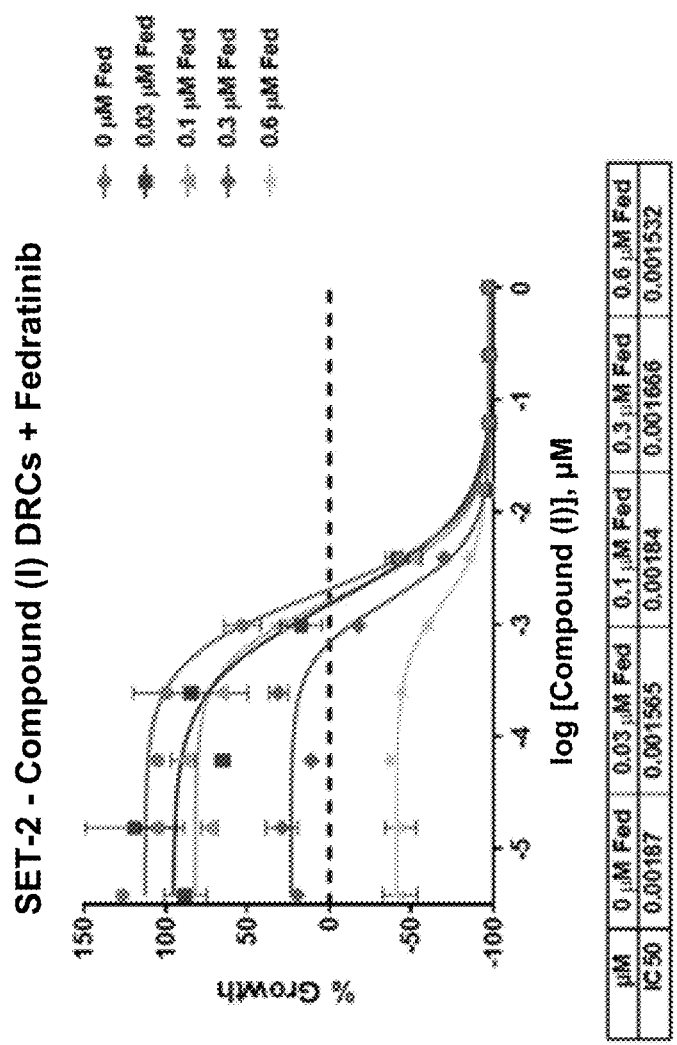
FIG. 8A shows a plot of Compound (I) viability dose-response curves with fedratinib (Fed) in SET-2 cells with IC50 values.
Figure 8B:
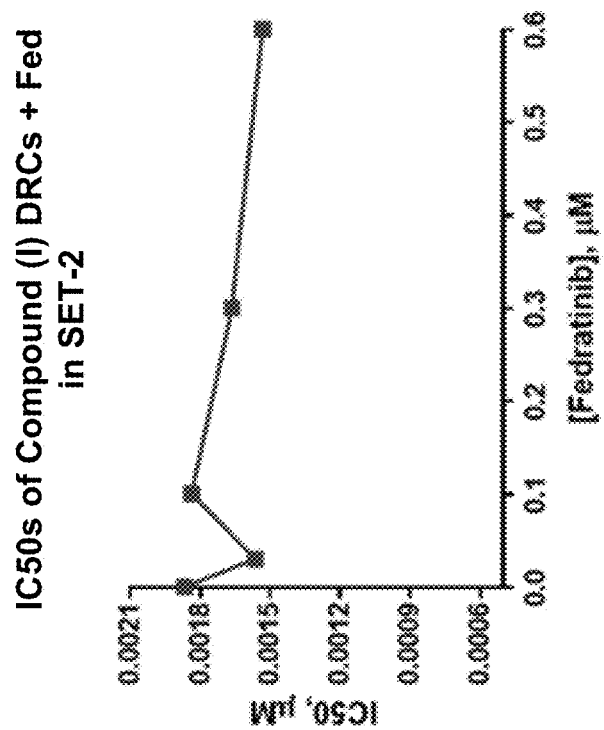
FIG. 8B shows a plot of IC50 values of Compound (I) viability dose-response curves in SET-2 cells at each concentration of fedratinib (Fed).

In SET-2 cells, Compound (I) showed a single agent IC50 of 1.9 nM with cytotoxic effects; addition of fixed concentrations of Fed led to a modest potency shift (FIGS. 8A, 8B).

Figure 9A:
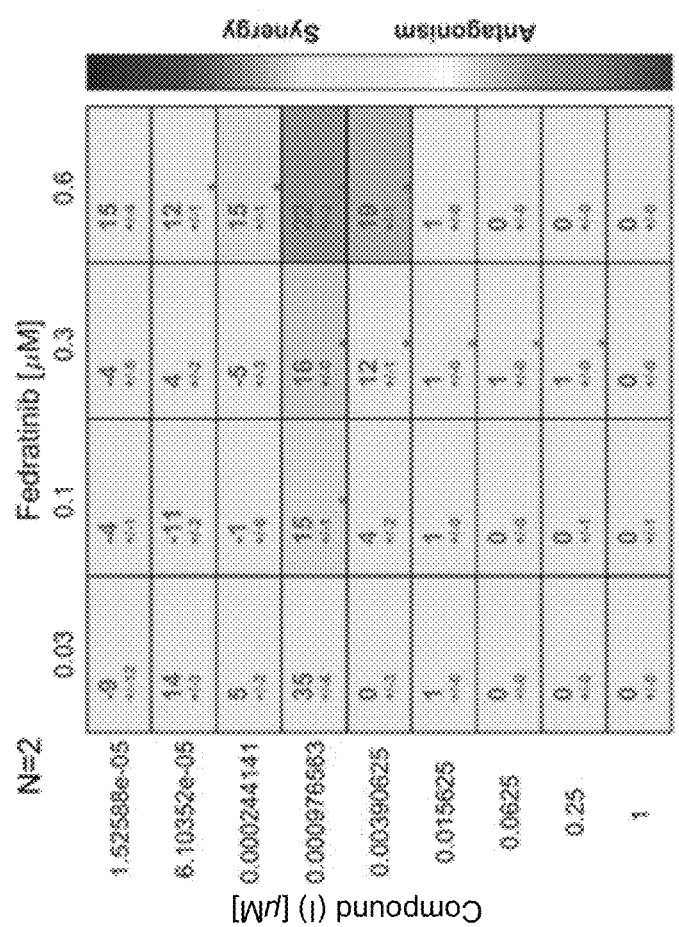
FIG. 9A shows a combination matrix plot for Compound (I) viability dose-response curves with fedratinib in SET-2 cells describing additivity effects with a HSA model along with an HSA additivity score. Positive numbers show relative synergy while negative numbers show relative antagonism.
Figure 9B:
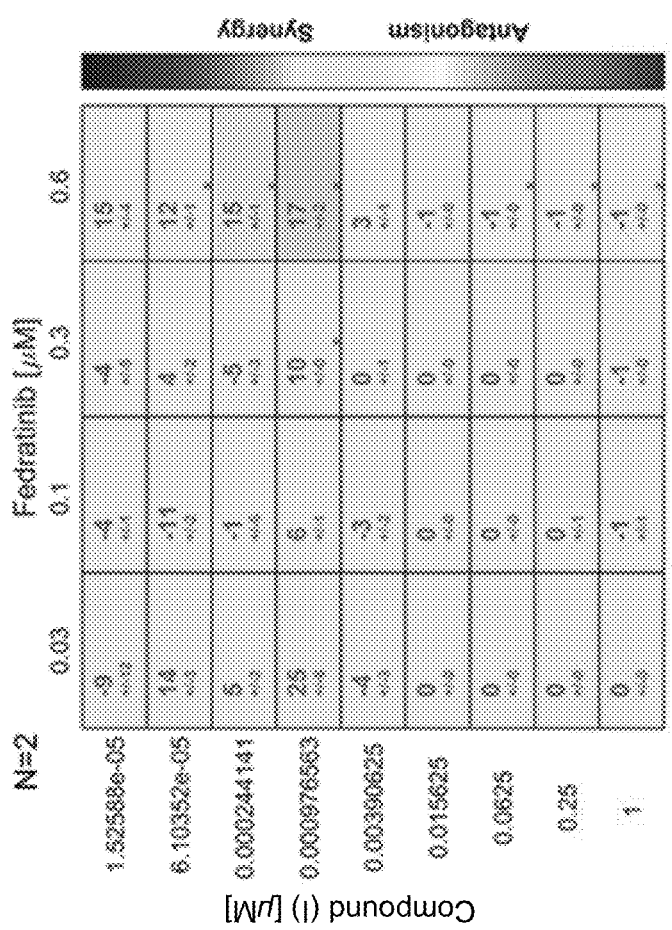
FIG. 9B shows a combination matrix plot describing antiproliferative synergy effects with a Bliss model along with a Bliss synergy score for Compound (I) dose-response curves with fedratinib in SET-2 cells. Positive numbers show relative synergy while negative numbers show relative antagonism.

Compound (I) dose-response curves with Fed in SET-2 showed synergy with a HSA additivity score of 28.9 (FIG. 9A) and a Bliss synergy score of 16.9 (FIG. 9B) with optimal dosing at 1 nM Compound (I)+600 nM Fed.

Figure 10A:
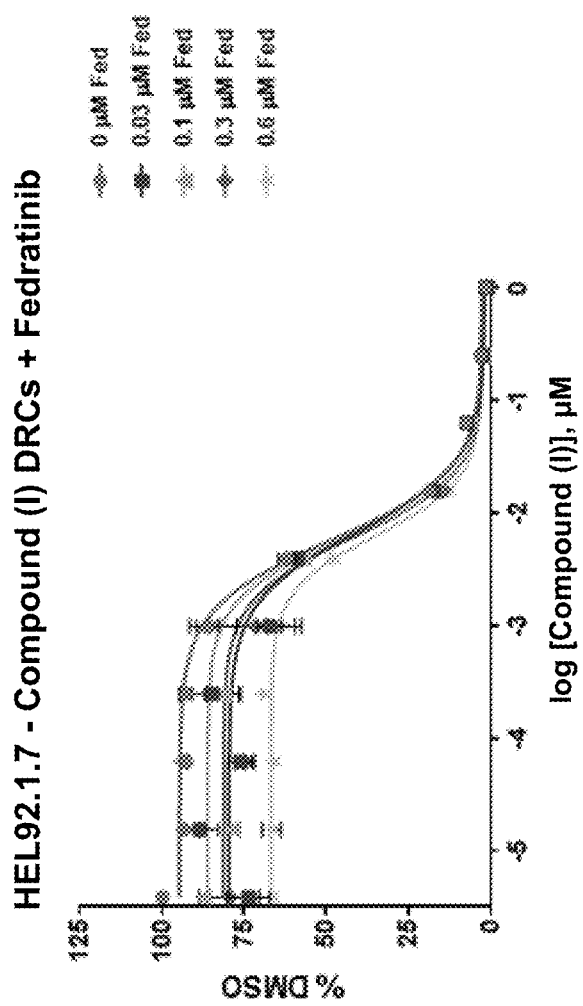
FIG. 10A shows a plot of Compound (I) viability dose-response curves with fedratinib (Fed) in HEL92.1.7 cells.
Figure 10B:
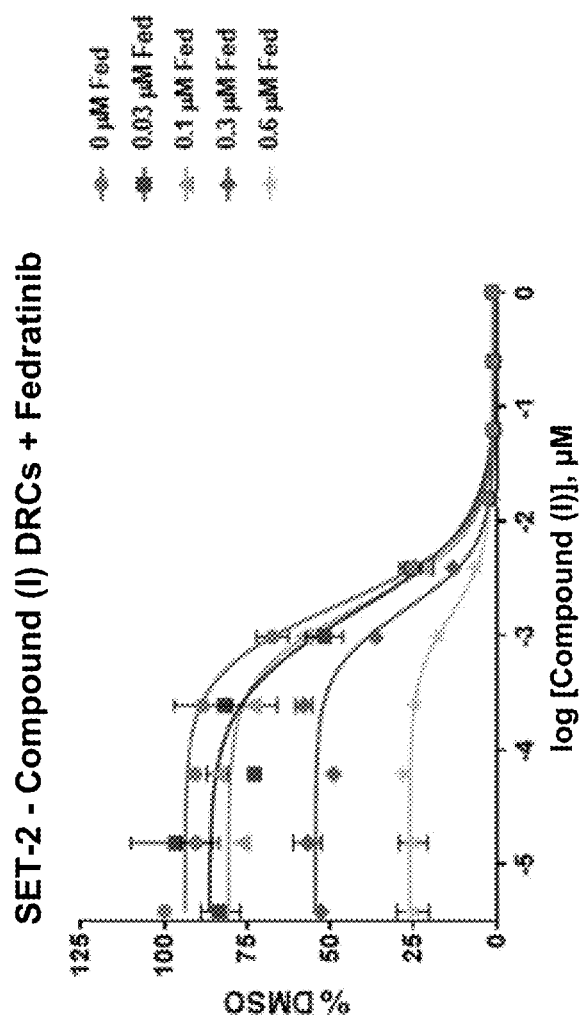
FIG. 10B shows a plot of Compound (I) viability dose-response curves with fedratinib (Fed) in SET-2 cells.
Figure 10C:
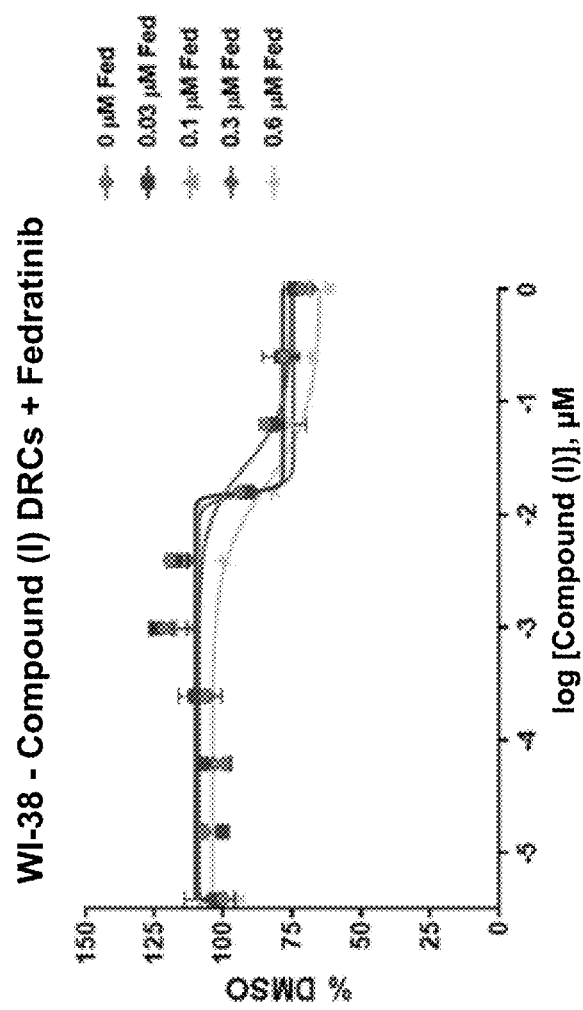
FIG. 10C shows a plot of Compound (I) viability dose-response curves with fedratinib (Fed) in WI-38 cells.

A comparison of Compound (I) dose-response curves with Fed in the JAK2 mutant post-MPN sAML lines HEL92.1.792.1.7 and SET-2 with the JAK2 wildtype, adherent WI-38 fibroblast cell line suggested a possible therapeutic window for Compound (I) −/+Fed (FIGS. 10A, 10B, and 10C).

These results demonstrated that Compound (I) was active as a single agent and in combination with Rux and Fed in post-MPN sAML cell lines HEL92.1.7 and SET-2.

Example 2-Evaluation of Compound (I) Efficacy as a Single Agent or in Combination with Fedratinib (Fed) or Ruxolitinib (Rux) on Myelofibrosis (MF) Primary Samples Bone marrow or peripheral blood mononuclear cells from myelofibrosis (MF) patients were directly seeded in semi-solid Methocult media (H3404) with Compound (I) alone, (at concentrations ranging from 1.25 to 10 nM) or in combination with Fed (at 100 and 300 nM) or Rux (at 30 and 100 nM). Treatment was added at the beginning and maintained throughout the 14-day incubation period without compound washout.

To test the effects of Compound (I) on the functionality of normal hematopoietic progenitors, colony-forming assays were also done with bone marrow CD34$^+$ cells from healthy volunteers using the same conditions of treatment as described for MF samples.

Colony forming unit (CFU) data acquisition and automatic colony counting were performed using the STEMvision device and software (StemCell Technologies, Vancouver, Canada). Counting corrections according to standard criteria were done manually by a trained user. GraphPad Prism 7 was used for data plotting and analysis.

Figure 11:
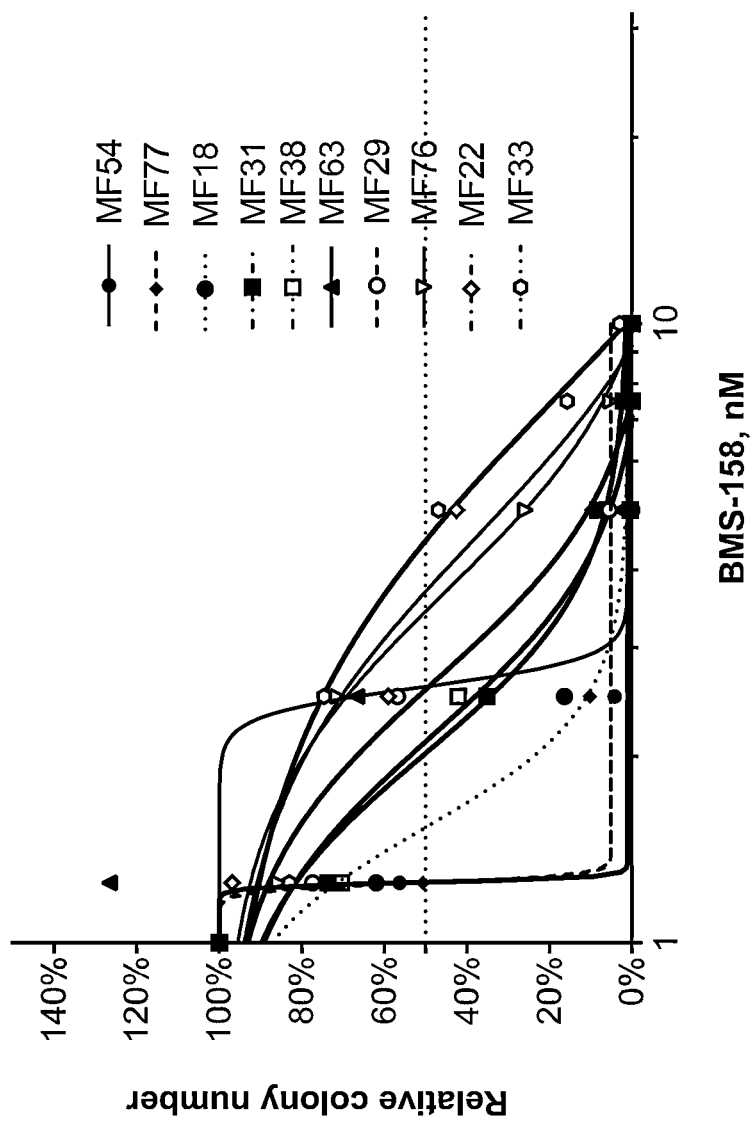
FIG. 11 shows the effect of Compound (I) (BMS-158)_on colony formation in primary human samples from myelofibrosis patients.

Different sensitivity to Compound (I) was observed among 10 primary human myelofibrosis samples (FIG. 11). The IC50 values for inhibition of colonies were in the range of 1.25 to 4.46 nM (FIG. 11).

Figure 12A:
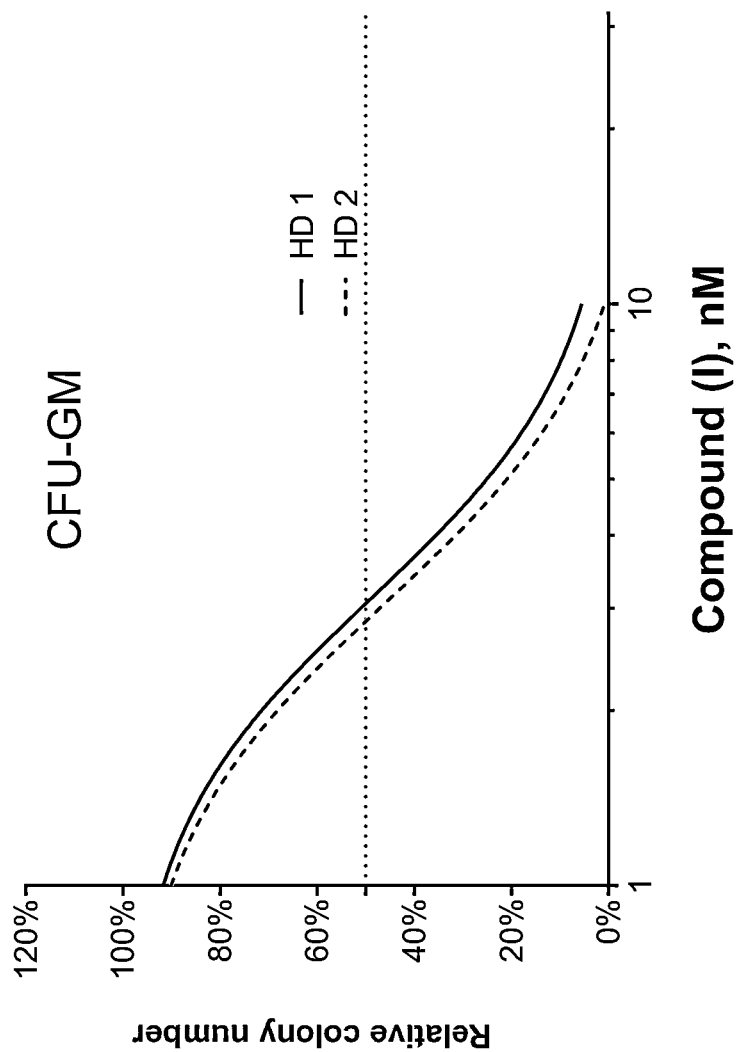
FIG. 12A shows the inhibition of granulo-monocytic progenitors (CFU-GM, colony forming unit of granulocyte/monocyte) from two different healthy donors treated with Compound (I).
Figure 12B:
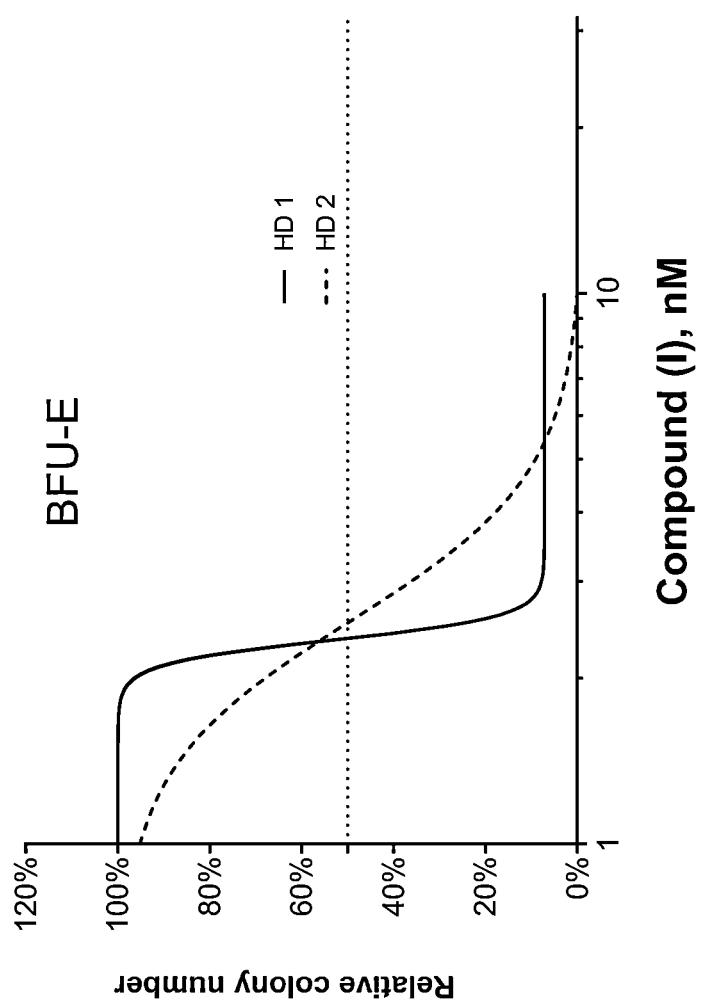
FIG. 12B shows the inhibition of erythroid progenitors (BFU-E, burst forming unit of erythrocytes/monocyte) from two different healthy donors treated with Compound (I).

Evaluation of Compound (I) effects in normal progenitors using clonogenic assays showed impaired functionality of both CFU of granulocyte/monocyte (CFU-GM) and burst forming unit of erythrocytes (BFU-E). Results showed IC50 values for inhibition of CFU-GM and BFU-E that were comparable in magnitude between donors and were in the range of 3 and 2.3 nM (FIGS. 12A and 12B).

To analyze the beneficial effects of Compound (I) in MF cells versus normal bone marrow progenitors, a score called therapeutic index (TI) was calculated as the ratio of IC50 in each MF sample versus the average IC50 in normal bone marrow CD34$^+$ cells. As shown in Table 1, the therapeutic index value was >1 fold in 7 out of 10 MF samples tested and sensitivity to Compound (I) was not clearly related with JAK2 mutational status.

TABLE 1

IC50 Values for Compound (I) in Primary Myelofibrosis Cells From Peripheral Blood Samples

| Sample ID | IC 50 Compound (I) (nM) | Mutation |
| --- | --- | --- |
| MF 54 | 1.25 | JAK2 |
| MF 77 | 1.27 | JAK2 |
| MF 18 | 1.58 | JAK2 |
| MF 31 | 2.02 | CALR |
| MF 38 | 2.11 | WT |
| MF 29 | 2.56 | JAK2 |
| MF 63 | 2.60 | CALR |
| MF 76 | 3.43 | JAK2 |
| MF 22 | 3.70 | WT |
| MF 33 | 4.46 | CALR | nM = nanoMolar; MF = Myelofibrosis

To further investigate the therapeutic potential of Compound (I) in MF, the compound was also tested in combination with Fed or Rux in both, primary cells from MF patients and healthy donors using a colony formation assay.

Figure 13A:
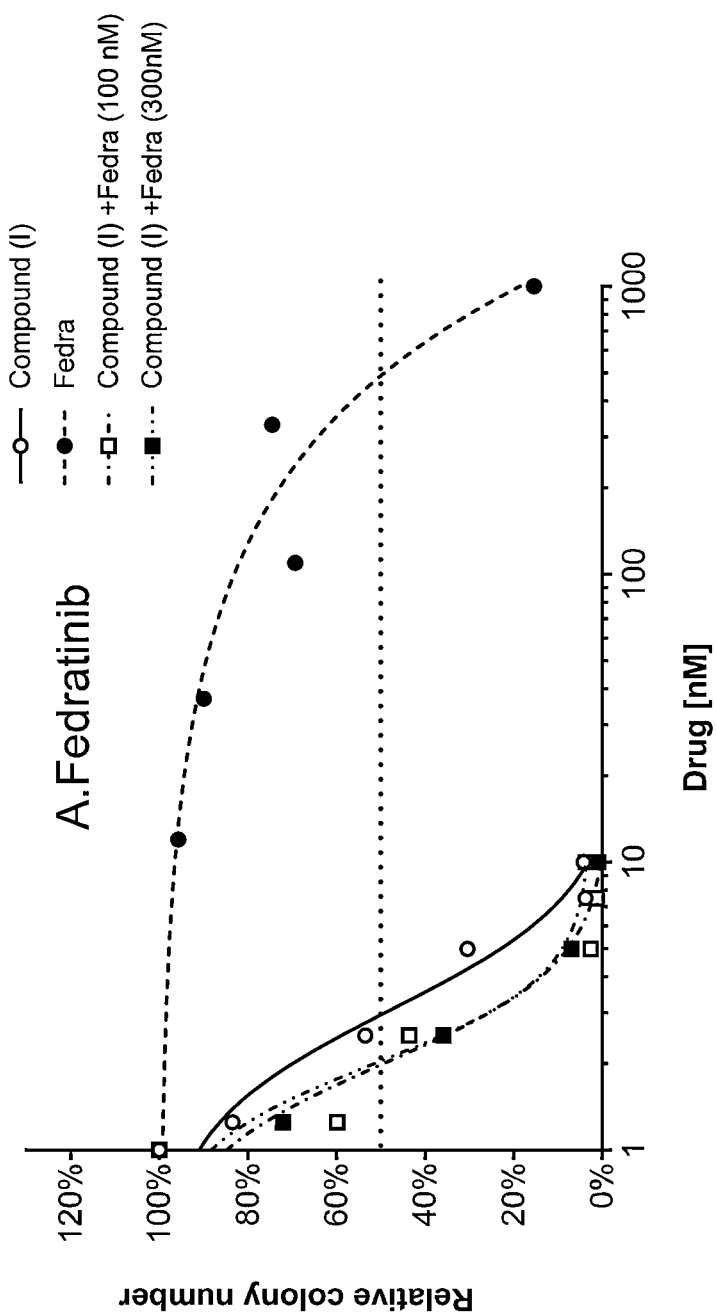
FIG. 13A shows a plot of relative colony number formed by bone marrow $CD34^+$ cells from two healthy donors treated with Compound (I) (light blue curve), fedratinib (grey curve) and the combination of Compound (I) with 100 nM fedratinib (medium blue curve) or 300 nM fedratinib (dark blue curve) for 14 days. Data show donor's mean and effect on CFU-GM.
Figure 13B:
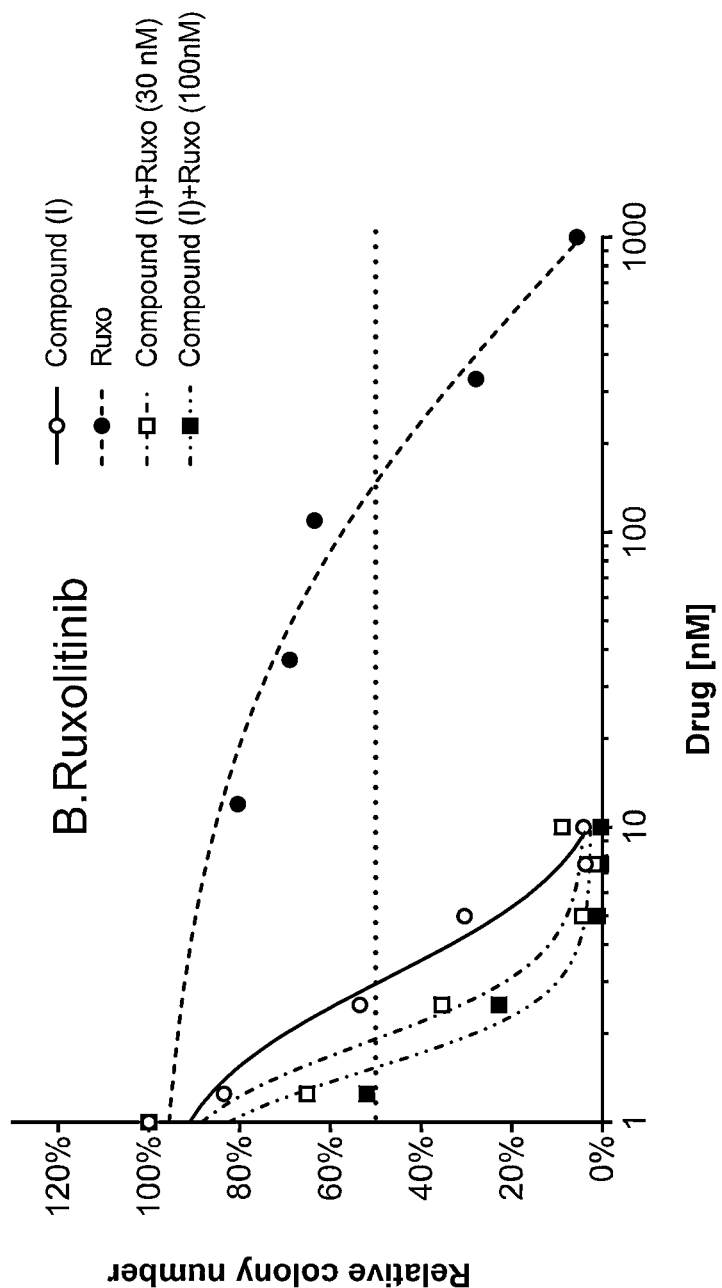
FIG. 13B shows a plot of relative colony number formed by bone marrow $CD34^+$ cells from two healthy donors treated with Compound (I) (light blue curve), ruxolitinib (grey curve) and the combination of Compound (I) with 30 nM ruxolitinib (medium blue curve) or 100 nM ruxolitinib (dark blue curve) for 14 days. Data show donor's mean and effect on CFU-GM.

The number of normal progenitors was reduced by the combinations of Compound (I) with both JAK2-inhibitors (FIGS. 13A and 13B).

Figure 14A:
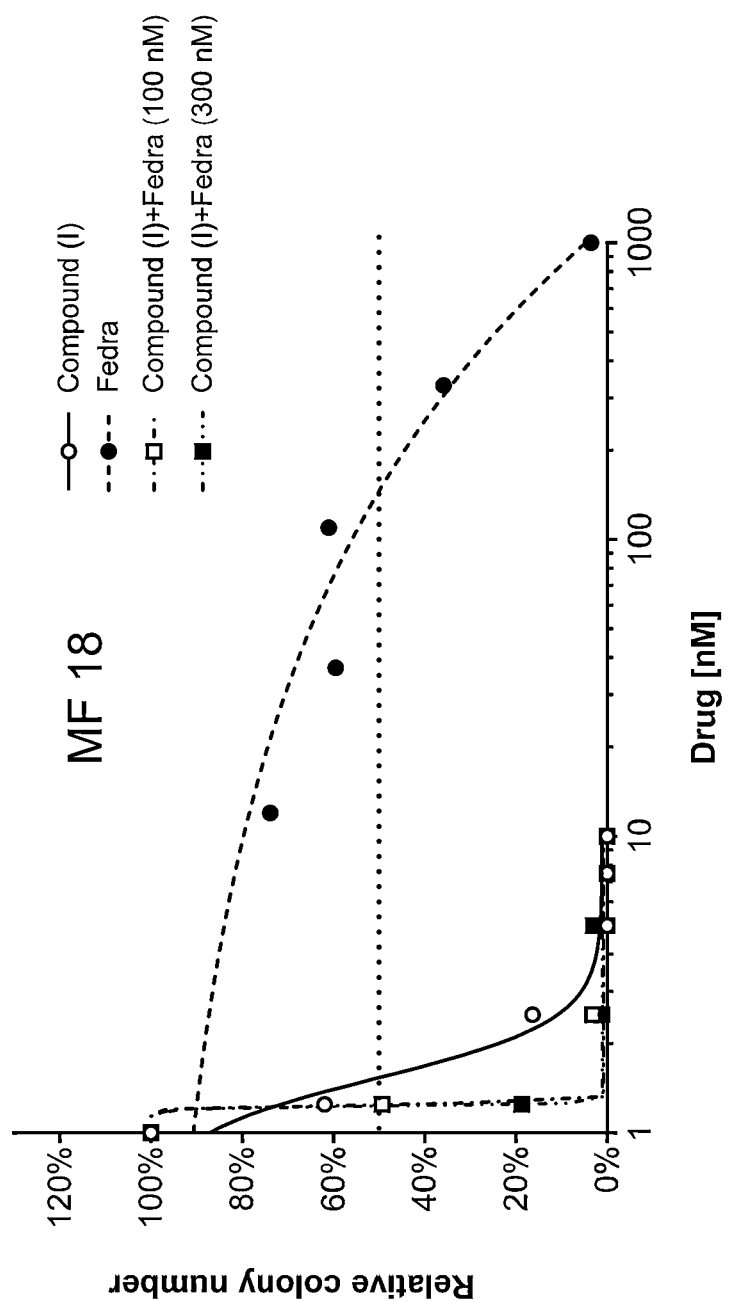
FIG. 14A shows a plot of relative colony number formed by cells derived from a myelofibrosis patient (Patient A) treated with Compound (I) (light blue curve), fedratinib (grey curve) and the combination of Compound (I) with 100 nM fedratinib (medium blue curve) or 300 nM fedratinib (dark blue curve) for 14 days.

An enhanced effect of the combination of Compound (I) and Fed on colony formation of cells from myelofibrosis patients was observed (FIG. 14A).

As shown in Table 2, moderated synergistic/additive effects of the combination of Compound (I) with Fed were observed in 8 out of 10 samples although these effects were not accompanied by a TI improvement. Samples that did not show effect when Compound (I) and Fed were combined, were resistant to Fed (in bold).

TABLE 2

IC50 values in Primary Myelofibrosis Cells when Compound (I) is Combined with Fedratinib

| Sample ID | IC50 Compound (I) (nM) | IC50 FEDR (nM) | IC50 Cmpd (I) + F100 (nM) | IC50 Cmpd (I) + F300 (nM) | Mutation |
| --- | --- | --- | --- | --- | --- |
| MF 54 | 1.25 | 381 | 0.99 | 1.09 | JAK2 |
| MF 77 | 1.27 | 695 | 1.89 | 0.9 | JAK2 |
| MF 18 | 1.58 | 146.2 | 1.23 | 0.77 | JAK2 |
| MF 31 | 2.02 | 908 | 1.98 | 1.73 | CALR |
| MF 38 | 2.11 | 931 | 1.68 | 1.65 | WT |
| MF 29 | 2.56 | 472 | 1.74 | 1.56 | JAK2 |
| MF 63 | 2.6 | 779 | 1.4 | 1.15 | CALR |
| MF 76 | 3.43 | >1000 | 3.77 | 3.2 | JAK2 |
| MF 22 | 3.7 | 309 | 2.56 | 1.94 | WT |
| MF 33 | 4.46 | 930 | NA | 4.22 | CALR |

Figure 14B:
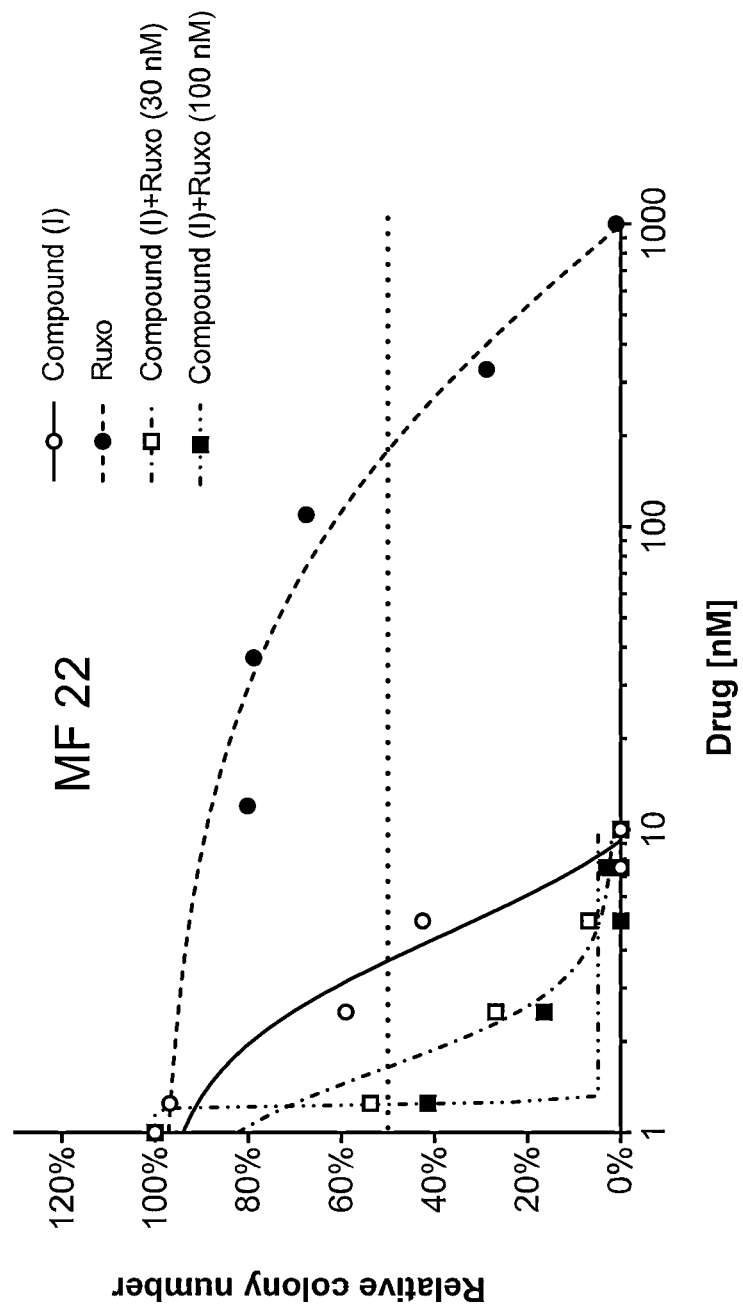
FIG. 14B shows a plot of relative colony number formed by cells derived from a myelofibrosis patient (Patient B) treated with Compound (I) (light blue curve), ruxolitinib (grey curve) and the combination of Compound (I) with 30 nM ruxolitinib (medium blue curve) or 100 nM ruxolitinib (dark blue curve) for 14 days.

The combination with Rux enhanced the Compound (I) activity in 6 out of 10 MF samples However, when that effect was compared with the effect in normal progenitors, TI improvement mediated by this combination was observed only 1 sample (FIG. 14B, MF22). Samples that did not show effect when Compound (I) and Rux were combined were very resistant to Rux (in bold; Table 3).

TABLE 3

IC50 values in Primary Myelofibrosis Cells when Compound (I) is Combined with Ruxolitinib

| Sample ID | IC50 Cmpd (I) (nM) | IC50 RUX (nM) | IC50 Cmpd (I) + R30 (nM) | IC50 Cmpd (I) + R100 (nM) | Mutation |
| --- | --- | --- | --- | --- | --- |
| MF 54 | 1.25 | 685.6 | 1.5 | 0.9 | JAK2 |
| MF 77 | 1.27 | 527.8 | 1.2 | 0.9 | JAK2 |
| MF 18 | 1.58 | 35.5 | 1 | 0.8 | JAK2 |
| MF 31 | 2.02 | 283.6 | 2.1 | 1 | CALR |
| MF 38 | 2.11 | 216.7 | 1.5 | 1.2 | WT |
| MF 29 | 2.56 | 211.8 | 1.2 | 1.2 | JAK2 |
| MF 63 | 2.6 | 70.6 | 2 | 1.4 | CALR |
| MF 76 | 3.43 | 685.6 | 3.3 | 3.1 | JAK2 |
| MF 22 | 3.7 | 211.8 | 1.4 | 1.1 | WT |
| MF 33 | 4.46 | 862 | 5.2 | 4.3 | CALR |

Example 3—Phase IB/2 Study of Compound (I) (Aka Compound (1)) Alone or in Combination with Ruxolitinib or Fedratinib in Participants with Intermediate or High Risk Myelofibrosis Objectives and Endpoints:

| Objectives | Endpoints |
| --- | --- |
| Primary Dose Escalation (Part 1) | |
| To assess the safety and tolerability, and to determine the MTD and/or RP2D of Compound (I) in combination with ruxolitinib in previously untreated (1 L) MF participants, and in combination with fedratinib in ruxolitinib-experienced (2 L) MF participants. | Incidence of AEs, SAEs, AEs meeting protocol-defined DLT criteria, AEs leading to discontinuation, and death. |

-continued

| Objectives | Endpoints |
| --- | --- |
| Dose Expansion (Part 2) | |
| To further determine the safety and tolerability of Compound (I) in combination with ruxolitinib in 1 L or as an "add-on" to ruxolitinib in MF participants, and in combination with fedratinib, or as monotherapy, in 2 L MF participants at the RP2D. Secondary | Incidence of AEs, SAEs, AEs leading to discontinuation, and death. |
| To assess the preliminary efficacy of Compound (I) in combination with ruxolitinib in 1 L or as an "add-on" to ruxolitinib in MF participants or in combination with fedratinib, or as monotherapy in 2 L MF participants based on SVR (modified IWG-MRT2013). | SVR at end of Cycle 6 (and response rate defined as proportion of participants with SVR ≥35%) by MRI (preferred) or CT (if MRI is contraindicated) assessed by BICR. |
| To evaluate MF-associated symptoms as measured by the MFSAF of participants treated with Compound (I) monotherapy and in combination with either ruxolitinib or fedratinib in Part 2. | SRR and additional measures based on TSS measured by MFSAF; SRR is calculated at the end of Cycle 6 (and defined as the proportion of participants with ≥50% reduction in TSS). |
| Improvement in anemia in Part 2 (modified IWG-MRT 2013) based on pre-defined changes in both TI participants and TD participants. | For TI, proportion of participants having ≥2.0 g/dL Hgb increase over baseline, and for TD, proportion of participants becoming TI as measured by the absence of RBC transfusions, ESA and hydroxyurea over any consecutive 12-week period. |
| To characterize the PK of Compound (I) in combination with ruxolitinib and in combination with fedratinib and in monotherapy. | Summary of PK parameters of Compound (I) in combination with ruxolitinib and in combination with fedratinib, and in Compound (I) monotherapy. |
| SDPFS of participants treated with Compound (I) in combination with either ruxolitinib or fedratinib and in monotherapy. | Time from Dose 1, Day 1 to death due to any reason or disease progression (per modified IWG-MRT 2013) assessed by BICR; median SDPFS and SDPFS rates at 6 months and 12 months. |

Overall Design:

This study is a multicenter, open-label, Phase 1b/2, dose escalation and expansion study in participants with intermediate or high risk PMF, post-polycythemia vera MF, or post-essential thrombocythemia MF.

The study will consist of the following 3 periods:

Up to 28-day Screening Period: Screening period will start at the time of informed consent form signature and the duration is up to 28 days (+3 days) before Dose 1 of study treatments.

Treatment Period:
  Part 1: Dose Escalation
  Part 1A—Ruxolitinib Combo cohorts (Compound (I)+ ruxolitinib) and
  Part 1B—Fedratinib Combo cohorts (Compound (I)+ fedratinib), followed by
  Part 2: Dose Expansion
  Part 2A1—Ruxolitinib Combo cohort (Compound (I)+ ruxolitinib)
  Part 2A2 add-on to ruxolitinib cohort (Compound (I)+ ruxolitinib) and
  the randomized Part 2B1-Fedratinib Combo Arm (Compound (I)+fedratinib) versus Part 2B2-Compound (I) Mono Arm (Compound (I) alone)
Safety Follow-up: The first visit is 28 days after last dose of Compound (I), and the following visits are scheduled every 30 days (±7 days) up to maximum 90 days after last dose of Compound (I).

Survival Follow-up Period: Two years for all cohorts/arms. Participants will be followed every subsequent 3 months (±2 weeks) for survival follow-up for up to 2 years or until death, withdrawal of consent, lost to follow-up, or the end of study, whichever occurs first.

Figure 15A:
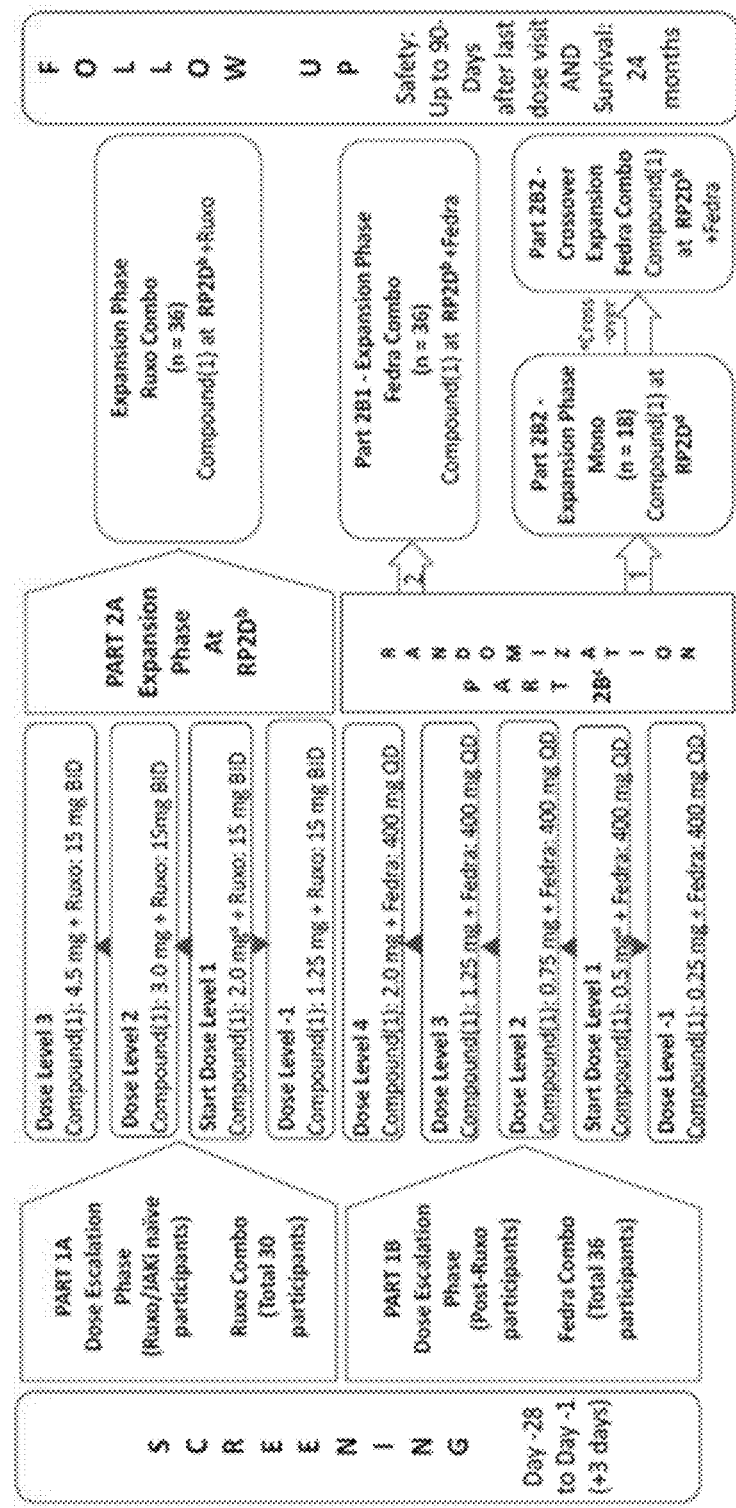
FIGS. 15A and 15B show schematics of the Phase IB/2 study design described in Example 3.
Figure 15B:
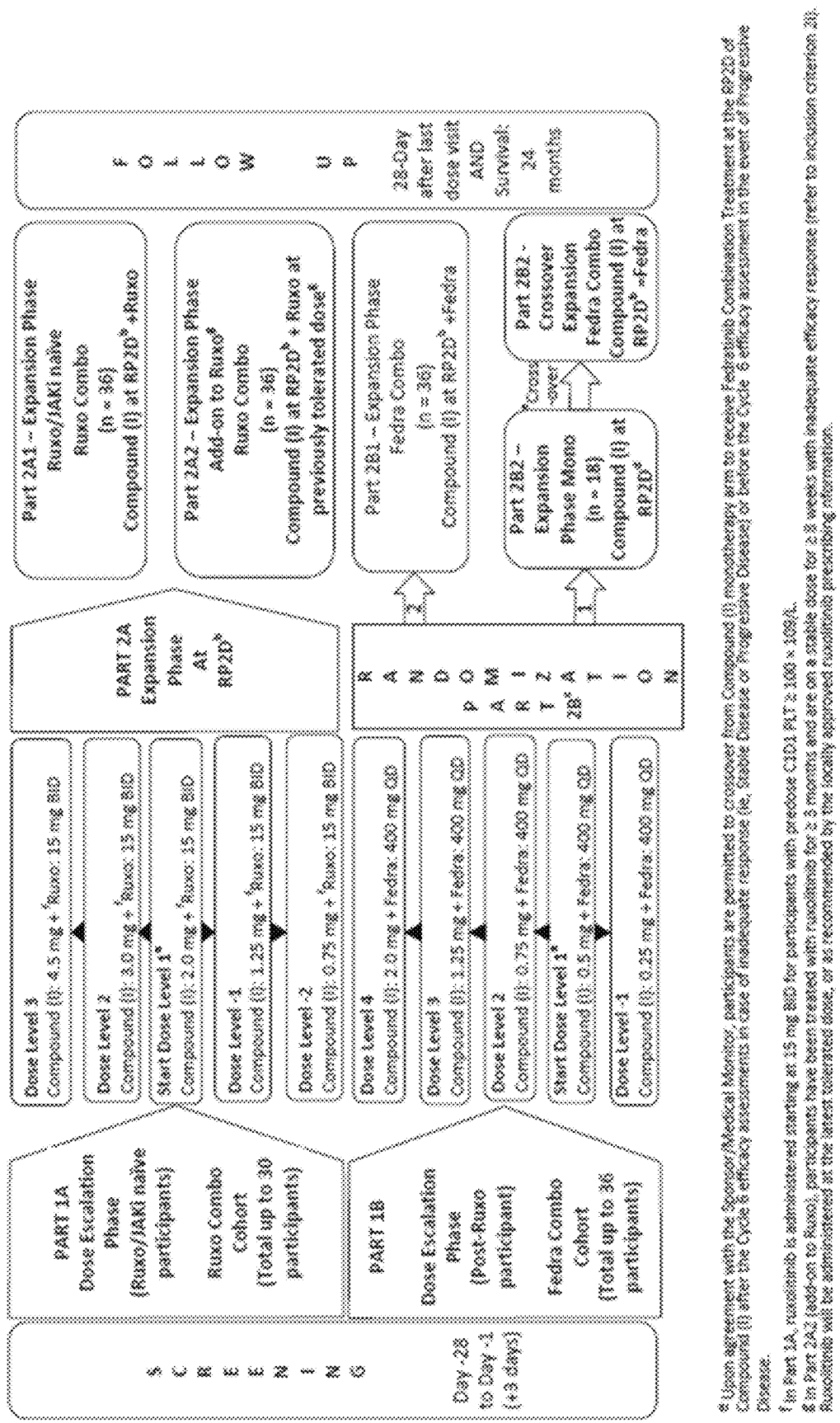

A schematic of the study design is presented in FIGS. 15A and 15B.

Example 4—Caspase 3/7 Incucyte Live Cell Assays

For single agent and combination drug experiments, cells were seeded in 96-well plates at 5,000 cells per well for 5 days in 100 µL of 1:1000 Caspase 3/7 green dye (Essen Bioscience, Ann Arbor, Michigan, US) media containing either 0.1% DMSO, varying concentrations of drug, or combination of BET and JAK inhibitor drugs.

Cells were placed into an Incucyte Zoom System (Essen Bioscience, Ann Arbor, Michigan, US) and programmed to capture images every 4 hours for 5 days (120 hours). Cells were then analyzed using the Incucyte Zoom 2018A Software.

CellTiter-Glo® (CTG) assay (Promega Corporation, Madison, Wisconsin, US) results are expressed as mean percentage growth±SD in triplicates. IC50s sigmoidal curves were calculated using nonlinear regression (three parameters) statistical software package in GraphPad Prism 8 (GraphPad Software, La Jolla, CA, USA) from the active compounds. Graphs represent the sigmoidal curves for the IC50 calculation of a representative experiment.

Caspase 3/7 Incucyte live cell imaging results are expressed as mean Caspase 3/7 count (1/image) SD in duplicates of a representative experiment.

Figure 16:
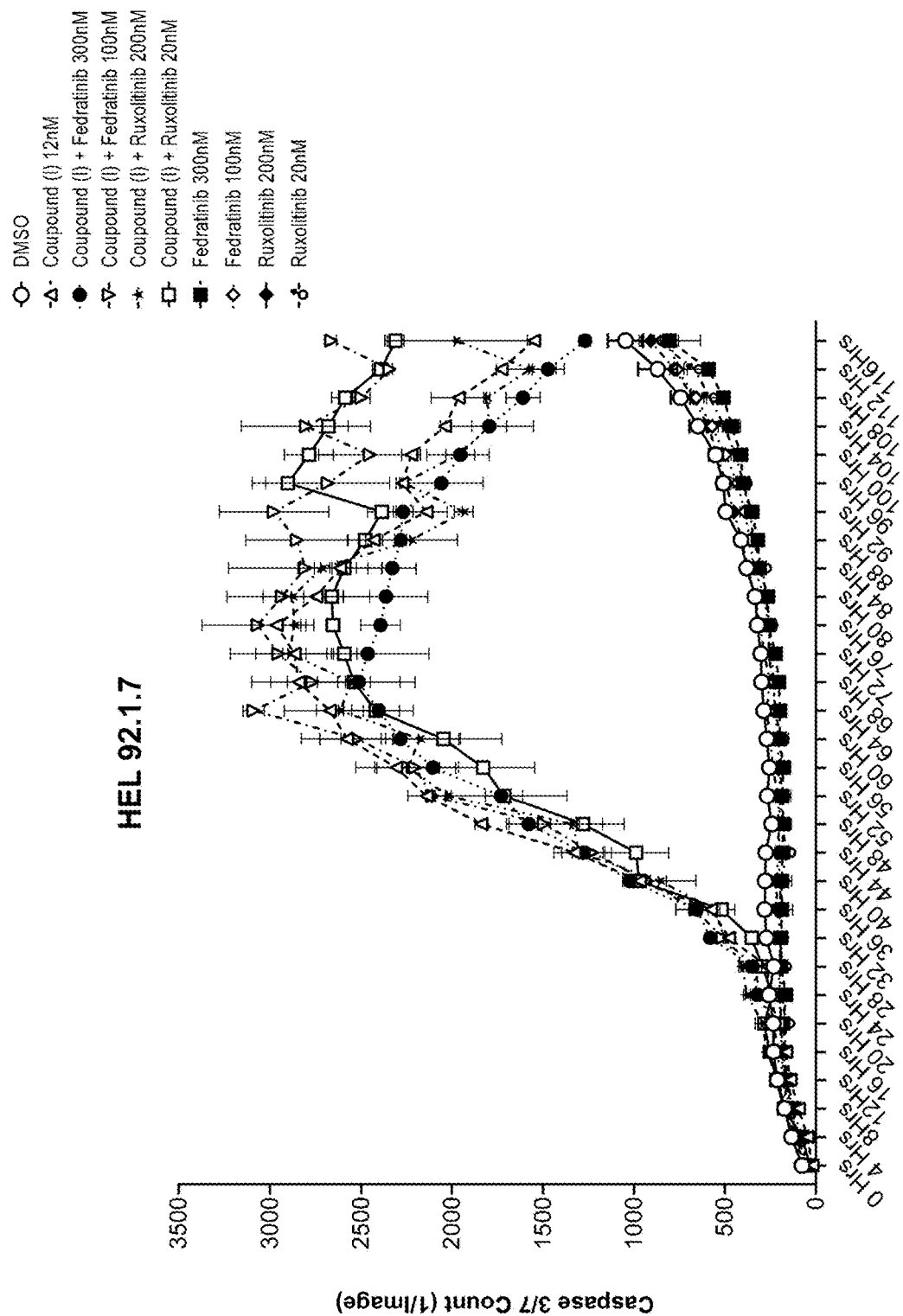
FIG. 16 shows the activation of Caspase-3 over time in HEL cells when treated with Compound (I) (green triangle), fedratinib (yellow circle and red square), ruxolitinib (grey circle and gold symbol), a combination of Compound (I) and fedratinib (black circle and black triangle), or a combination of Compound (I) and ruxolitinib (peach triangle or lavender circle).
Figure 17:
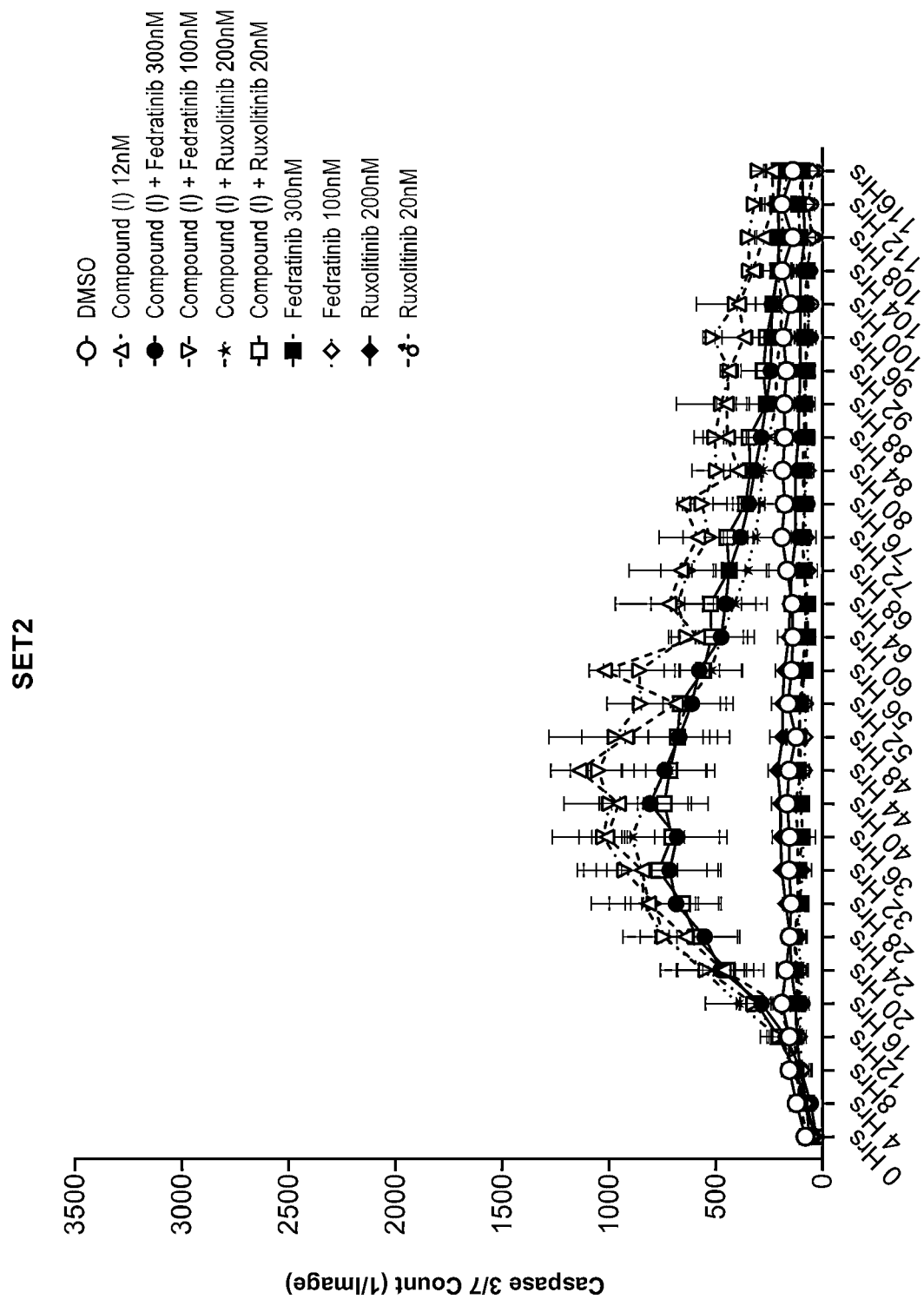
FIG. 17 shows the activation of Caspase-3 over time in SET-2 cells when treated with Compound (I) (green triangle), fedratinib (yellow circle and red square), ruxolitinib (grey circle and gold symbol), a combination of Compound (I) and fedratinib (black circle and black triangle), or a combination of Compound (I) and ruxolitinib (peach triangle or lavender circle).
Figures 18A, 18B:
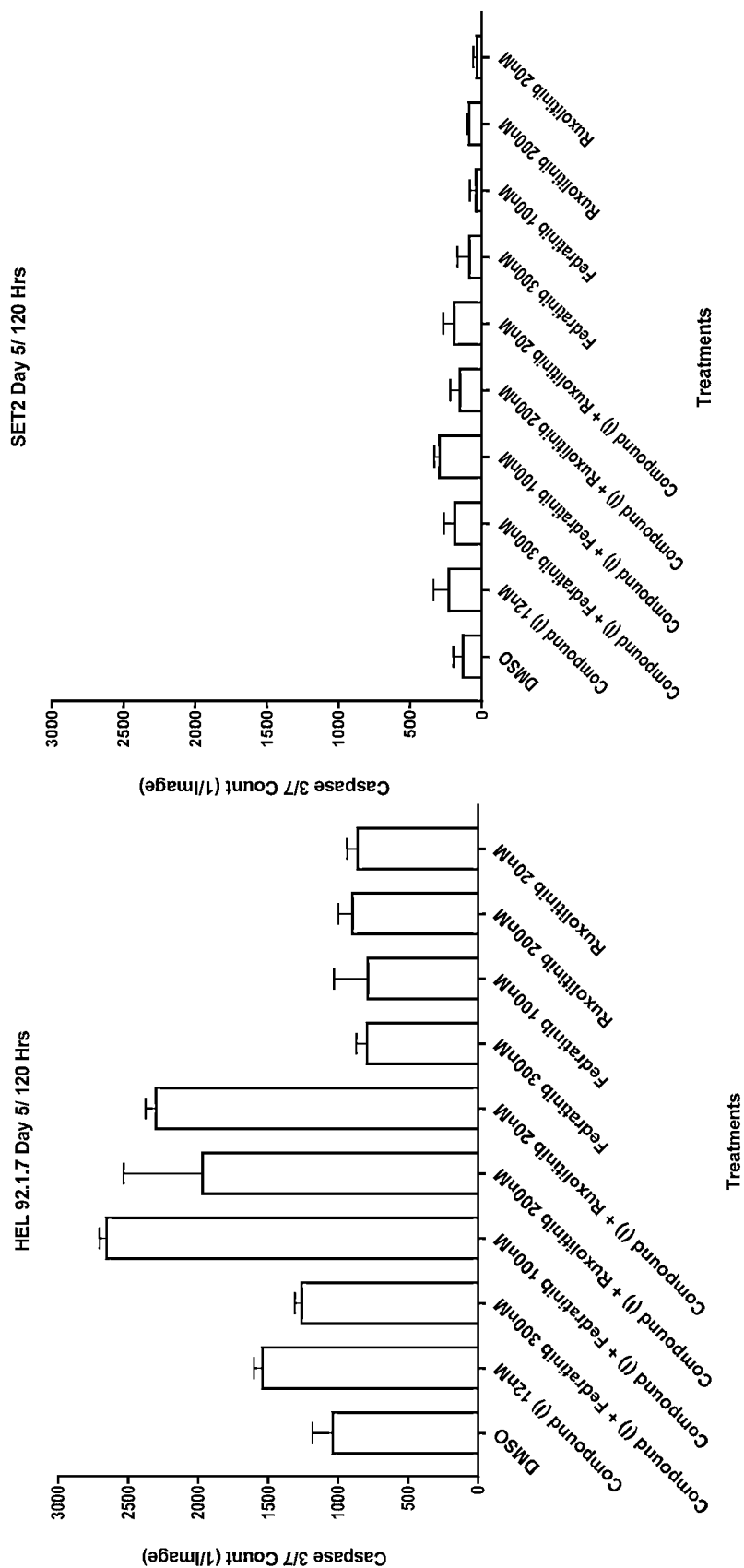
FIG. 18A shows the activation of Caspase-3 at 120 hours in HEL 92.1.7 cells when treated with Compound (I), fedratinib, ruxolitinib, a combination of Compound (I) and fedratinib, or a combination of Compound (I) and ruxolitinib.
FIG. 18B shows the activation of Caspase-3 at 120 hours in SET-2 cells when treated with Compound (I), fedratinib, ruxolitinib, a combination of Compound (I) and fedratinib, or a combination of Compound (I) and ruxolitinib.

As shown in FIGS. 16 and 17, combinations of Compound (I) with fedratinib or Compound (I) with ruxolitinib activated Caspase-3 at a greater rate than fedratinib or ruxolitinib alone, indicating that the combination effectively induces cell death/apoptosis. FIGS. 18A and 18B show the quantitation of the data in FIGS. 16 and 17 at 120 hours.

Example 5—Cell Viability Assays

Cells were seeded in 96-well plates at 10,000 cells per well in 100 µL of media containing either 0.1% DMSO or varying concentrations of drug. Cell viability was determined 3 days and 5 days later via the CellTiter GloLuminescent Cell Viability Assay from Promega (Madison, WI) according to the manufacturer's protocol. Specifically, 50 µL of reagent was added to each well and plates were incubated for 10 minutes in the dark to stabilize the luminescent signal. Luminescence was then detected using a chemiluminescence detection system (EnVision Multimode Microplate Reader; PerkinElmer).

Figure 19A:
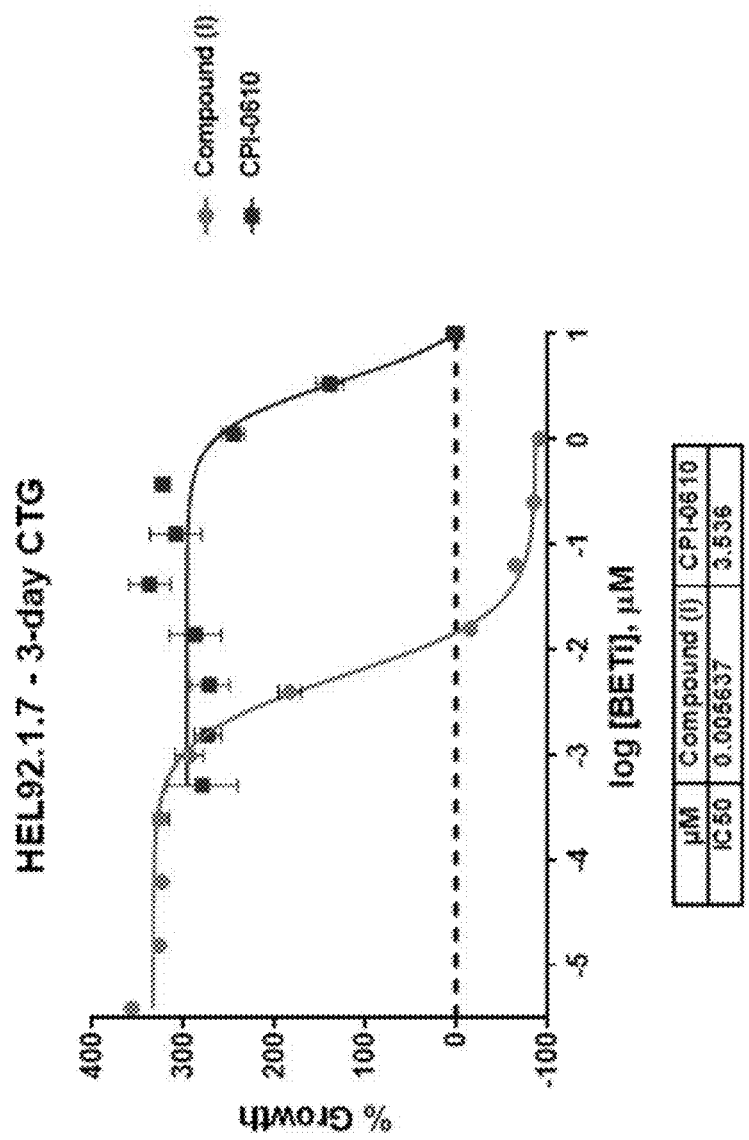
FIG. 19A shows plots of Compound (I) and CPI-0610 viability in HEL92.1.7 cells on Day 3.
Figure 19B:
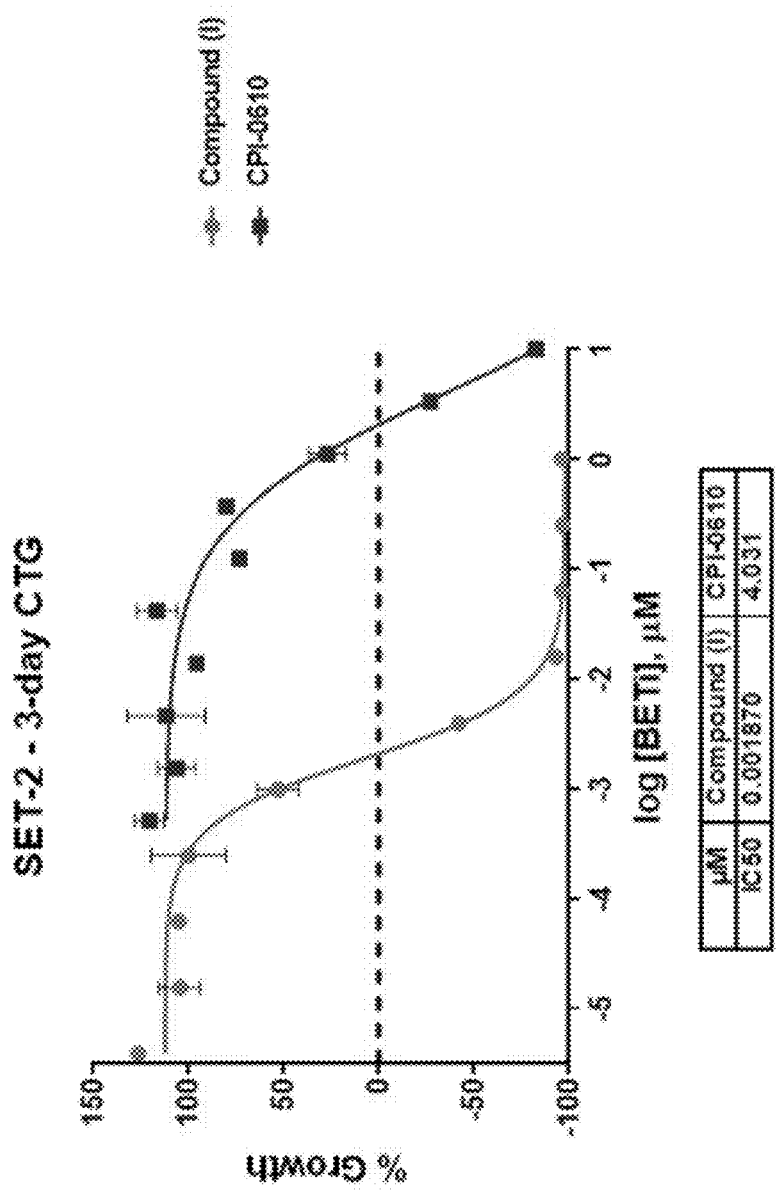
FIG. 19B shows plots of Compound (I) and CPI-0610 viability in SET-2 cells on Day 3.

Compound (I) showed a single agent IC50 of 15 nM and 19 nM in HEL92.1.7 on Days 3 and 5, respectively (FIGS. 19A and 19B).

Compound (I) showed a single agent IC50 of 2.8 nM and 2.4 nM in SET-2 on Days 3 and 5, respectively (FIGS. 20A and 20B).

A comparison of Compound (I) against the known BET inhibitor CPI-0610 in HEL92.1.7 and SET-2 cells is shown in FIGS. 19A and 19B, respectively. As shown in the figures, Compound (I) showed better activity against both cell lines compared to CPI-0610.

Example 6—PK Studies—Compound (I)

A first-in-human study was conducted on Compound (I) with select advanced tumors and hematologic malignancies.

PK data was available from 65 subjects across 5 doses and 3 schedules. Intensive samples were collected on Cycle 1 Day 1 and Cycle 2 Day 5, Day 7, or Day 14 based on dosing schedule (5 days on/2 days off, 7 days on/14 days off, and 14 days on/7 days off). PK data for the days on/2 days off schedule is shown in Table 4. The terminal half-life of a single dose of Compound (I) during this dosing schedule was found to be approximately 64 hours.

TABLE 4

Compound (I) $C_{max}$ Values (Geometric Mean)

| Dose (mg) | Number of Subjects | $C_{max}$ Cycle 2 Steady State (nM)* |
|---|---|---|
| 0.75 | 5 | 272 |
| 1.25 | 4 | 577 |
| 2.0 | 7 | 892 |
| 3.0 | 9 | 1202 |
| 4.5 | 8 | 1842 |

*Geometric Mean of Cmax values were taken at Cycle 2 Day 5 corresponding to the dosing schedule 5 days on/2 days off.

In contrast, clinical studies where CPI-0610 was dosed at 125 mg QD provided a Cmax of 4 micromolar and a $T_{1/2}$ of 16 hours.

It is to be appreciated that the Detailed Description section, and not the Summary and Abstract sections, is intended to be used to interpret the claims. The Summary and Abstract sections may set forth one or more but not all exemplary aspects of the present disclosure as contemplated by the inventor(s), and thus, are not intended to limit the present disclosure and the appended claims in any way.

The present disclosure has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific aspects will so fully reveal the general nature of the disclosure that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

What is claimed is:

1. A method of treating myelofibrosis in a subject in need thereof, the method comprising orally administering to the subject:

a compound of formula (I):

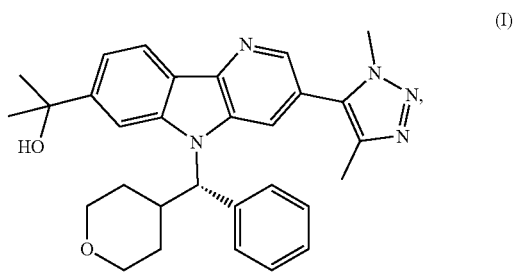 [SMILES: Cc1nnn(C)c1-c1cnc2c3ccc(C(C)(C)O)cc3n([C@H](c3ccccc3)C3CCOCC3)c2c1]

or a pharmaceutically acceptable salt thereof; and
a compound of formula (II):

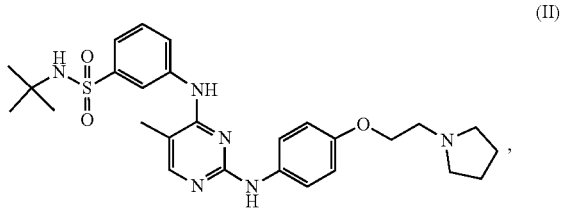 [SMILES: Cc1cnc(Nc2ccc(OCCN3CCCC3)cc2)nc1Nc1cccc(S(=O)(=O)NC(C)(C)C)c1]

or a pharmaceutically acceptable salt and/or solvate thereof;
wherein the compound of formula (I), or the pharmaceutically acceptable salt thereof, is administered at a daily dose of 0.25 mg, 0.5 mg, 0.75 mg, or 1.0 ma on a five days on, two days off schedule for three weeks, and wherein the compound of formula (II), or the pharmaceutically acceptable salt and/or solvate thereof, is administered at a daily dose of about 400 mg.

2. The method of claim 1, wherein the compound of formula (I), or the pharmaceutically acceptable salt thereof, and the compound of formula (II), or the pharmaceutically acceptable salt and/or solvate thereof, are administered concurrently.

3. The method of claim 1, wherein the compound of formula (I), or the pharmaceutically acceptable salt thereof, and the compound of formula (II), or the pharmaceutically acceptable salt and/or solvate thereof, are administered sequentially.

4. The method of claim 1, wherein the compound of formula (II) or a pharmaceutically acceptable salt and/or hydrate thereof is administered.

5. The method of claim 1, wherein the dihydrochloride monohydrate of the compound of formula (II) is administered.

6. The method of claim 1, wherein the myelofibrosis is relapsed/refractory myelofibrosis.

7. The method of claim 1, wherein the subject is treatment naïve.

8. The method of claim 1, wherein the subject has previously been treated with ruxolitinib.

9. The method of claim 1, wherein the myelofibrosis is primary myelofibrosis.

10. The method of claim 9, wherein the primary myelofibrosis is selected from intermediate risk primary myelofibrosis and high risk primary myelofibrosis.

11. The method of claim 1, wherein the myelofibrosis is secondary myelofibrosis.

12. The method of claim 1, wherein the myelofibrosis is post-essential thrombocythemia myelofibrosis.

13. The method of claim 1, wherein the myelofibrosis is post-polycythemia vera myelofibrosis.

\* \* \* \* \*

UNITED STATES PATENT AND TRADEMARK OFFICE
CERTIFICATE OF CORRECTION

PATENT NO. : 12,357,621 B2
APPLICATION NO. : 17/680569
DATED : July 15, 2025
INVENTOR(S) : Ida Aronchik et al.

Page 1 of 1

It is certified that error appears in the above-identified patent and that said Letters Patent is hereby corrected as shown below:

In the Claims

In Column 48, Claim 1, Line 33, delete "ma," and insert -- mg --, therefor.

Signed and Sealed this
Twenty-seventh Day of January, 2026

John A. Squires
*Director of the United States Patent and Trademark Office*